US011224383B2

(12) United States Patent
Niichel et al.

(10) Patent No.: US 11,224,383 B2
(45) Date of Patent: Jan. 18, 2022

(54) WIRELESS COMMUNICATIONS SYSTEM INTEGRATING ELECTRONICS INTO ORALLY INGESTIBLE PRODUCTS FOR CONTROLLED RELEASE OF ACTIVE INGREDIENTS

(71) Applicant: Veloce Corporation, Denver, CO (US)

(72) Inventors: Robert Niichel, Greenwood Village, CO (US); Kevin McWilliams, Boulder, CO (US); John English, Boulder, CO (US); Amir H. Torbati, Westminster, CO (US); Christopher M. Yakacki, Denver, CO (US)

(73) Assignee: VELOCE CORPORATION, Denver, CO (US)

( * ) Notice: Subject to any disclaimer, the term of this patent is extended or adjusted under 35 U.S.C. 154(b) by 0 days.

(21) Appl. No.: 16/656,481

(22) Filed: Oct. 17, 2019

(65) Prior Publication Data
US 2020/0046294 A1 Feb. 13, 2020

Related U.S. Application Data

(63) Continuation of application No. 15/668,487, filed on Aug. 3, 2017, now abandoned, which is a
(Continued)

(51) Int. Cl.
*A61B 5/00* (2006.01)
*A61K 41/00* (2020.01)
(Continued)

(52) U.S. Cl.
CPC .......... *A61B 5/6861* (2013.01); *A61B 5/0002* (2013.01); *A61B 5/061* (2013.01);
(Continued)

(58) Field of Classification Search
CPC .. A61M 31/00; A61M 37/00; A61M 2205/35; A61M 2205/3507;
(Continued)

(56) References Cited

U.S. PATENT DOCUMENTS 3,118,439 A 1/1964 Perrenoud
3,485,235 A 12/1969 Felson
(Continued)

FOREIGN PATENT DOCUMENTS

WO 1996010994 A1 4/1996

OTHER PUBLICATIONS

Abbott, Jake J. "Parametric design of tri-axial nested helmholtz coils," Rev. Sci. Instrum. 86 (2015), No. 5, 05471, 10 pages.
(Continued)

*Primary Examiner* — Kami A Bosworth
(74) *Attorney, Agent, or Firm* — Perkins Coie LLP

(57) ABSTRACT

Various embodiments of the present disclosure include a consumable capsule containing an active ingredient in at least one compartment movably sealed by a stimuli responsive actuator, and an activation device configured to communicate with the consumable capsule. The activation device is configured to emit a wireless signal to activate the stimuli responsive actuator of the consumable capsule, and the consumable capsule is configured to release the active ingredient into an external environment based on the activation of the stimuli responsive actuator.

10 Claims, 36 Drawing Sheets

Related U.S. Application Data continuation of application No. 14/946,478, filed on Nov. 19, 2015, now Pat. No. 9,750,923.

(60) Provisional application No. 62/191,149, filed on Jul. 10, 2015, provisional application No. 62/134,839, filed on Mar. 18, 2015, provisional application No. 62/081,988, filed on Nov. 19, 2014.

(51) Int. Cl.
*A61M 37/00* (2006.01)
*A61B 5/06* (2006.01)

(52) U.S. Cl.
CPC ............ *A61B 5/4839* (2013.01); *A61K 41/00* (2013.01); *A61K 41/0028* (2013.01); *A61M 37/00* (2013.01); *A61M 2205/3523* (2013.01)

(58) Field of Classification Search
CPC .. A61M 2205/3515; A61M 2205/3523; A61M 2205/3569; A61M 2205/3576; A61M 2205/3592; A61M 39/22; A61M 2039/2433; A61M 2039/2473; A61M 2039/2486; A61M 2210/1046; A61M 2210/1053; A61M 2210/1057; A61M 2210/106; A61M 2210/1064; A61B 5/4839; A61B 5/6861; A61B 5/06; A61B 5/061; A61B 5/062; A61B 5/063; A61B 5/065; A61B 5/068
See application file for complete search history.

(56) References Cited

U.S. PATENT DOCUMENTS

| | | | |
|---|---|---|---|
| 4,239,040 A | 12/1980 | Hosoya et al. | |
| 4,425,117 A | 1/1984 | Hugemann et al. | |
| 4,507,115 A | 3/1985 | Kambara et al. | |
| 5,167,626 A * | 12/1992 | Casper | A61B 5/073 |
| | | | 600/582 |
| 5,279,607 A | 1/1994 | Schentag et al. | |
| 5,395,366 A | 3/1995 | D'Andrea et al. | |
| 6,464,687 B1 * | 10/2002 | Ishikawa | A61B 5/14532 |
| | | | 604/891.1 |
| 6,733,485 B1 | 5/2004 | Whitehurst et al. | |
| 7,932,798 B2 | 4/2011 | Tolle et al. | |
| 7,952,322 B2 | 5/2011 | Partovi et al. | |
| 8,766,487 B2 | 7/2014 | Dibben et al. | |
| 8,827,889 B2 | 9/2014 | Smith et al. | |
| 8,847,548 B2 | 9/2014 | Kesler et al. | |
| 8,884,469 B2 | 11/2014 | Lemmens et al. | |
| 9,750,923 B2 | 9/2017 | Niichel et al. | |
| 2002/0013555 A1 | 1/2002 | Seward | |
| 2002/0055734 A1 | 5/2002 | Houzego et al. | |
| 2002/0198470 A1 | 12/2002 | Imran et al. | |
| 2004/0122315 A1 * | 6/2004 | Krill | G01S 7/003 |
| | | | 600/437 |
| 2004/0238769 A1 * | 12/2004 | Perlo | A61K 9/0009 |
| | | | 251/11 |
| 2005/0143623 A1 * | 6/2005 | Kojima | A61B 1/041 |
| | | | 600/109 |
| 2005/0192637 A1 | 9/2005 | Girouard et al. | |
| 2005/0267414 A1 * | 12/2005 | Abraham-Fuchs | A61M 31/00 |
| | | | 604/173 |
| 2006/0142706 A1 * | 6/2006 | Roy | A61N 1/306 |
| | | | 604/296 |
| 2006/0155197 A1 * | 7/2006 | Kishimoto | F16K 31/02 |
| | | | 600/498 |
| 2008/0108885 A1 | 5/2008 | Colvin, Jr. | |
| 2008/0204021 A1 | 8/2008 | Leussler et al. | |
| 2008/0255543 A1 * | 10/2008 | Tanaka | A61M 5/14276 |
| | | | 604/891.1 |
| 2009/0043288 A1 | 2/2009 | Petrakis | |
| 2009/0284255 A1 * | 11/2009 | Zur | G01R 33/04 |
| | | | 324/239 |
| 2009/0306633 A1 | 12/2009 | Trovato et al. | |
| 2010/0102841 A1 | 4/2010 | Kawada et al. | |
| 2010/0191192 A1 * | 7/2010 | Prasad | A61M 39/223 |
| | | | 604/247 |
| 2011/0282415 A1 | 11/2011 | Eckhoff et al. | |
| 2013/0137969 A1 | 5/2013 | Jones | |
| 2013/0274659 A1 | 10/2013 | Imran et al. | |
| 2013/0293025 A1 | 11/2013 | Xu et al. | |
| 2013/0310664 A1 * | 11/2013 | Kozloski | A61M 31/00 |
| | | | 600/302 |
| 2014/0088346 A1 * | 3/2014 | Uhland | A61B 17/43 |
| | | | 600/35 |
| 2014/0135698 A1 | 5/2014 | Zou et al. | |
| 2014/0276218 A1 * | 9/2014 | Hyde | A61B 10/00 |
| | | | 600/575 |
| 2014/0312834 A1 | 10/2014 | Tanabe et al. | |
| 2014/0330256 A1 | 11/2014 | Hyde et al. | |
| 2015/0011874 A1 | 1/2015 | Amoako-Tuffour et al. | |
| 2015/0018612 A1 | 1/2015 | Tange et al. | |
| 2017/0290975 A1 | 10/2017 | Barmaimon et al. | |
| 2018/0160950 A1 | 6/2018 | Rabinovitz et al. | |
| 2020/0046294 A1 | 2/2020 | Niichel et al. | |
| 2020/0113521 A1 | 4/2020 | Jones | |
| 2020/0146632 A1 | 5/2020 | Niichel et al. | |

OTHER PUBLICATIONS

Beiranvand, R. Analyzing the uniformity of the generated magnetic field by a practical one-dimensional helmholtz coils system, Rev. Sci. Instrum. 84 (2013), No. 7, 075109. 12 pages.

Ciuti, Gastone et al., Capsule endoscopy: From current achievements to open challenges, IEEE Rev. Biomed. Eng. 4 (2011), 59-72.

Esen, G. and Fuhrer, M. S. Temperature control of electromigration to form gold nanogap junctions, Appl. Phys. Lett. 87 (2005), No. 26, 263101. 14 pages.

Fawaz, Nidal and Jansen, Dirk. Enhanced telemetry system using cp-qpsk band-pass modulation technique suitable for smart pill medical application, IEEE (2008). 5 pages.

Gentner, Philipp K. et al., Accurate measurement of power transfer to an RFID tag with on-chip antenna, PIERS Proceedings, Moscow Russia, Aug. 19-23, 2012. 216-219.

Jia, Zhiwei et al. A wireless power transmission system for an active capsule endoscope for colon inspection, J. Med Eng Technol. 36 (2012), No. 5, 235-241.

Juchem, Christoph et al., Magnetic field modeling with a set of individual localized coils, Journal of Magnetic Resonance 204 (2010), No. 2, 281-289.

Kim, B. et al, Design and fabrication of a locomotive mechanism for capsule-type endoscopes using shape memory alloys (smas), IEEE/ASME Transactions on Mechatronics 10 (2005), No. 1, 77-86.

Lee, Yong Up et al., In vivo robotic capsules: determination of the number of turns of its power receiving coil, Medical, Biological Engineering, Computing 44 (2006), No. 12, 1121-1125.

Lenaerts, Bert and Puers Robert, Inductive powering of a freely moving system, Sensors and Actuators A: Physical 123-124 (2005), 522-530.

Lenaerts, Bert and Puers Robert, An inductive power link fora wireless endoscope, Biosensors and Bioelectronics 22 (2007), No. 7, 1390-1395.

Li, Hongwei et al., An active endoscopic robot based on wireless power transmission and electromagnetic localization, The International Journal of Medical Robotics and Computer Assisted Surgery 4 (2008), No. 4, 355-367.

Li, Jiangtao. Flexible Multichannel Transcranial Magnetic Stimulation Coil Array, 2015, 1490-93.

Lucarini, Gioia et al. A new concept for magnetic capsule colonoscopy based on an electromagnetic system, International Journal of Advanced Robotic Systems (2015), 1-13.

Mahoney, Arthur W. Advanced methods for controlling untethered magnetic devices using rotating magnetic fields, Ph.D. thesis, The University of Utah, 2014. 68 pages.

(56) References Cited

OTHER PUBLICATIONS

Melling, Daniel et al., The effect of film thickness on polypyrrole actuation assessed using novel non-contact strain measurements, SmartMater. Struct. 22 (2013), No. 10, 104021. 30 pages.
Miura, H. et al., Improvement of the transcutaneous energy transmission system utilizing ferrite cored coils for artificial hearts, IEEE Trans. Magn. 42 (2006), No. 10, 3578-3580.
Pan, Guobing and Wang, Litong, Swallowable wireless capsule endoscopy: Progress and technical challenges, Gastroenterology Research and Practice 2012 (2012), 1-9.
Popek, Katie M. et al. Localization method for a magnetic capsule endoscope propelled by a rotating magnetic dipole field, 2013 IEEE ICRA, Karsruhe Germany. 6 pages.
RamRakhyani, Anil Kumar et al., Design and optimization of resonance-based efficient wireless power delivery systems for biomedical implants, IEEE Trans. Biomed. Circuits Syst. 5 (2011), No. 1, 48-63.
RamRakhyani, Anil Kumar et al., Multicoil telemetry system for compensation of coil misalignment effects in implantable systems, Antennas Wirel. Propag. Lett. 11 (2012), 1675-1678.
Rajagopalan, Ajit et al., Improving power transfer efficiency of a short-range telemetry system using compact metamaterials, IEEE Transactions on Microwave Theory and Techniques 62 (2014), No. 4, 947-955.
Ryu, Munho et al., Three-dimensional power receiver for in vivo robotic capsules, Medical, Biological Engineering, Computing 45 (2007), No. 10, 997-1002.
Soltani, Nima et al., Cellular inductive powering system for weakly-linked resonant rodent implants, IEEE (2013), 350-353.
Son, Donghee et al. Bioresorbable electronic stent integrated with therapeutic nanoparticles for endovascular diseases, ACS Nano 9 (2015), No. 6, 5937-5946.
Twomey, K. and Marchesi, J. Swallowable capsule technology: current perspectives and future directions, Endoscopy 41 (2009), No. 04, 357-362. Abstract.
Veron, Baptiste et al., Advocacy for multi mobile coil magnetic manipulation in active digestive endoscopy, IEEE/RSJ International Conference on Intelligent Robots and Systemes, IROS'12, Oct. 2012 Algarve: Portugal (2012). 3 pages.
Waters B. H. et al., Powering a ventricular assist device (vad) with the free-range resonant electrical energy delivery (free-d) system, Proceedings of the IEEE 100 (2012), No. 1, 138-149.
Xin, Wenhui et al., Study of a wireless power transmission system for an active capsule endoscope, The International Journal of Medical Robotics and Computer Assisted Surgery (2010), 113-122.
International Search Report and Written Opinion issued by the International Searching Authority of the United States for PCT/US15/61648, dated May 26, 2016. 9 pages.

\* cited by examiner

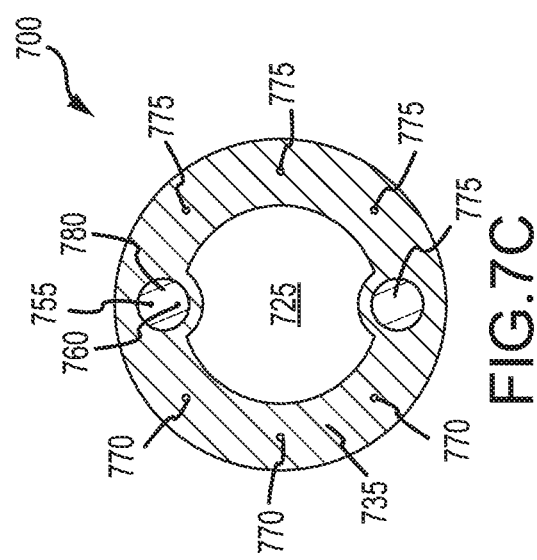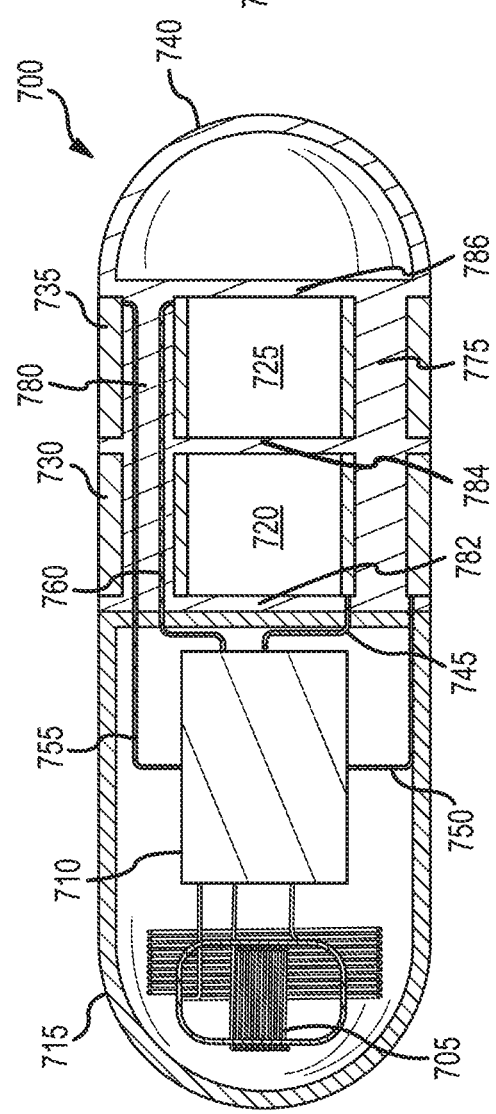

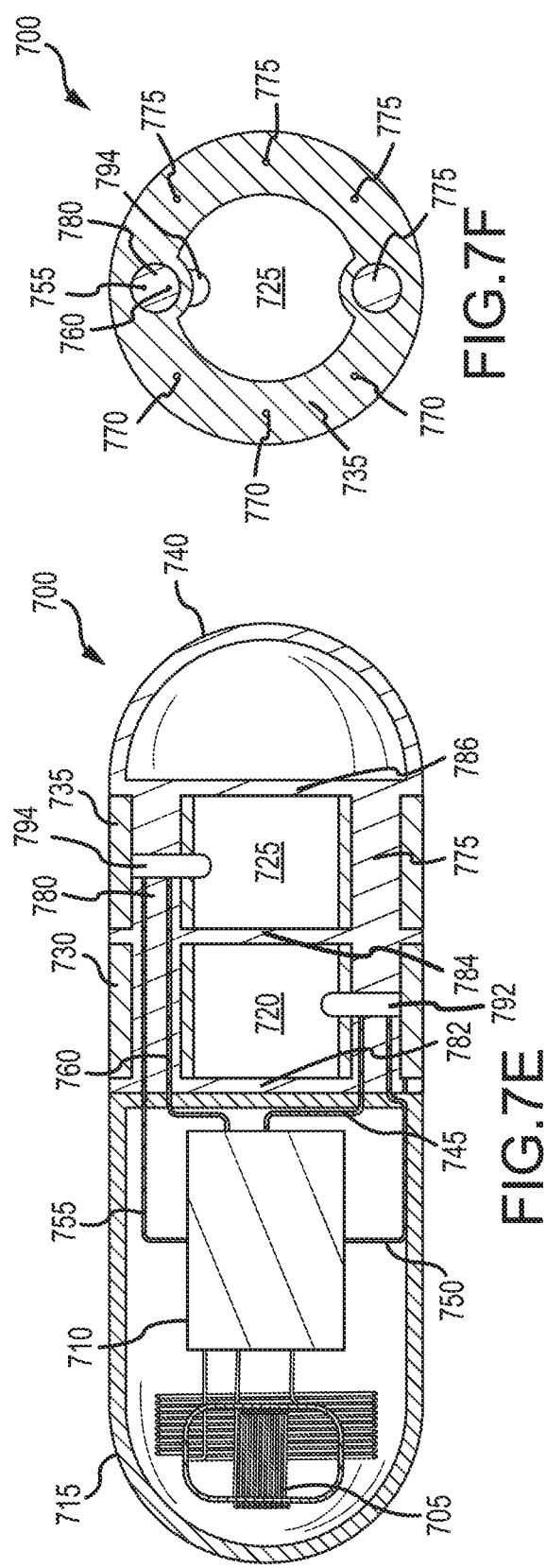

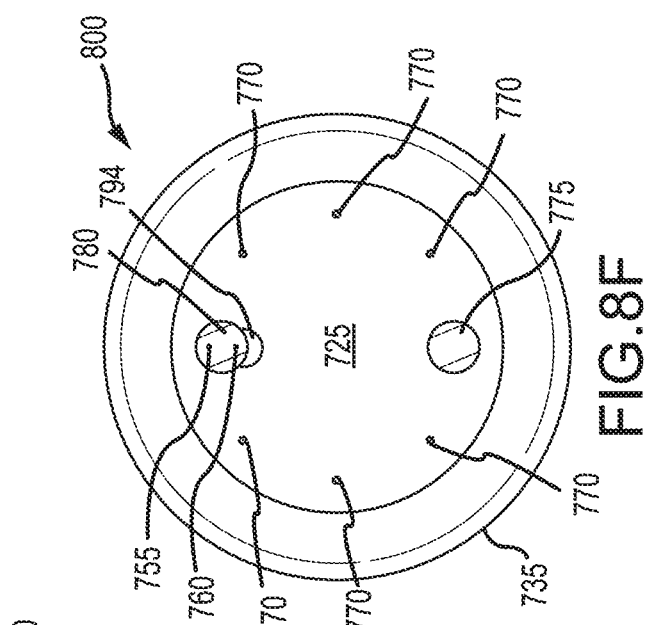
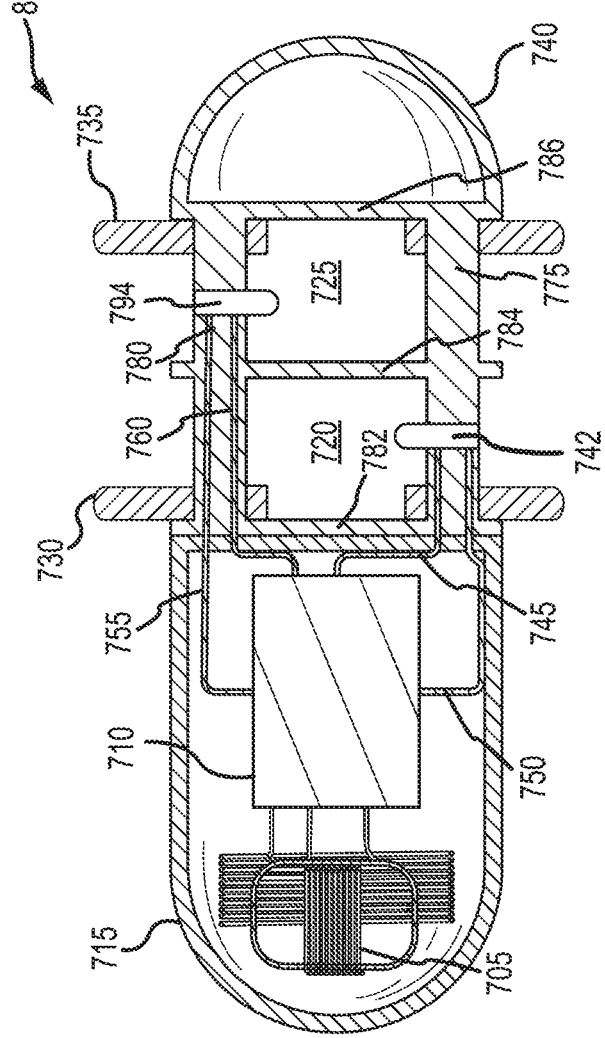
FIG.8F
FIG.8E

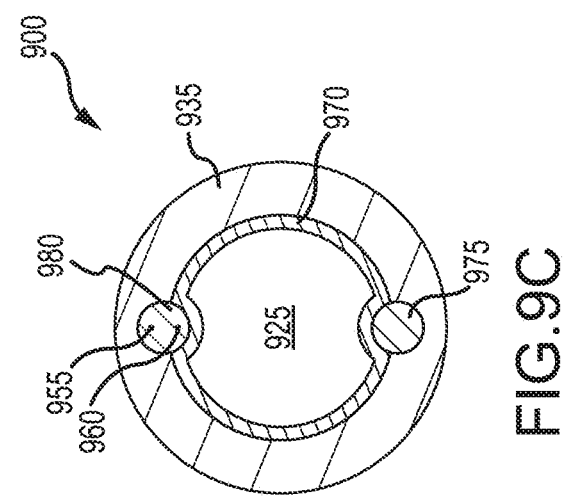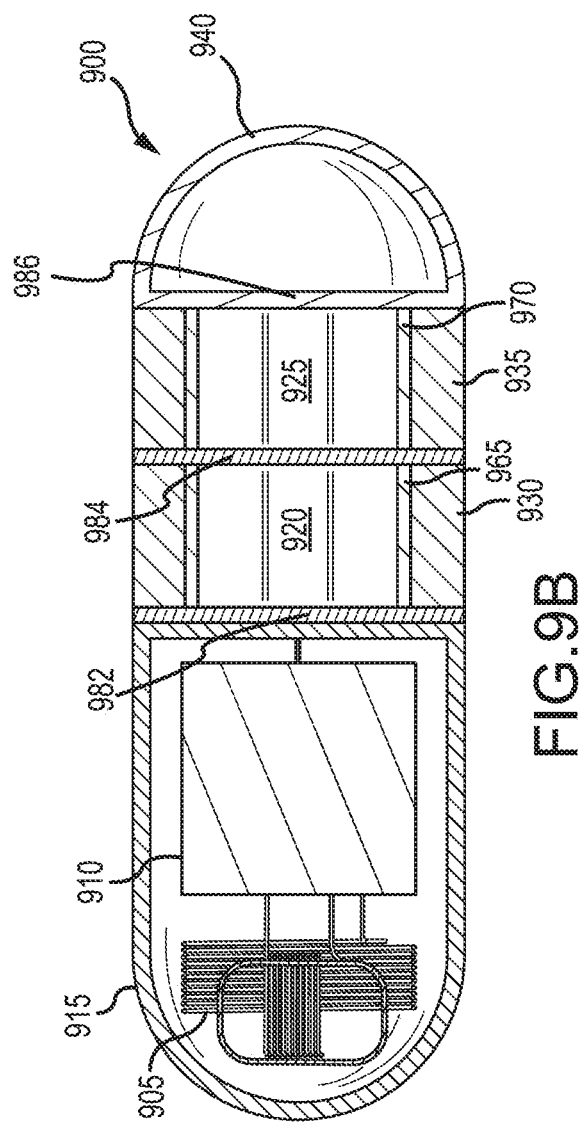

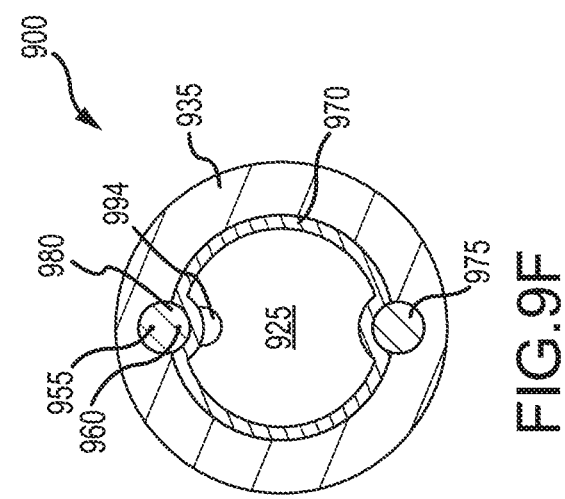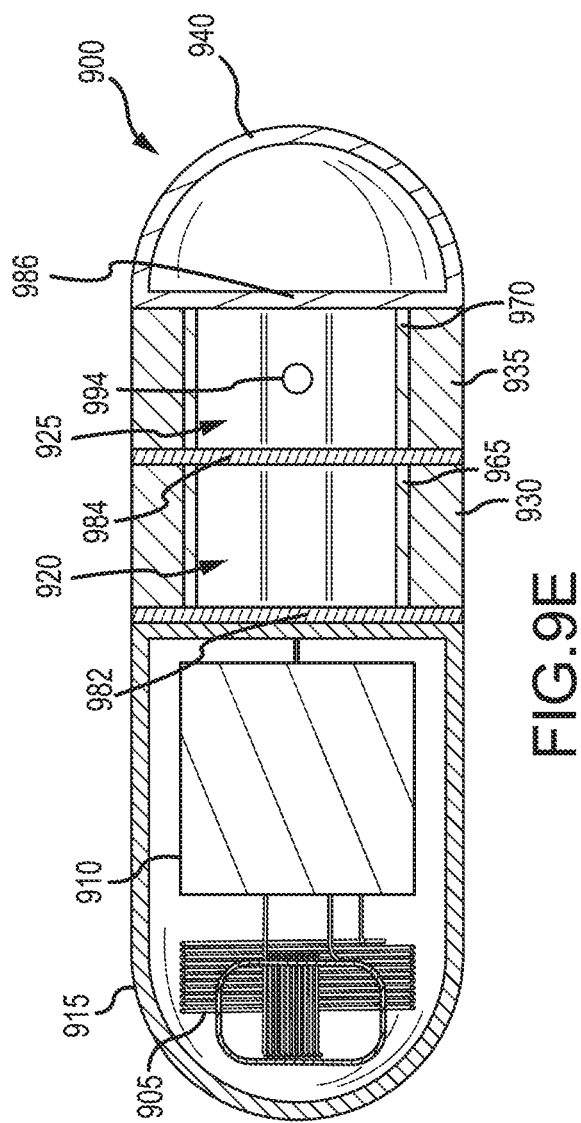

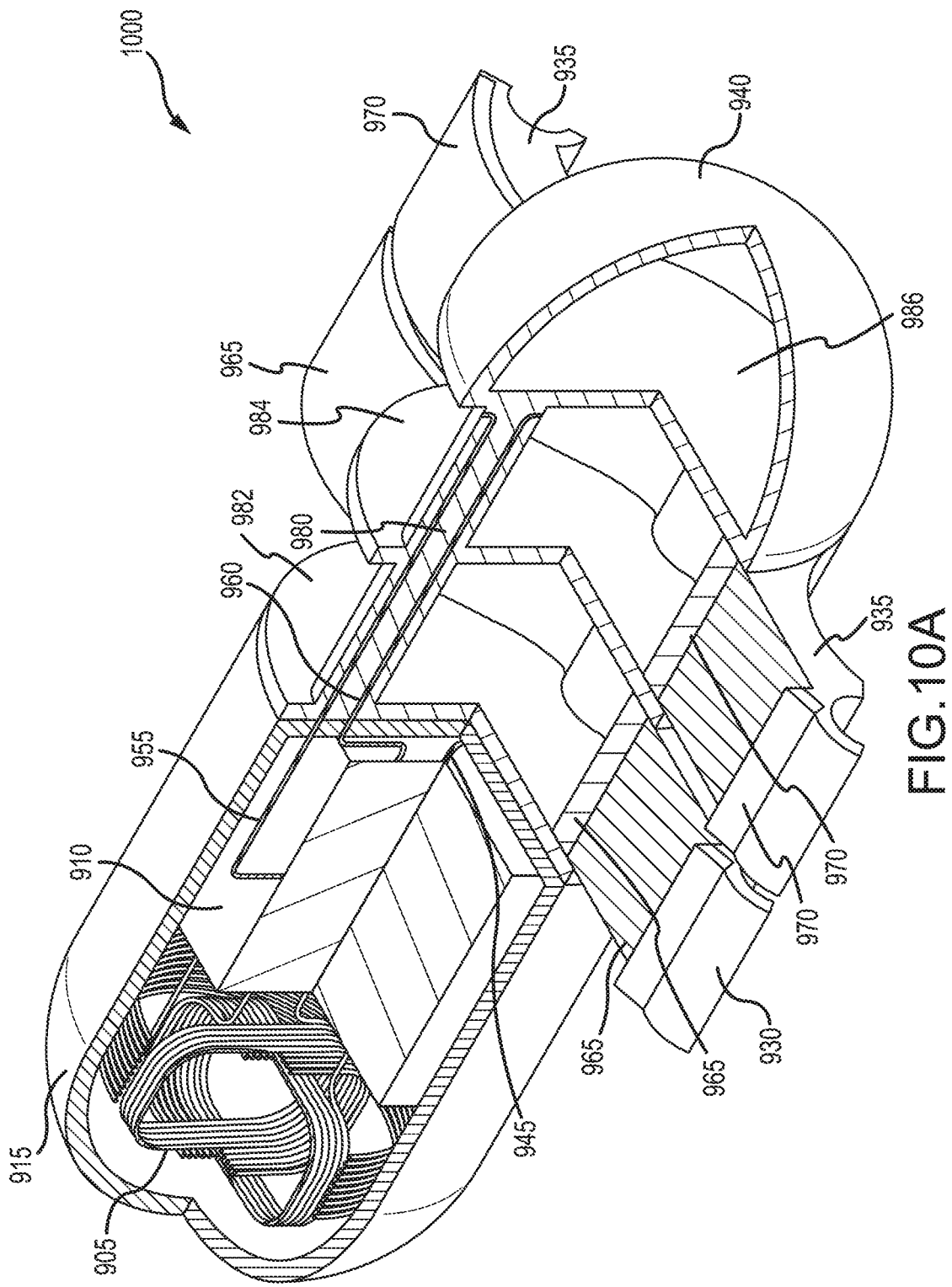

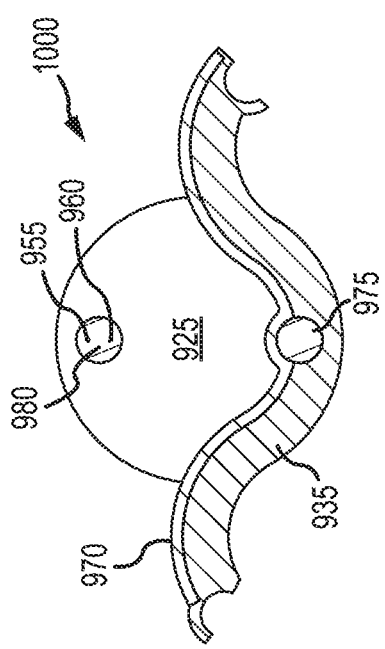
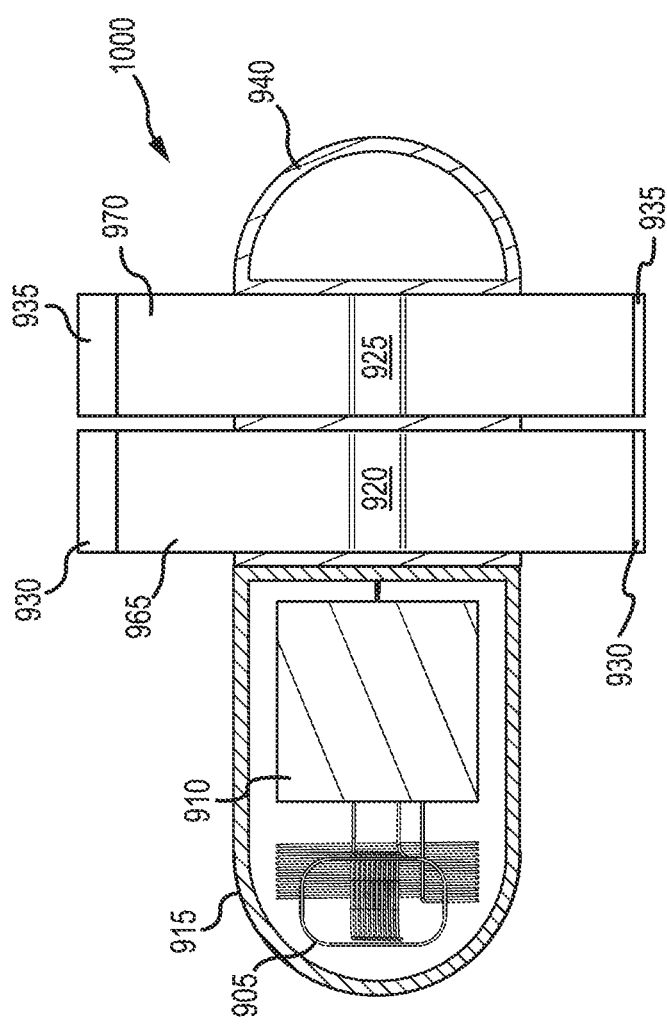

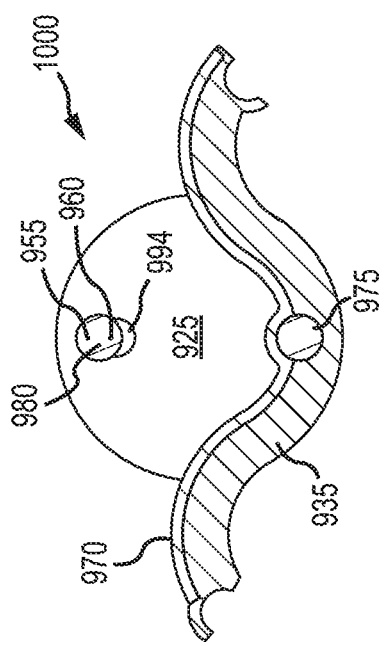
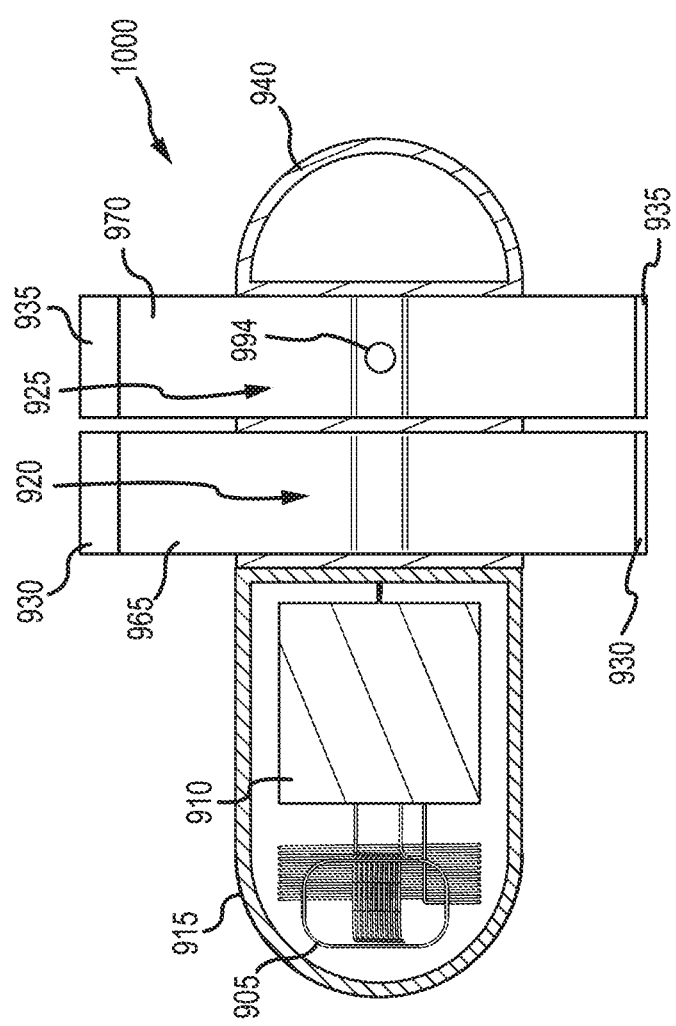
FIG.10F
FIG.10E

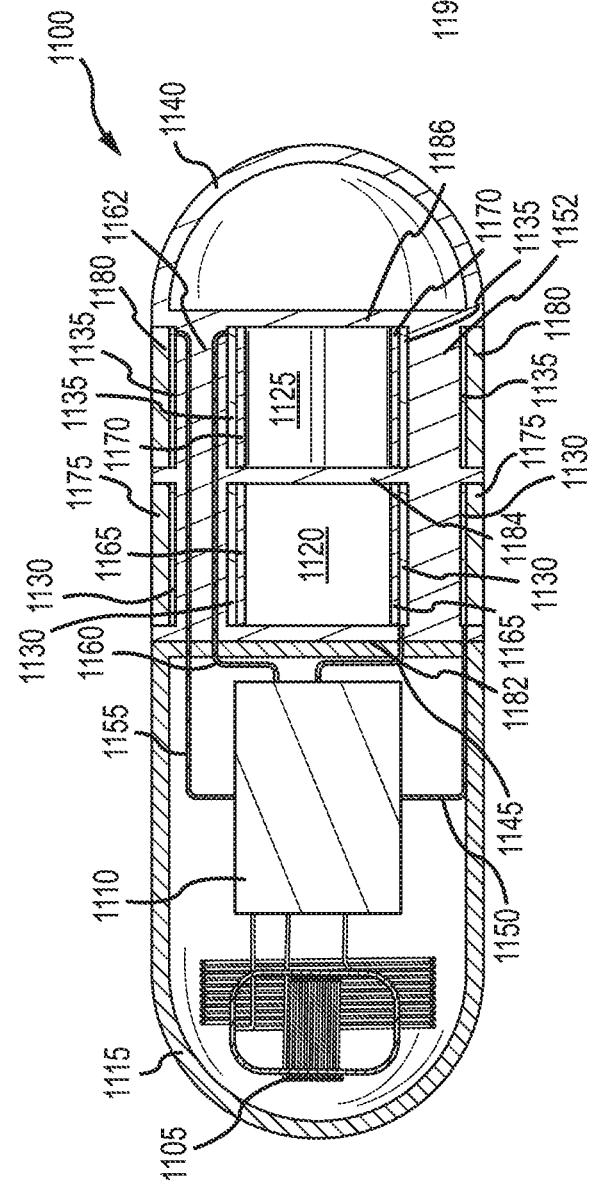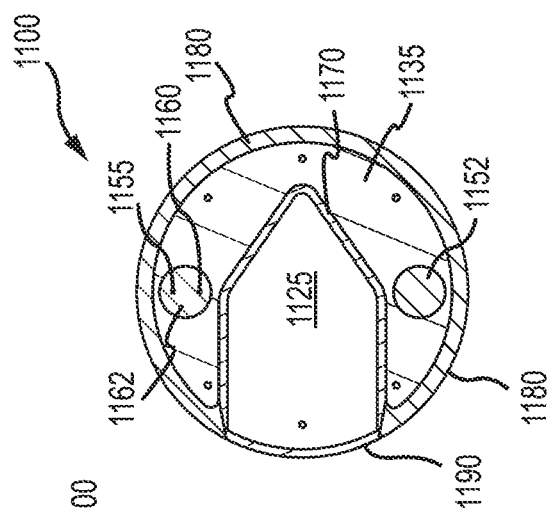

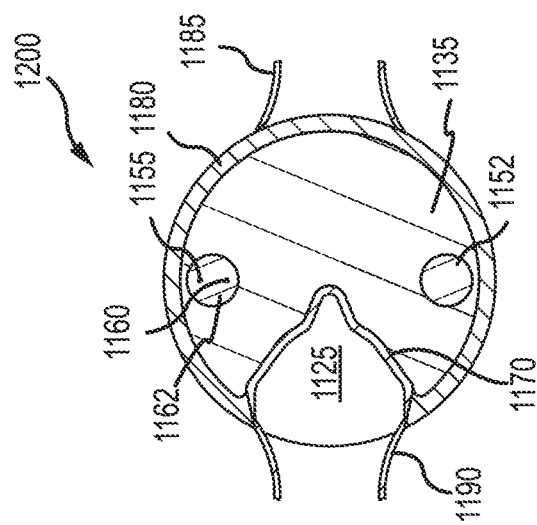
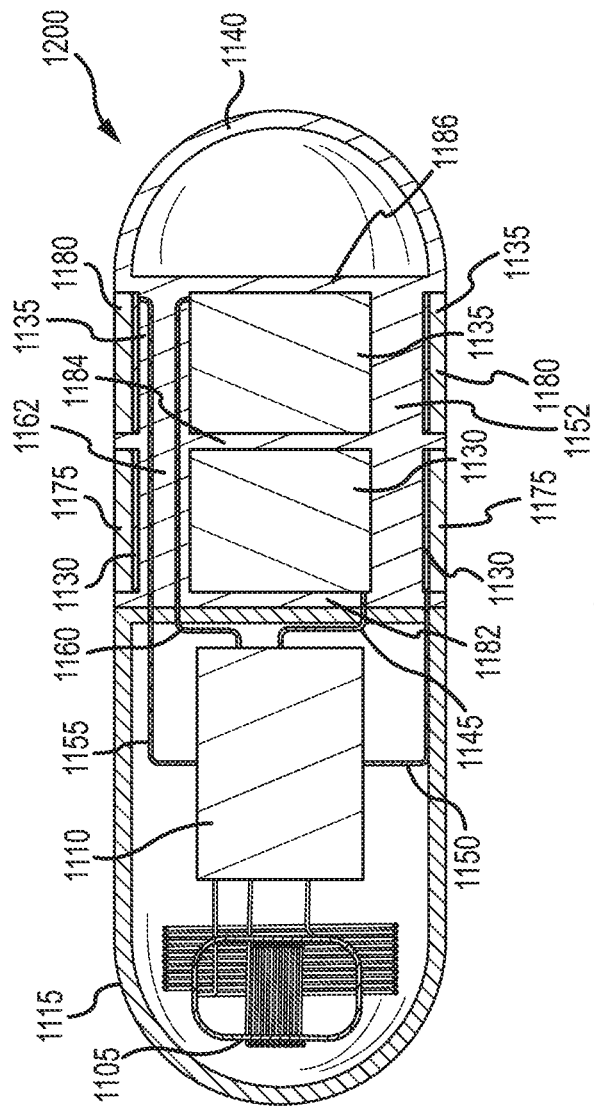

WIRELESS COMMUNICATIONS SYSTEM INTEGRATING ELECTRONICS INTO ORALLY INGESTIBLE PRODUCTS FOR CONTROLLED RELEASE OF ACTIVE INGREDIENTS

CROSS-REFERENCE TO RELATED APPLICATIONS

The present application is a continuation of U.S. patent application Ser. No. 15/668,487, filed Aug. 3, 2017, which is a continuation of U.S. patent application Ser. No. 14/946,478, filed Nov. 19, 2015, now U.S. Pat. No. 9,750,923, which claims priority to U.S. Provisional Patent Application Nos. 62/081,988, filed Nov. 19, 2014, 62/134,839, filed Mar. 18, 2015, and 62/191,149, filed Jul. 10, 2015, the entireties of which are hereby incorporated by reference.

BACKGROUND

Individuals in need of active ingredients for a desired biological response are generally required to ingest the active ingredients around the time at which the biological response is desired. For example, an athlete participating in a sporting event may require rehydration at some point during the event, and such rehydration can generally only be accomplished by consuming during the event a product that includes an active ingredient that can aid in rehydration (e.g., electrolytes). In many instances, the need to consume active ingredients during an event can be a competitive disadvantage, such as in situations where the athlete needs to physically slow down or completely stop in order to consume the desired active ingredient.

U.S. Pat. Nos. 8,449,920, 8,518,448, and 8,545,892 describe sustained-released beads that can be included in consumable products, such as foods or beverages. The sustained-released beads are consumed at, e.g., the beginning of an athletic event, and are designed to deliver an active ingredient over an extended period of time. In this manner, an athlete can consume an active ingredient once (e.g., before an athletic event begins) but still be provided with the active ingredient over the course of the event and without having to slow down or stop participation in the athletic event in order to consume additional active ingredient(s).

While useful in athletic competitions, the above-described sustained-release beads are not capable of providing precision, on-demand delivery of active ingredients. For example, if an athlete is participating in a bicycle race and desires a burst of caffeine as he or she approaches a steep climb, the athlete has no way to make the previously ingested sustained-release beads provide the active ingredient at the exact time the athlete begins his or her climb. Generally speaking, the rate at which the active ingredient is delivered to the athlete is outside of the athlete's control once the product is consumed. The sustained release beads can be designed to provide active ingredients at general time intervals, but various factors (e.g., the athlete's own physiology) will alter the timing at which the active ingredient is released, thereby making precision, on-demand delivery of an active ingredient during an event exceedingly difficult, if not impossible, to achieve.

SUMMARY

The present disclosure is directed to a system including a consumable item, such as a capsule, having internal electronic components disposed therein that can be used to provide on demand delivery of an active ingredient also included within the consumable capsule. In some embodiments, the consumable capsule will be in the form of a bead, capsule, tablet, or the like, and will include one or more active ingredients and internal electronic components that are capable of wirelessly receiving electrical power and/or command signals from an external communication device or activation device that is also part of the system. When a signal is sent from the external communication device or activation device to the internal electronic components, a release action is initiated which results in the consumable capsule releasing the active ingredient. In this manner, on demand delivery of active ingredients to the consumer of the consumable capsule is possible.

Methods of and materials for making the consumable capsule described herein are also disclosed.

BRIEF DESCRIPTION OF THE DRAWINGS

FIGS. 7A-7C illustrate an example of an embodiment of a consumable capsule, in accordance with various aspects of the present disclosure.

FIGS. 7D-7F illustrate an example of an alternative embodiment of a consumable capsule, in accordance with various aspects of the present disclosure.

FIGS. 8D-8F illustrate an example of an alternative embodiment of the consumable capsule shown in FIGS. 7D-7F after the delivery compartments are opened, in accordance with various aspects of the present disclosure.

FIGS. 9A-9C illustrate an example of another embodiment of a consumable capsule, in accordance with various aspects of the present disclosure.

FIGS. 9D-9F illustrate an example of an alternative embodiment of a consumable capsule, in accordance with various aspects of the present disclosure.

FIGS. 10A-10C illustrate an example of an embodiment of the consumable capsule shown in FIGS. 9A-9C after the delivery compartments are opened, in accordance with various aspects of the present disclosure.

FIGS. 10D-10F illustrate an example of an alternative embodiment of the consumable capsule shown in FIGS. 9D-9F after the delivery compartments are opened, in accordance with various aspects of the present disclosure.

FIGS. 11A-11C illustrate an example of still another embodiment of a consumable capsule, in accordance with various aspects of the present disclosure.

FIGS. 12A-12C illustrate an example of an embodiment of the consumable capsule shown in FIGS. 11A-11C after the delivery compartments are opened, in accordance with various aspects of the present disclosure.

DETAILED DESCRIPTION

Embodiments described herein are generally directed to orally ingestible delivery systems including internal electronic components (e.g., a receiver) and one or more active ingredients incorporated into a consumable item such as a capsule, wherein all of the components of the consumable capsule are safe for consumption by a mammal, such as a human. Another component of the system can include activation device (such as one incorporated into a wearable item) or an external communication device that is used by the consumer to communicate with the internal electronic components in the consumable capsule after consumption of the consumable capsule.

The consumable capsule can be provided in any form generally suitable for consumption by a user and which is capable of housing the internal electronic components. In some embodiments, the consumable capsule is in the form of a product that can be swallowed by a consumer without having to chew or break up the consumable capsule prior to being swallowed. Providing a consumable capsule that can be swallowed whole protects the internal electronic components included in the consumable capsule. In some embodiments, the consumable matrix may be in the form of a capsule, tablet, pill, or bead (e.g., a microbead). In some embodiments, the consumable capsule may be dispersed within a food or beverage and provided with a coating or other barrier that prevents the consumable capsule from breaking down while stored in the food or beverage.

The consumable capsule generally includes two primary components: the internal electronic components that allow the consumable capsule to receive signals and/or power from an external communication device or activation device, and one or more active ingredients. Other components that can be included in the consumable capsule will also be discussed.

Figure 1:
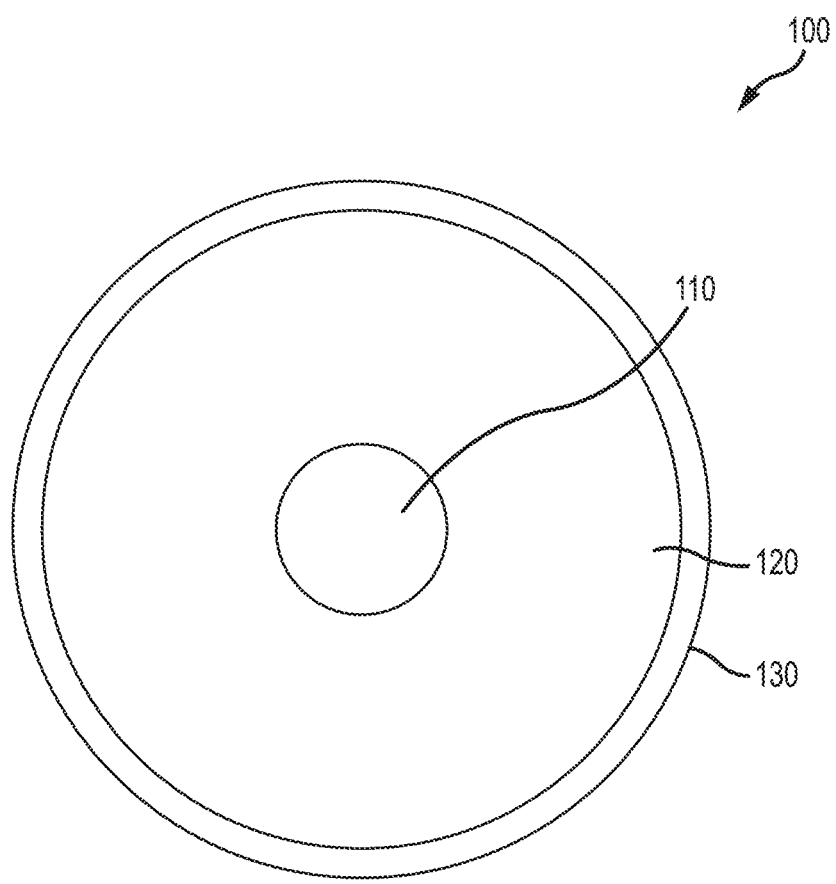
FIG. 1 diagrammatically represents an embodiment of a consumable capsule including active ingredients and internal electronic components according to some embodiments described herein.

FIG. 1 diagrammatically represents a consumable capsule 100 according to some embodiments described herein. The consumable capsule 100 includes internal electronic components 110 and active ingredients 120. The consumable capsule 100 can also include an optional coating layer 130. As shown in FIG. 1, the active ingredients 120 generally surround the internal electronic components 110, although other orientations are possible. The active ingredients 120 can also be mixed with other material (e.g., binding agent) to form the material surrounding the internal electronic components 110.

The internal electronic components included in the consumable capsule can be any electronic components that are safe for consumption. In some embodiments, the internal electronic components include at least a receiver capable of receiving a signal from an external communication device or activation device. In order to be safe for consumption, the internal electronic components should not include any material that is toxic to the consumer or that is included in an amount that is toxic to a consumer. In some embodiments, the internal electronic components are electronic components that have been approved for consumption by the U.S. Food and Drug Administration. The electronic components may be digestible, or may be designed to pass through the consumer.

In some embodiments, the electronic components may include one or more microcontrollers, microprocessors, and/or radio frequency identification (RFID) receiver capable of passing safely through the body. In some embodiments, the microcontrollers/microprocessors/RFID receiver include materials such as silicon, magnesium, and copper, each of which is included in an amount that is not dangerous to a human consuming the microchip.

The electronic components may be capable of functioning to aid in accomplishing at least two primary objectives. First, the electronic components can function with the receiver to receive signals from an external communication device or activation device. In some embodiments, the electronic components function with an internal receiver only to receive a signal from one or more external transmitters (one way communication), while in other embodiments, the electronic components function together with an internal transmitter to both receive and transmit signals to and from one or more external transceivers (two way communication). Second, the electronic components can function to carry out or aid in carrying out the release activity that results in active ingredients being released from the consumable capsule and being made available to the consumer's GI tract. In some embodiments, the release activity carried out using the electronic components is carried out upon receipt of a signal from the external transmitter.

The electronic components may include memory sufficient to store a programming instructions that, when executed, allows the consumable capsule to receive and/or transmit signals (via interaction/association with an internal transceiver) and/or initiate and carry out a release activity (via interaction/association with components included in the consumable capsule to perform a release activity).

The ability of the electronic components to function with the internal transceiver to send and/or receive signals can be accomplished using any suitable wireless communication means. In some embodiments, the electronic components are designed to allow for communication between transmitters and receivers via RF signals, although other types of wireless communications are contemplated, such as RFID communications, Bluetooth communications, near field communications (NFC), optical communications, or the like. In some embodiments, the electronic components may be designed to allow for communication in sub 1 GHz Industrial-Scientific-Medical (ISM) frequency bands, such as 125 Khz, 1 Mhz, 13.56 Mhz, 433 Mhz, and 915 Mhz. Lower frequency bands may have better penetration of the body. In other embodiments, the electronic components may be designed to allow for communication using frequencies that are common to cellular devices, such that the external communication device may be a cellular device. Suitable frequencies include UMTS/HSDPA/HSUPA (850, 900, 1900, 2100 MHz), GSM/EDGE (850, 900, 1800, 1900 MHz), 2.4 GHz ISM (Channels 1-11), 5 GHz UNII-1 (Channels 36-48), 5 GHz UNII-2 (Channels 52-64), 5 GHz-2Ext (Channels 100-140), and 5 GHz UNII-3 (Channels 149-161).

The internal electronic components of the consumable capsule are capable of communicating with any variety of external communication device or activation device using the same communications protocol as the internal electronic components. In some embodiments, the external communication device may be a cellular device (e.g., cellular phone), a tablet computer, a personal digital assistant (PDA), a Bluetooth device, a Global Positioning Satellite (GPS) device, or the like.

The external communication device or activation device may include programmable software and a user interface that allows the user to initiate a signal to the consumable capsule. For example, when the external communication device is a smartphone, the smartphone may run appropriate software (such as via an app) that provides a user interface for initiating a signal to the consumable capsule.

Figure 2:
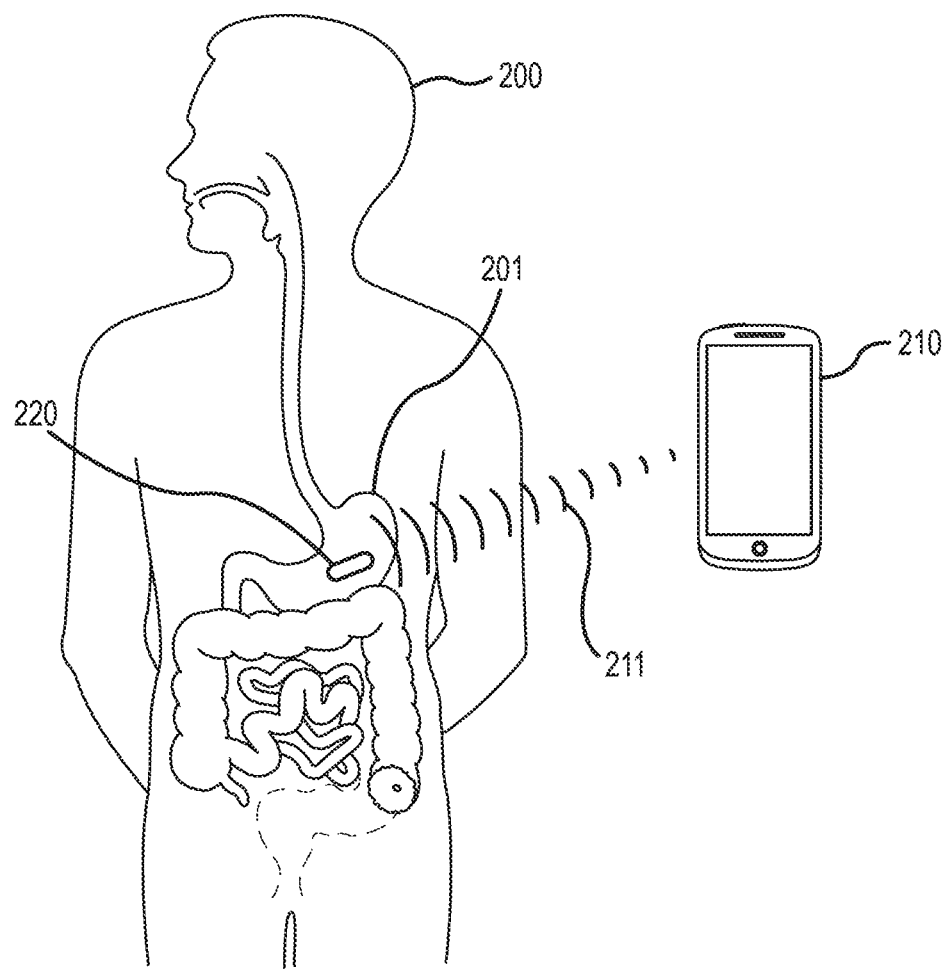
FIG. 2 diagrammatically represents an embodiment of a system in which an external communication device communicates with a consumable capsule ingested by a consumer to thereby release the active ingredient in the consumable capsule into the consumer's GI tract.

FIG. 2 diagrammatically represents an embodiment of a system in which an external communication device 210 communicates with a consumable capsule 220 ingested by a consumer 200. As shown in FIG. 2, the consumable capsule 220 is located in the consumer's GI tract 201, specifically the consumer's stomach, after being ingested by the consumer 200. The consumable capsule 220 is capable of residing in the consumer's GI tract 201 for a period of time during which the consumable capsule 220 significantly does not break down. An external communication device 210 is used to transmit a signal (or signals) 211 to the consumable capsule 220, and more specifically, to the internal electronic components (not shown) included within the consumable capsule 220. When the signal 211 is received by the consumable capsule 220, a release activity is initiated and carried out by the internal electronic components, which results in the release of the active ingredient included in the consumable capsule 220 into the consumer's GI tract 201. In some embodiments, the signal 211 may also provide power to the consumable capsule 220 to enable the release of the active ingredient. In a particular embodiment, the active ingredient is prevented from being released until the signal 211 is received by the consumable capsule 220, thereby allowing the consumer 200 to use the external communication device 210 to dictate more precisely when the active ingredient is made available for uptake by the consumer's GI tract.

In some embodiments, a secondary transceiver can be a part of the system including the external communication device and the internal electronic components of the consumable capsule. The secondary transceiver may be used as an intermediate communications relay between the internal electronic components and the external communication device, and may include additional and/or more versatile electronic components that relay messages between the internal electronic components and the external communication device. In one example, the secondary transceiver is provided primarily as a way to receive a signal from the external communication device, optionally process the signal information in some way, and relay the information to the consumable capsule. The secondary transceiver may solve the issue of the internal electronic components in the consumable capsule only being capable of sending or receiving certain types of information small distances due to the size and relative simplicity of the internal electronic components.

The secondary transceiver may be included within an activation device that is worn somewhere on the body of the user (i.e., a wearable item) so as to always stay relatively close to the consumable capsule. In some embodiments, the activation device is a patch or belt worn on the body. The size of the secondary transceiver within the activation device is generally substantially larger than the internal electronic components of the consumable capsule and can therefore include a more complex system that is capable of carrying out more functions than the internal electronic components in the consumable capsule. In one specific example, the secondary transceiver is capable of relaying a signal across a larger distance than is possible with the internal electronic components of the consumable capsule, which thereby allows the external communication device to be farther away from the user while still allowing for communication between the external communication device, the secondary transceiver, and the consumable capsule.

Figure 3:
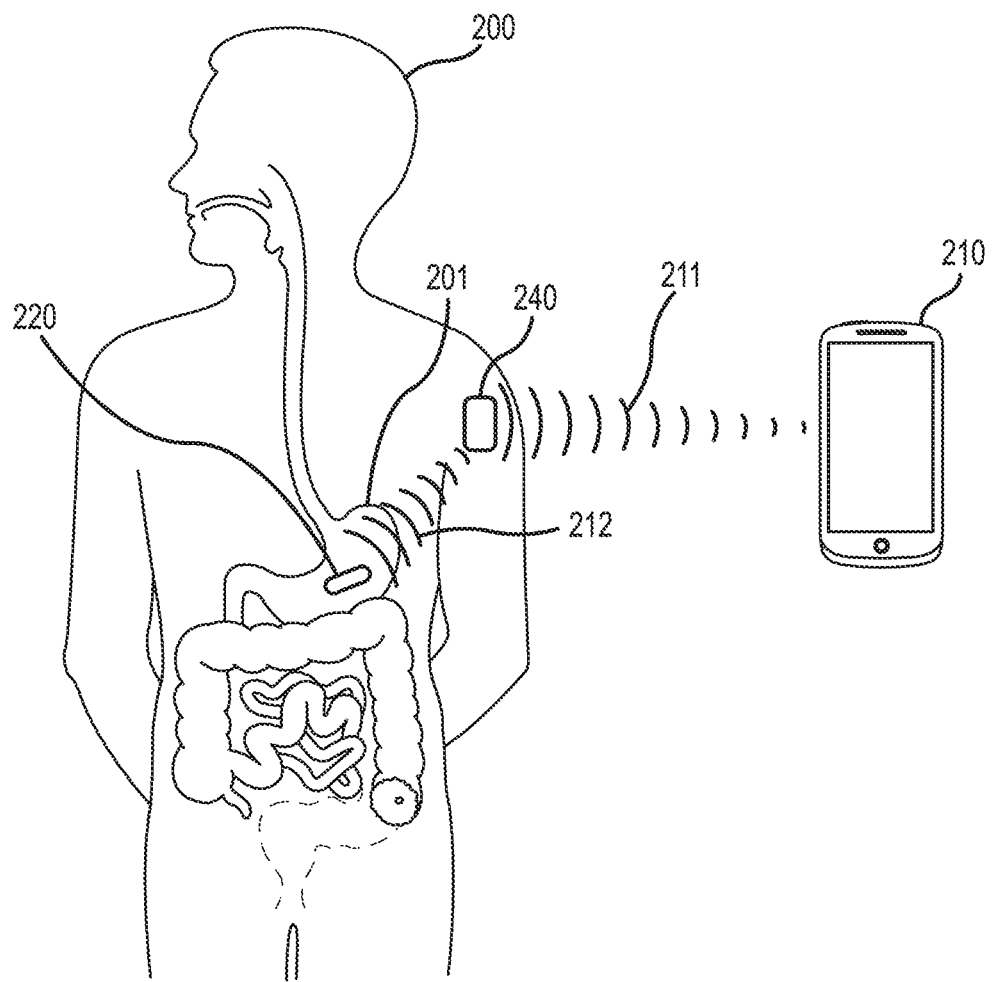
FIG. 3 diagrammatically represents an embodiment of a system in which an external communication device communicates with an activation device to release an active ingredient in a consumable capsule into the consumer's GI tract.

FIG. 3 diagrammatically represents an embodiment of a system using the secondary transceiver within an activation device described above. As shown in FIG. 3, the consumable capsule 220 is located in the consumer's GI tract 201 after being ingested by the consumer 200. The consumable capsule 220 is capable of residing in the consumer's GI tract 201 for a period of time during which the consumable capsule 220 does not significantly break down. An external communication device 210 is used to transmit a signal (or signals) 211 to activation device 240 positioned somewhere externally on the consumer's body. A secondary transceiver within the activation device 240 receives signal 211 and transmits a relay signal 212 to the consumable capsule 220, and more specifically, to the internal electronic components (not shown) included within the consumable capsule 220. When the relay signal 212 is received by the consumable capsule 220, a release activity is initiated and carried out, which results in the release of the active ingredient included in the consumable capsule 220 into the consumer's GI tract 201. In some embodiments, the signal 212 may also provide power to the consumable capsule 220 to enable the release of the active ingredient. In a particular embodiment, the active ingredient is prevented from releasing until the relay signal 212 is received by the consumable capsule 220, thereby allowing the consumer 200 to use the external communication device 210 and the secondary transceiver within the activation device 240 to dictate exactly when the active ingredient should be made available for uptake by the consumer's GI tract. The secondary transceiver can receive signals 211 from the external communication device 210 from a distance further away than if the external communication device 210 communicated directly with the consumable capsule 220.

As noted above, the system can be designed for one way or two way communication. In a one way communication system, the external communication device 210 is used exclusively to transmit signals to the activation device 240 and does not receive any information back from the consumable capsule 220 or activation device 240. Similarly, the internal electronic components in the consumable capsule 220 may be designed to only receive signals from the activation device 240. In other embodiments, each component of the system can send and receive information, allowing for a more diverse range of operations. In one example, where two way communication is provided, the internal electronic components or the consumable capsule 220 provide a signal to the external communication device 210 or activation device 240 including information relating to the state of the consumable capsule 220, e.g., whether the consumable capsule has released the active ingredient.

In some embodiments, the systems described above and illustrated in FIGS. 2 and 3 can be used in conjunction with an activation device 240 that is capable of monitoring one or more aspects of a user's health. In such embodiments, the activation device 240 monitors a user's health and notes when a condition arises requiring potential administration of an active ingredient. When such a condition arises and is noted by the activation device, the activation device can transmit a signal either directly to the consumable capsule to initiate the release of an active ingredient, or to the external communication device 210 such that the user or a person remotely monitoring the external communication device 210 can initiate the release of an active ingredient. The incorporation of an activation device 240 that is capable of health monitoring into the systems described herein can help to ensure the more accurate and timely release of active ingredients into a user's system.

In some embodiments, the external communication device 210 and/or activation device 240 may detect environment conditions and/or movement. For example, the external communication device 210 and/or activation device 240 may detect elevation, air temperature, movement speed, or other characteristics of the consumer 200 or consumer's environment. Based on this detection, the external communication device 210 and/or activation device 240 may automatically trigger the consumable capsule 220 to release an active ingredient. For example, the external communication device 210 and/or activation device 240 may automatically trigger the release of an active ingredient when the consumer 200 passes a certain elevation, or when the air temperature drops below a certain level, or when the consumer 200 is moving above a certain speed. The conditions for automatically releasing the active ingredient may be set by the consumer 200. In some embodiments where a smartphone is used as the external communication device 210, the consumer 200 may set the conditions for automatically releasing the active ingredient using an application stored on external communication device 210.

Figure 4A:
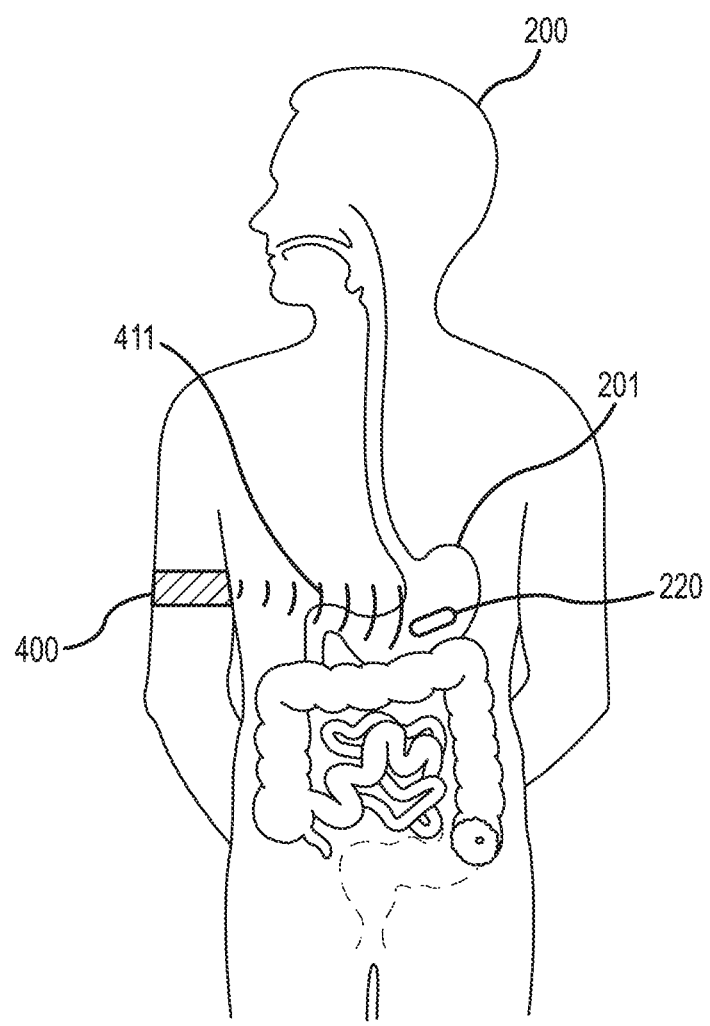
FIG. 4A diagrammatically represents an embodiment of a system in which an activation device (such as one incorporated into a wearable item) communicates with a consumable capsule ingested by a consumer to thereby release the active ingredient in the consumable capsule into the consumer's GI tract.

With reference to FIG. 4A, a diagrammatic representation of an embodiment of a system in which the consumer 200 wears activation device 400 is shown. The activation device 400 may be used to monitor one or more aspects of the consumer's health. As shown in FIG. 4A, the activation device 400 is a wearable item that is worn on the consumer's arm, but the location of the activation device 400 on the consumer 200 is generally not limited. Similarly, the aspect of the consumer's health that is monitored by the activation device 400 is also not limited.

When the activation device 400 monitors a condition in the consumer's health requiring an active ingredient, a signal (or signals) 411 may be sent directly to the consumable capsule 220 already ingested by the consumer 200. Receipt of the signal 411 triggers the consumable capsule 220 to carry out an event that results in the release of active ingredient into the consumer's GI tract 201. In some embodiments, the signal 411 may also provide power to the consumable capsule 220 to enable the release of the active ingredient. In this manner, the system shown in FIG. 4 is well suited for timely and accurate release of active ingredients based on the specific response to a monitored health event.

When the activation device 400 sends a signal 411 directly to the consumable capsule 220, the activation device may incorporate some or all of the technology typically included in the external communication device 210 discussed above. As a result, in some embodiments, the activation device 400 may eliminate the need for an external communication device 210.

Figure 4B:
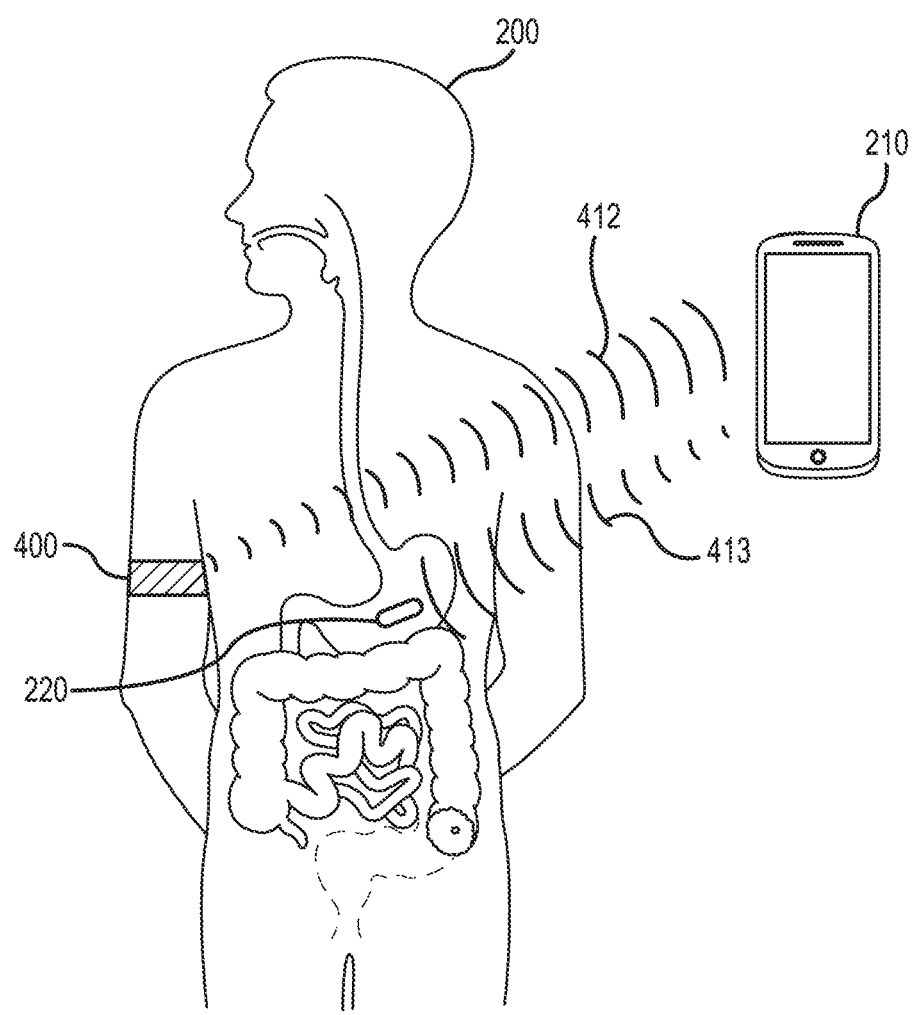
FIG. 4B diagrammatically represents an embodiment of a system in which an external communication device communicates with both an activation device (such as one incorporated into a wearable item) and a consumable capsule ingested by a consumer to thereby release the active ingredient in the consumable capsule into the consumer's GI tract.

With reference to FIG. 4B, a diagrammatic representation of an embodiment of a system in which the consumer 200 is again wearing activation device 400 is shown. However, in the embodiment illustrated in FIG. 4B, a signal (or signals) 412 is sent from the activation device 400 to the external communication device 210, which is then used to send a signal (or signals) 413 to the consumable capsule 220 and trigger the event that releases active ingredient into the GI tract of the consumer 200. In some embodiments, the signal 413 may also provide power to the consumable capsule 220 to enable the release of the active ingredient. As in FIG. 4A, the signal 412 is initiated when the activation device 400 measures a condition in the consumer's 200 health requiring an active ingredient. The signal 412 is received by the external communication device 210, which can then produce an alert describing the health event measured by the activation device 400. Either the consumer 200 or a person remotely monitoring the consumer 200 can review the alert and confirm whether the active ingredient should be released into the GI tract of the consumer 200. In this manner, the system incorporating both the activation device 400 and the external communication device 210 may be used to double check the measurements taken by the activation device 400 and provide the consumer or remote monitor (e.g., a doctor or health care professional) with the opportunity to confirm that the active ingredient should in fact be dispensed. This can reduce or eliminate erroneous distribution of active ingredient.

Once the health event measured by activation device 400 is confirmed, the consumer 200 or remote monitor can approve the dispensing of the active ingredient through a user interface of the external communication device 210, which in turn produces the signal 413 from the external communication device 210 to the consumable capsule 220.

The signal 413 and communication between the external communication device 210 and consumable capsule 200 can be similar or identical to the embodiments described above with respect to FIG. 2.

While not shown in FIG. 4B, the illustrated system can incorporate a secondary transceiver within the activation device 400 as described in reference to FIG. 3 so that the signal between the activation device 400 and the external communication device 210 can be relayed over longer distances than would be possible without the secondary transceiver. The secondary transceiver may be within a separate activation device from the activation device 400 and worn on a separate part of the body from the activation device 400, or the secondary transceiver may be incorporated into the activation device 400.

The activation device used in the embodiments described above is generally not limited and can be used to monitor one or more of any number of characteristics relating to a user's health. A wide variety of activation devices currently exist that are worn all over the human body to monitor any number of vital signs, health characteristics, and the like. Examples include, but are not limited to, headsets that measure brainwaves, glucose monitors, ECG monitors, pulse oximeters, blood pressure monitors, temperature monitors, EKG monitors, EGG monitors, EMG monitors, heart activity monitors, skin moisture monitors, breathing monitors, swelling monitors, and cardiac monitors.

Figure 5A:
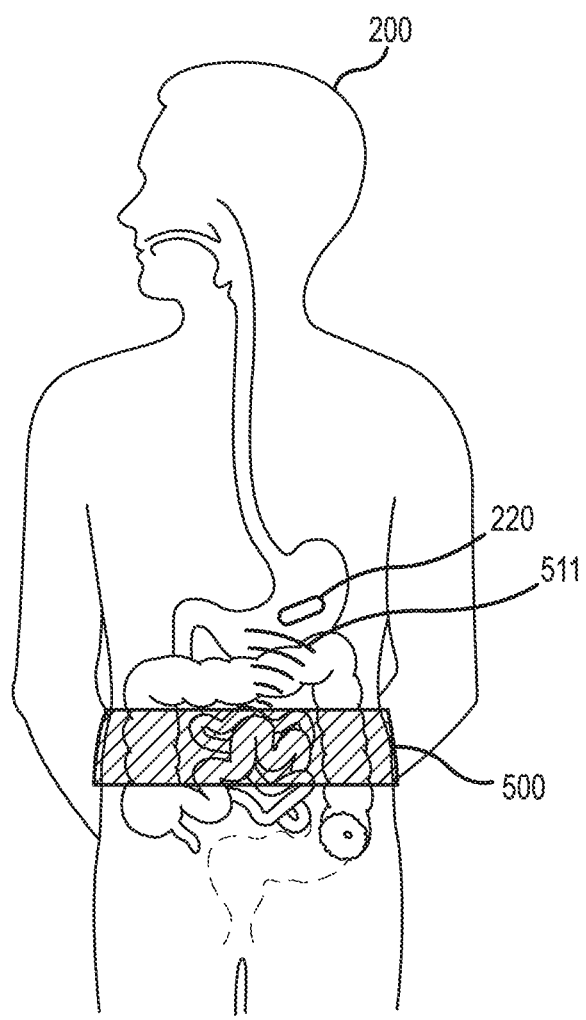
FIG. 5A diagrammatically represents another embodiment of a system in which an activation device (such as one incorporated into a wearable item) communicates with a consumable capsule ingested by a consumer to thereby release the active ingredient in the consumable capsule into the consumer's GI tract.

With reference to FIG. 5A, a diagrammatic representation of an embodiment of a system in which the consumer 200 wears activation device 500 around the consumer's abdomen or chest is shown. In some examples, the activation device 500 may be incorporated into a belt, pants, or shirt that is worn around the consumer's abdomen. The activation device 500 may include a coil of wire that generates an electromagnetic signal 511 that provides power to the consumable capsule 220 and triggers the release of the active ingredient into the consumer's GI tract. By encircling the consumer's abdomen or chest, the electromagnetic signal 511 generated by the activation device 500 may transfer power to the consumable capsule 220 more efficiently. In addition, the electromagnetic signal 511 may reach a larger area of the consumer's GI tract. The activation device 500 may trigger the release of the active ingredient based on an input from the consumer 200, an input from a health provider, and/or based on one or more aspects of the consumer's health, as described in reference to FIGS. 1-4.

In some embodiments, the coil of wire included in the activation device 500 may be litz wire. The litz wire may provide reduced impedance and allow the electromagnetic signal 511 to be generated more efficiently. The activation device 500 may also include a power source, such as a battery, and a secondary transceiver for communicating with other devices (such as an external communication device 210). In addition, the activation device 500 may include geolocation technology (e.g., GPS) and/or health monitoring technology.

In some embodiments, the activation device 500 may provide telemetry as to the location of the consumable capsule 220 within the consumer's 200 GI tract. For example, the consumable capsule 220 may cause interference to an electromagnetic field generated by the activation device 500. The activation device 500 may then estimate the location of the consumable capsule 220 based at least in part on this interference. The release of the active ingredient may then be triggered by the activation device 500 when the consumable capsule 220 is in a particular portion of the GI tract.

In addition, the activation device 500 may detect that the active ingredient has been released by the consumable capsule 220 based on one or more characteristics of the consumable capsule 220. For example, the consumable capsule 220 may cause different amounts of interference to an electromagnetic field generated by the activation device 500 before and after the release of the active ingredient. Alternatively, the consumable capsule 220 may provide a feedback signal to the activation device 500 when the active ingredient is released. In some embodiments, the consumable capsule 220 may release more than one active ingredient, and/or multiple doses of an active ingredient. Thus, the consumable capsule 220 may cause different amounts of interference and/or different types feedback based on type and/or amount of active ingredient that was released.

In some embodiments, the activation device 500 may utilize one or two magnetic coils for generating the electromagnetic signal 511. Two coils may be configured in a Helmholtz arrangement and may provide an approximately uniform magnetic field between the two coils. However, this configuration may only be capable of producing a magnetic field along a single axis, and may require the consumable capsule 220 to incorporate three orthogonal receiving coils. This configuration may reduce the complexity of the activation device 500 at the expense of increasing the complexity of the consumable capsule 220.

Alternatively, a lower cost and lower complexity consumable capsule 220 may be used with an activation device 500 that incorporates an array of smaller coils. Each of the smaller coils may be independently controlled to produce a magnetic field with an arbitrary orientation and gradient. This multi-coil architecture may allow the consumable capsule 220 to respond to electromagnetic signals 511 in a single axis because the activation device 500 can continuously adjust its field generation to match the orientation of the consumable capsule 220.

A set of individual coils may be arranged in the activation device 500 such that six or more coils can operate concurrently to behave as a set of Helmholtz coils, or to generate a gradient with orientation, magnitude, and RF emissions suitable for interacting with the consumable capsule 220 in a variety of orientations. For example, one embodiment may include 8 or 12 coils circumscribing the consumer's body in a horizontal row. Three or four of these rows of coils may be stacked vertically along the body to cover a larger area of the consumer's GI tract. The coils may be circular, square, hexagonal, or other suitable shapes. The coils may be made of copper, aluminum, or other suitable conductors, and may be flexible wires or rigid wires. Flexible printed circuit board manufacturing techniques may be used to etch multiple coils onto a single substrate that may also contain the control and power electronics necessary to operate the activation device 500.

In order to effectively utilize the set of coils, the activation device 500 may be capable of sensing the approximate location and orientation of the consumable capsule 220. This location sensing may be implemented by scanning for the consumable capsule 220 by adjusting the field orientation until the activation device 500 is coupled with the consumable capsule 220. The location data that results from this scanning process may be used to control the delivery of a particular active agent or collection of a sample within the body, as needed by clinical applications. In some embodiments, the capsule localization process may be implemented such that the activation device 500 detects the electrical power absorbed by the consumable capsule 220. This technique may allow the activation device 500 to output a minimum amount of power necessary to satisfy the requirements of the consumable capsule 220. The reduction of output power may improve battery life and reduce RF emissions of the activation device 500. Minimizing RF emissions may be desirable for both reducing system heat and meeting US FCC and international regulations.

Figure 6A:
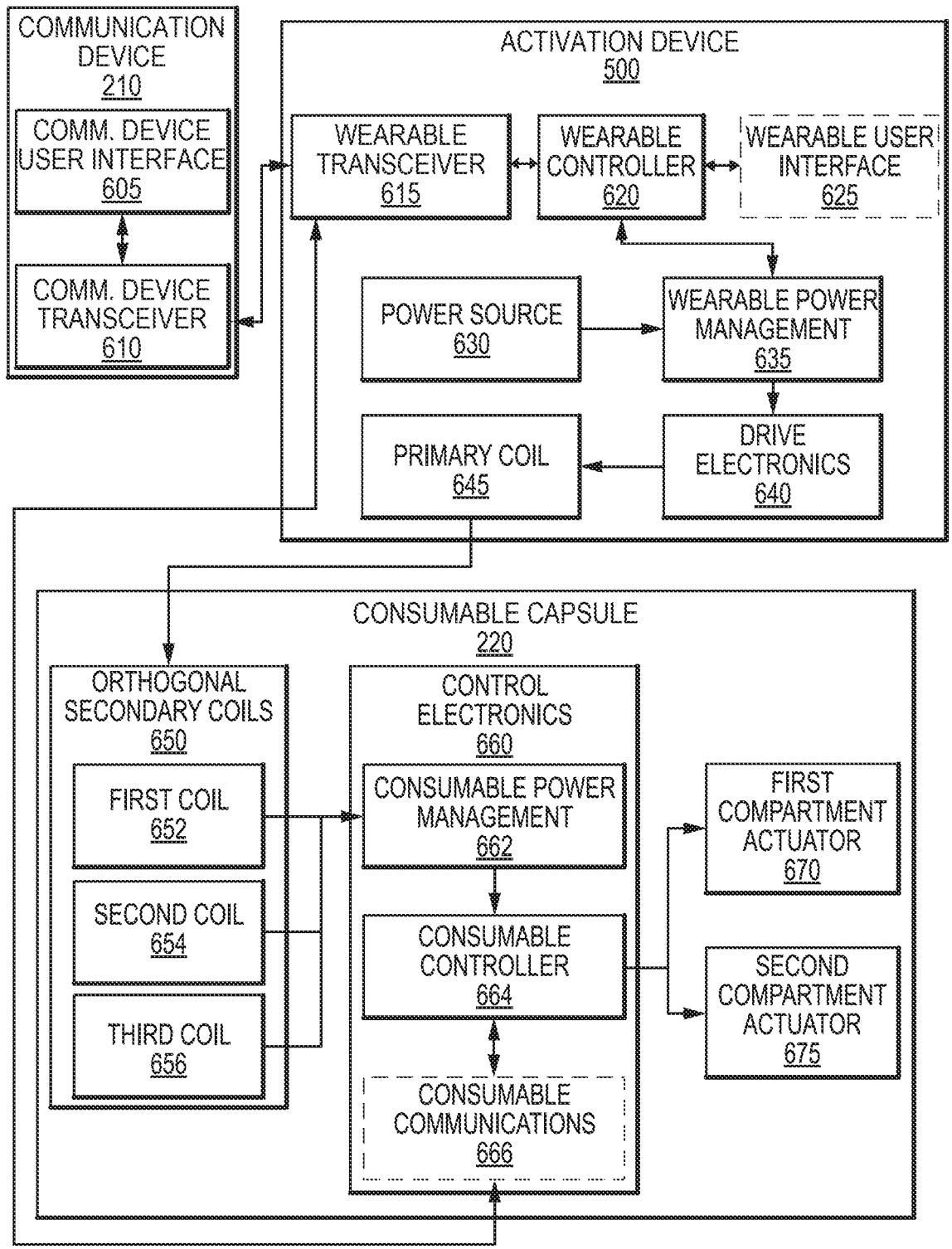
FIG. 6A diagrammatically represents an embodiment of a system for powering and triggering a consumable capsule.
Figure 6B:
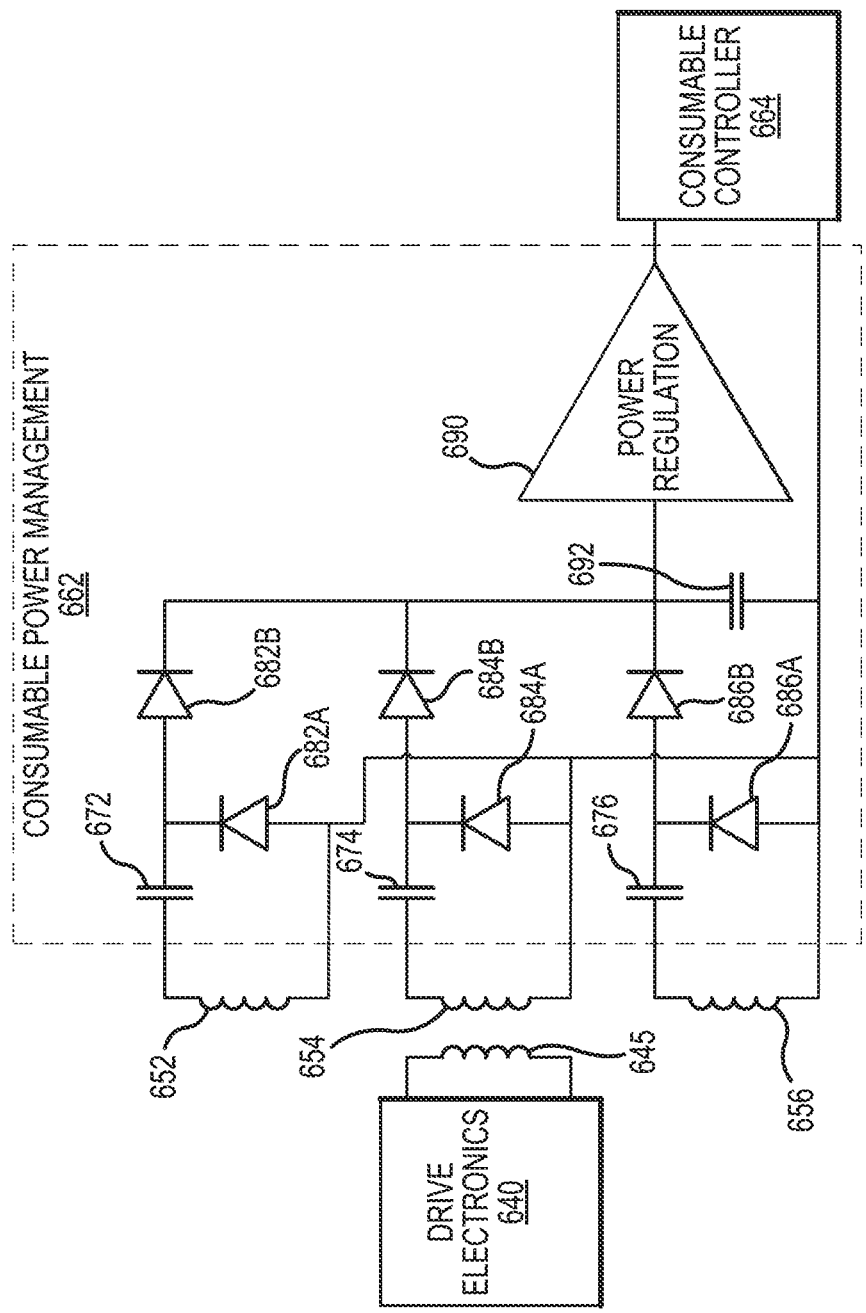
FIG. 6B diagrammatically represents an embodiment of the consumable capsule power management circuitry.
Figure 6C:
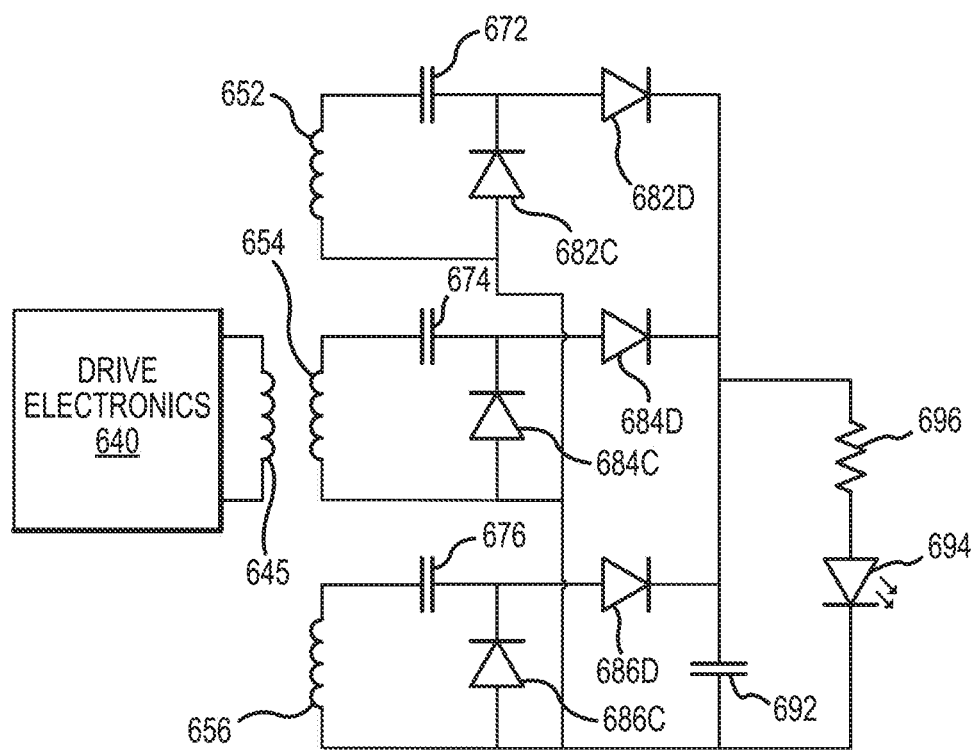
FIG. 6C diagrammatically represents an alternative embodiment of the electronics within the consumable capsule.

In some embodiments, the consumable capsule 220 may utilize one or more light emitting diodes (LEDs) (such as shown in FIG. 6C). In these embodiments, the detection of absorbed power may allow the activation device 500 to implement closed-loop control of the LED output. Implementing transmitter-side control of the capsule's light emissions may allow for precise activation of smart-polymer features such as valves, as further described herein.

In addition, an activation device 500 utilizing a set of coils may be capable of powering, controlling, and communicating with multiple capsules 220 within a consumer. For example, the activation device 500 may be configured to create a complex magnetic field geometry that satisfies the requirements of multiple capsules 220 simultaneously. Increasing the number of independent coils in the activation device 500 may improve the effectiveness of interacting with multiple capsules 220 by allowing for increasingly complex field geometries.

In some embodiments, an activation device 500 utilizing a set of coils may be designed to react in real-time to environmental magnetic disturbances, such as nearby metallic objects, or large or moving body tissues. If the activation device 500 is intended to be used in non-controlled environments such as an consumer's home, school, or workplace, environmental, magnetic disturbances may pose a risk to the proper functionality of the system. Real-time control of the magnetic field orientation and gradient may allow the multi-coil activation device 500 to function in environments where a single coil activation device, or an activation device having single set of Helmholtz coils would fail.

In some embodiments, an activation device 500 utilizing a set of coils may be used to control the movement of the consumable capsule 220. For example, the consumable capsule 220 may incorporate a permanent magnet or other means for locomotion driven by an external magnetic field.

Figure 5B:
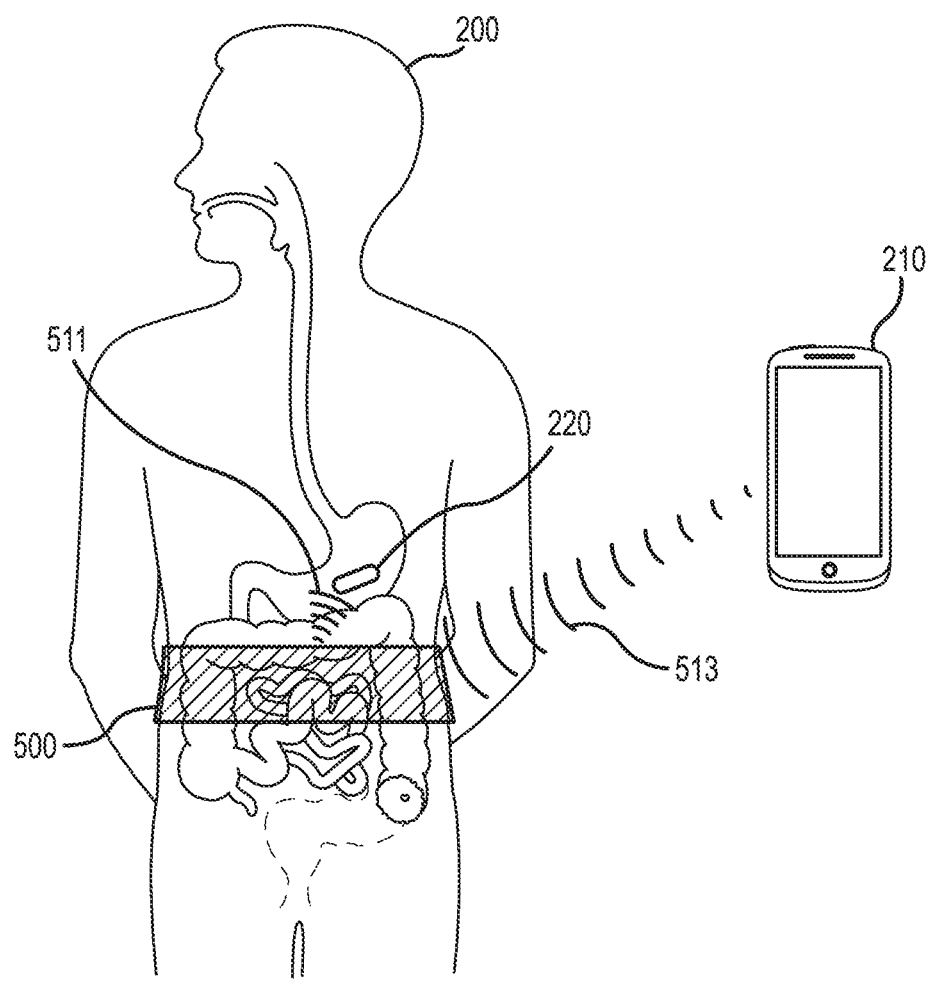
FIG. 5B diagrammatically represents another embodiment of a system in which an external communication device communicates with activation device (such as one incorporated into a wearable item) to release an active ingredient in a consumable capsule into the consumer's GI tract.

With reference to FIG. 5B, a diagrammatic representation is shown of an embodiment of a system in which the consumer 200 again wears activation device 500. However, in the embodiment in FIG. 5B, a signal (or signals) 513 is sent from an external communication device 210 to the activation device 500, which is then used to generate an electromagnetic signal 511. In one embodiment, the electromagnetic signal 511 provides power to the consumable capsule 220 and triggers the release of the active ingredient into the consumer's GI tract, as described in reference to FIG. 5A.

The activation device 500 may provide telemetry information to the external communication device 210 regarding the location of the consumable capsule within the consumer's GI tract. For example, the consumable capsule 220 may cause interference to an electromagnetic field generated by the activation device 500. The activation device 500 may estimate the location of the consumable capsule 220 based at least in part on this interference, and then report the estimated location to the external communication device 210. The external communication device 210 may then send the signal 511 to the activation device 500 based at least in part on the telemetry information.

In addition, the activation device 500 may detect that the active ingredient has been released by the consumable capsule 220 based on one or more characteristics of the consumable capsule 220. For example, the consumable capsule 220 may cause different amounts of interference to an electromagnetic field generated by the activation device 500 before and after the release of the active ingredient. Alternatively, the consumable capsule 220 may provide a feedback signal to the activation device 500 when the active ingredient is released. The activation device 500 may then send a notification to the external communication device 210 indicating that the active ingredient has been released. In some embodiments, the consumable capsule 220 may release more than one active ingredient, and/or multiple doses of an active ingredient. Thus, the notification from the activation device 500 may also indicate the type and amount of active ingredient that was released.

The activation device suitable for use in embodiments described herein can also include camera-based eyewear technology, such as Google glass and the like. This camera-based eyewear technology may be used to, for example, take pictures or video of a user's various body parts in order to make diagnosis for conditions that manifest themselves externally on a user's body.

The activation device suitable for use in embodiments described herein may be freestanding (worn over or under clothes) or can be incorporated into clothes.

Activation device may also include devices/technology which are incorporated into/onto a mobile phone, tablet, PDA, or the like. Any activation device that is incorporated onto or into a mobile phone, tablet, etc., can be used. Examples of activation devices that are incorporated onto or into a mobile phone, tablet, etc. include, but are not limited to, protective cases which can take the pulse of a user when his/her thumbs or fingers are placed on the protective case and software that utilizes a mobile phone's camera to conduct eye exams or other eye related diagnostic tests.

In some embodiments, the activation device may also include implantable devices in order to monitor vital signs and the like which cannot currently be monitored using external activation devices.

The consumable capsule further includes one or more active ingredients. Any active ingredient or combination of active ingredients can be included in the consumable capsule. In some embodiments, the active ingredients may include prescription pharmaceuticals, over-the-counter pharmaceuticals, veterinary pharmaceuticals, and/or other consumable products. Exemplary active ingredients include, but are not limited to, nutraceuticals, vitamins, supplements, minerals, enzymes, probiotics, bronchodilators, anabolic steroids, analeptics, analgesics, proteins, peptides, antibodies, vaccines, anesthetics, antacids, anti helmintics, anti-arrthymics, antibiotics, anticoagulants, anticolonergics, anti-convulsants, antidepressants, antidiabetics, antidiarrheals, anti-emetics, anti-epileptics, antihistamines, antihormones, antihypertensives, anti-inflammatories, antimuscarinics, antimycotics, antineoplastics, anti-obesity drugs, antiproto-zoals, antipsychotics, antispasmotics, anti-thrombics, antithyroid drugs, antitussives, antivirals, anxiolytics, astringents, beta-adrenergic receptor blocking drugs, bile acids, bronchospasmolytic drugs, calcium channel blockers, cardiac glycosides, contraceptives, corticosteriods, diagnostics, digestives, diuretics, dopaminergics, electrolytes, emetics, haemostatic drugs, hormones, hormone replacement therapy drugs, hypnotics, hypoglycemic drugs, immunosuppressants, impotence drugs, laxatives, lipid regulators, muscle relaxants, pain relievers, parasympathicolytics, parasympathicomimetics, prostagladins, psychostimulants, sedatives, sex steroids, spasmolytics, sulfonamides, sympathicolytics, sympathicomimetics, sympathomimetics, thyreomimetics, thyreostatic drugs, vasodialators, and xanthines; drugs or medicaments, breath fresheners, vitamins and other dietary supplements, minerals, caffeine, nicotine, fruit juices, and the like, and mixtures thereof. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra®, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocryptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

The consumable capsule may contain active ingredients having various types of payload form, such as powder, liquid, oil, slurry, micro-beads, nano-beads, etc. The active ingredients can be included in the consumable capsule in any desired quantity and in any desired combination. For example, the quantity of active ingredient contained in a consumable capsule may range from 0.1 mg to 500 g. However, the quantity may not be limited to these ranges.

In some embodiments, the consumable capsule may release more than one active ingredient, and/or multiple doses of an active ingredient.

The active ingredients selected for use in the consumable capsule can be used to address a variety of conditions. In some embodiments, the active ingredients are selected from those generally used to enhance physical performance, such as stimulants, electrolytes, vitamins, and minerals. In such embodiments, the consumable capsule matrix can be used to deliver any of the active ingredients on demand and in response to a specific event in an athletic competition (e.g., an on demand release of caffeine at the beginning of a steep climb in a bicycle race). In some embodiments, the active ingredients can be medicine needed to treat and/or prevent a variety of conditions. In a specific example, the active ingredients are selected to treat life threatening conditions, such as in a human having a high risk for heart attacks, in which case the consumable capsule can provide nitroglycerin on demand (and potentially by a remote user, such as a doctor, monitoring such a patient). In still another embodiment, the active ingredient can be any type of appetite suppressant such that the consumable capsule can be used by individuals trying to lose weight. In such embodiments, the consumable capsule can be used to deliver the appetite suppressant on demand, such as when the user feels a food craving.

In some embodiments, a user can consume multiple consumable capsules, with each consumable capsule having different active ingredients or combinations of active ingredients. Each consumable capsule can further include internal electronic components that transmit and/or receive specific signals different from the signals used in the other consumable capsule such that the active ingredients in each consumable capsule can be released separately and independently from active ingredients in the other consumable capsule. The user interface of the external communication device may be used to select which active ingredients to release. In a specific example, a first consumable capsule includes electrolytes and a second consumable capsule includes caffeine. In such an embodiment, the user may use the external communication device to release the caffeine when desired and the electrolytes when desired.

Other components that can be included in the consumable capsule include components which help to establish the form and/or stability of the consumable capsule, such as binding agents, coating materials, and shell layers. Any suitable binding agents, coating materials, and/or shell layers can be used to create a consumable capsule in which the internal electronic components and the active ingredients are embedded. The consumable capsule may be created in a range of sizes capable of being consumed by a human or other animal. For example, the length of the capsule may range from 1 mm to 10 cm, and the diameter may range from 1 mm to 5 cm. However, the consumable capsule may not be limited to these ranges.

In some embodiments, the binding agents, coating materials, shell layers, or the like are selected such that the internal electronic components can carry out a release activity which causes the binding agents, coating materials, shell layers, or the like to change in some way that allows the active ingredients to release into user. Any suitable release activity that results in the active ingredients being released from the consumable capsule into the consumer can be used to allow for the release of the active ingredients. In some embodiments, the release activity is a heating event which results in the binding agents, coating materials, etc., disintegrating, melting, or altering in some way that allows the active ingredients to release out of the consumable capsule. In other embodiments, the release activity is a vibrating or sonicating event that similarly causes a physical or structural break down in the consumable capsule to thereby release the active ingredients. Depending on the event to be initiated/carried out by the internal electronic components, the consumable capsule can include additional components necessary for carrying out the specific event (e.g., a heating element, a light generating element, or a vibrating element turned on and off by the electronic components upon receipt of a signal by the internal receiver).

With reference to FIG. 6A, an example of a consumable capsule 600 is shown, in accordance with various aspects of the present disclosure.

In some embodiments, the material used to create a consumable capsule in which the internal electronic components and active ingredients are enclosed is designed and/or selected such that the consumable capsule does not significantly break down upon exposure to the user's GI tract. In other words, the consumable capsule should not be permitted to significantly break down and release active ingredients into the user based on the conditions of the user's GI tract alone. The consumable capsule can therefore include coating layers and/or shells or the like which are not capable of breaking down when exposed to the environment of the user's GI tract, but which do break down upon the occurrence of the release activity initiated by the internal electronic components. Examples of specific materials and components are further described in reference to FIGS. 7A-12C.

With reference now to FIG. 6A, a diagrammatic representation of an embodiment of a system for powering and triggering a consumable capsule 220 is shown. The system includes an external communication device 210, activation device 500, and a consumable capsule 220.

The external communication device 210 may include a user interface 605. A consumer may input a command through the communication device user interface 605 for the consumable capsule 220 to release an active ingredient. The communication device user interface 605 may also include a display or other indicator that informs the consumer of the status of the consumable capsule 220. For example the communication device user interface 605 may provide an indicator when the active ingredient was successfully released from the consumable capsule 220.

When the communication device user interface 605 receives a command for the consumable capsule 220 to release an active ingredient, the communication device 210 may activate a communications module 610. The transceiver 610 transmits a signal (or signals) to the activation device 500. The transmitted signal instructs the activation device 500 to trigger the consumable capsule 220 to release the active ingredient. The signal may be transmitted using a wireless communication protocol, such as Bluetooth or Near Field Communication (NFC).

The activation device 500 includes a transceiver 615 for receiving the signal (or signals) from the external communication device 210. The received signal is passed to a controller module 620, which interprets the received signal and determines that an instruction to release the active ingredient was sent by the external communication device 210. In some embodiments, the activation device 500 may also include a user interface 625. The user interface 625 may include a display or indicator. The user interface 625 may indicate that an instruction to release the ingredient was successfully received. In some embodiments, the consumer inputs a command through the wearable user interface 625 for the consumable capsule 220 to release the active ingredient, instead of inputting the command through the external communication device 210.

The activation device 500 also includes a power source 630. The power source 630 may be a battery or other portable power source. The power source 630 provides power to the components of the activation device. In some embodiments, the power source 630 is also the source of power for the consumable capsule 220, as further described herein. A power management module 635 receives power from the power source and distributes the power to the components of the activation device 500.

When an instruction to release the active ingredient is received by the activation device 500, the controller module 620 configures the power management module 635 to supply power to drive electronics 640. The drive electronics 640 include electronic components (such as amplifiers and filters) that condition the power from the power management module 635. The conditioned power is then used to drive a transmitting element, such as primary coil 645. The primary coil 645 functions as an antenna to emit an electromagnetic signal at a frequency and amplitude capable of inductively coupling with orthogonal secondary coils 650 within the consumable capsule 220.

The orthogonal secondary coils 650 within the consumable capsule 220 include three coils 652, 654, 656 arranged at right angles to one another. Each of the antenna coils 652, 654, 656 is configured to receive electromagnetic energy from the electromagnetic signal emitted by the activation device 500. The respective amount of electromagnetic energy received by each of the coils 652, 654, 656 depends on the orientation of the consumable capsule 220 and distance from the primary coil 645. The orthogonal secondary coils 650 allow the consumable capsule 220 to efficiently receive the energy from the electromagnetic signal while the consumable capsule 220 is in a variety of orientations within a consumer's GI tract. For example, the coil 652, 654, or 656 having an orientation closest to the orientation of the primary coil 645 of the activation device 500 may receive a larger amount of electromagnetic energy than the other coils. Thus, the orthogonal secondary coils 650 allow the total amount of electromagnetic energy received by the consumable capsule 220 to be substantially independent of the orientation of the consumable capsule 220.

The electromagnetic energy received by each of the coils 652, 654, 656 may be used to provide power to the consumable capsule 220. For example, one or more of the coils 652, 654, 656 may generate low-level AC signals from the electromagnetic energy emitted by the primary coil 645 by inductively coupling with the primary coil 645. The size of the AC signals generated by each of the coils 652, 654, 656 may depend on the orientation of the consumable capsule 220 relative to the primary coil 645. Each of the AC signals generated by the coils 652, 654, 656 are transmitted to the consumable capsule's control electronics 660. The control electronics 660 include power management circuitry 662 which converts the AC signals from the coils 652, 654, 656 into a power source for the consumable capsule 220. For example, the power management circuitry 662 rectify, filter, and combine the low-level AC signals to produce a DC power source capable of powering the various functions of the consumable capsule 220 (as shown in FIG. 6B). Alternatively, the power management circuitry 662 may filter and combine the low-level AC signals to produce an AC power source. In this way, the orthogonal secondary coils 650 and power management circuitry 662 allow the consumable capsule 220 to be powered without the use of a potentially harmful chemical battery.

The consumable capsule's power management circuitry 662 provides power to a controller module 664. The controller module 664 may then trigger the release of an active ingredient by activating a first compartment actuator 670 and/or a second compartment actuator 675. When a compartment actuator is activated, an opening is created in the consumable capsule 220 which allows the active ingredient within a respective compartment to be released into a consumer's GI tract. The controller module 664 may be configured to activate the first and second compartment actuators 670, 675 sequentially or simultaneously. When activated sequentially, the controller module 664 may activate the second compartment actuator 675 automatically at a predetermined time after receiving the electromagnetic signal from the activation device's primary coil 645. Alternatively, the controller module 664 may activate the second compartment actuator 675 after receiving a secondary electromagnetic signal from the activation device's primary coil 645.

In some embodiments, the predetermined time for activating the second compartment actuator 675 may be configured by the consumer. For example, the consumable capsule 220 may include a communications module 666 which receives commands from the activation device transceiver 615 and/or from the communication device transceiver 610. Based on the received command, the controller module 664 may configure the predetermined time for activating the second compartment actuator 675. The communications module 666 may also be used for reporting the status of the consumable capsule 220 to the activation device 500 and/or the external communication device 210. For example, the controller module 664 may instruct the communications module 666 to transmit a feedback signal indicating each time a compartment actuator is successfully activated. The wearable transceiver 645 and/or communication device transceiver may receive the indicator, and then notify the consumer through the communication device user interface 605 and/or the wearable user interface 625.

Alternatively, in some embodiments, the activation device 500 may detect a compartment actuator was successfully activated through other characteristics of the consumable capsule 220. For example, when a compartment actuator is activated, the amount of interference the consumable capsule 220 causes to the electromagnetic field generated by the primary coil 645 may change. The drive electronics 640 may include circuitry for detecting this change in interference, which may then be reported to the wearable controller module 620. The wearable controller module 620 may then use the wearable user interface 625 to notify the user that the active ingredient was successfully released, or the wearable controller module 620 may send a notification signal to the external communication device 210.

With reference now to FIG. 6B, a diagrammatic representation of an embodiment of the consumable capsule power management circuitry 662 is shown. As described in reference to FIG. 6A, drive electronics 640 within the activation device provides power to the primary coil 645, which emits an electromagnetic signal. The primary coil 645 may inductively couple with one or more coils 652, 654, 656 based on the relative orientation of each coil and their distance from the primary coil 645. When the coils 652, 654, 656 inductively couple with the primary coil 645, the electromagnetic energy emitted by the primary coil 645 is converted into low-level AC signals by each of the coils 652, 654, 656. The low-level AC signal generated by the coil 652 is filtered and rectified by capacitor 672 and diodes 682A and 682B. The low-level AC signal generated by the coil 654 is filtered and rectified by capacitor 674 and diodes 684A and 684B, and the low-level AC signal generated by the coil 656 is filtered and rectified by capacitor 676 and diodes 686A and 686B. The filtered and rectified signals charge capacitor 692, which supplies a substantially DC signal to a power regulation circuit 690. The power regulation circuit 690 further smooths the DC signal and acts as a buffer between the power management circuitry 662 and the consumable capsule controller module 664. The DC signal from the power regulation circuit 690 is used by the controller module 664 to activate one or more compartment actuators within the consumable capsule. Alternatively, in some embodiments, the DC signal from the power regulation circuit may supplied directly to one or more compartment actuators or light emitting diodes (LEDs).

With reference now to FIG. 6C, a diagrammatic representation of an alternative embodiment of the electronics within the consumable capsule is shown. The components shown in FIG. 6C may be an example of the consumable capsule power management circuitry 662 described in reference to FIGS. 6A and 6B. As described in reference to FIGS. 6A and 6B, the drive electronics 640 of an activation device provide power to a primary coil 645, which emits an electromagnetic signal. The primary coil 645 may inductively couple with one or more of the coils 652, 654, 656 within the consumable capsule. When the coils 652, 654, 656 inductively couple with the primary coil 645, the electromagnetic energy emitted by the primary coil 645 is converted into low-level AC signals by each of the coils 652, 654, 656. The low-level AC signals generated by the coil 652 are filtered and rectified by capacitors 672, 674, 676 and diodes 682C, 682D, 684C, 684D, 686C, 686D. The rectified signal may then provide power to a light emitting diode (LED) 694 and/or other load 696 within the consumable capsule.

In some embodiments, the capacitors 672, 674, 676 may be in series with one or more inductors (not shown). Alternatively, in some embodiments, the capacitors 672, 674, 676 may be in parallel with one or more resistors or inductors (not shown). The combination of capacitors 672, 674, 676 with inductors may allow the consumable capsule to efficiently couple with the activation device when the activation device emits a signal within certain frequency bands. For example, the activation device may emit signals in the 125 Khz band and the 13.54 Mhz band (each being available for unlicensed medical operation by the FCC). Each frequency band may be associated with a different behavior of the consumable capsule. For example, a simple two-channel system might be implemented to open and close an actuator of the consumable capsule. The activation device may emit at a frequency band associated with opening the actuator, and emit at another frequency band associated with closing the actuator. The activation device may be designed such that the primary coil 645 is capable of emitting a signal at each frequency band, or the activation device may include multiple coils, each corresponding to a specific frequency band.

In addition to the LED 694, one or more of the diodes 682C, 682D, 684C, 684D, 686C, 686D shown in FIG. 6C may optionally also be LEDs. These LEDs may be selected to emit light at different wavelengths, and may be used to activate one or more compartment actuators of the consumable capsule. For example, different wavelengths may be associated with different compartments of the consumable capsule. Alternatively or in addition, certain wavelengths may be associated with opening a compartment actuator, while other certain wavelengths may be associated with closing a compartment actuator. Specific LEDs 682C, 682D, 684C, 684D, 686C, 686D may be activated based on the frequency of the electromagnetic signal emitted by the activation device, as described above. For example, LEDs 682C and 682D may be activated when the activation device emits a signal that couples with coil 652.

Inductive power coupling typically requires rectification circuitry which converts the AC power waveform from the resonant LC receiver circuit to DC power that can be used by the load. For example, FIG. 6B uses (non-LED) diodes to provide this rectification, but these diodes may add complexity to the system and may reduce power delivery efficiency due to energy lost as heat. The circuitry shown in FIG. 6C replaces the conventional diodes with LEDs 682C, 682D, 684C, 684D, 686C, 686D, and then uses the light emitted by the LEDs in the process of opening compartments of the consumable capsule. This approach allows some of the power that would have been wasted on the rectification stage to now perform useful work as emitted light. The total number of discrete components in the system may be thereby reduced.

Figure 7A:
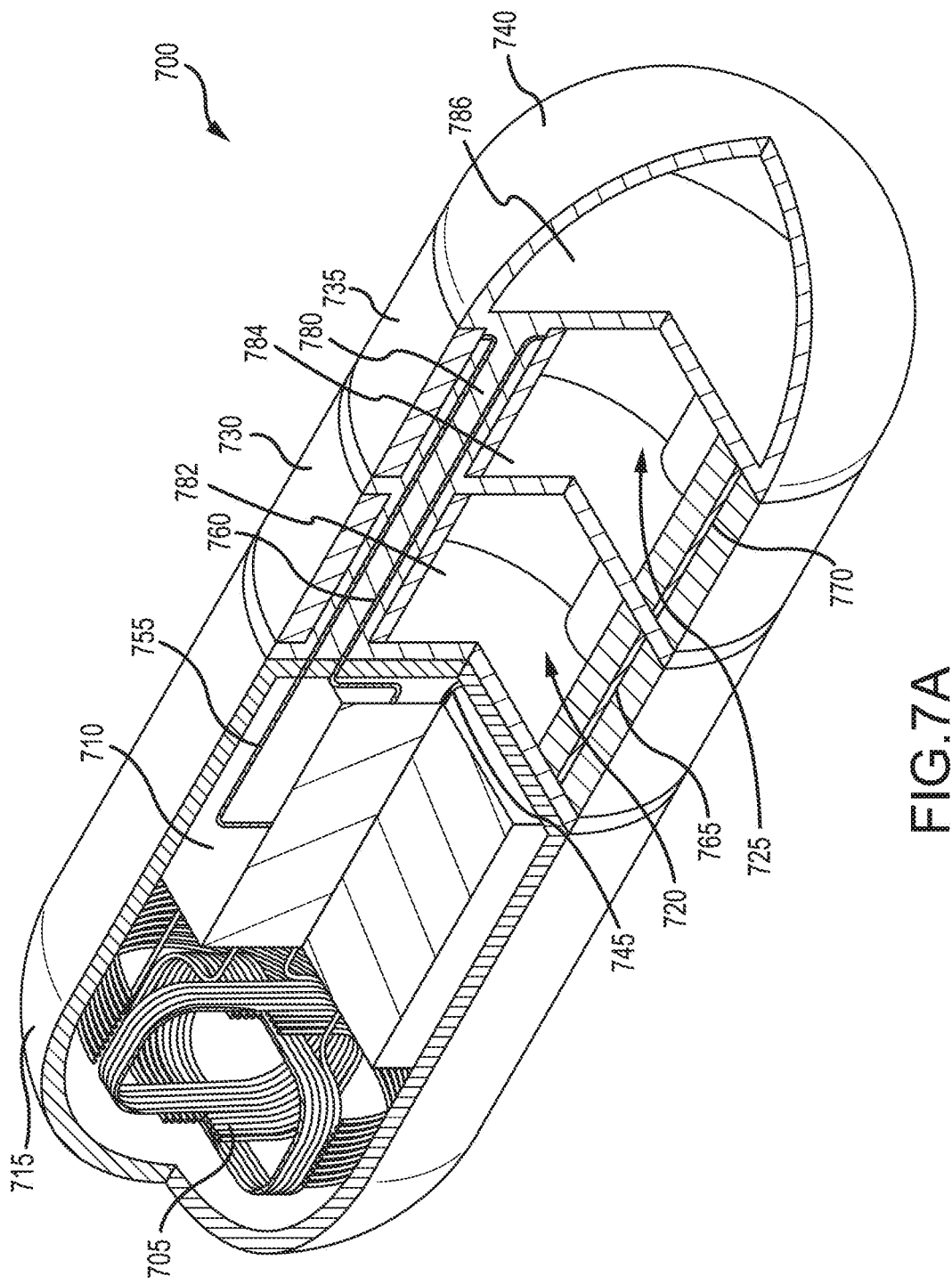

With reference now to FIG. 7A, a partial cross-sectional view illustrating an example of an embodiment of a consumable capsule 700 is shown, in accordance with various aspects of the present disclosure. FIGS. 7B and 7C further illustrate sectional views of the consumable capsule 700.

The consumable capsule 700 includes orthogonal secondary coils 705 and control electronics 710. The orthogonal secondary coils 705 and control electronics 710 are enclosed within an electronics section 715. The consumable capsule 700 also includes a compartment section 740 having a first delivery compartment 720 and a second delivery compartment 725. The first delivery compartment is formed by a first wall 782 and a second wall 784 of the compartment section 740. The first wall 782 and the second wall 784 are connected by a first primary support column 775 (shown in FIGS. 7B and 7C) and a second primary support column 780. The first delivery compartment 720 is sealed by a first linear actuator 730. Secondary support columns 765 embedded within the first linear actuator 730 provide further support between the first wall 782 and the second wall 784 of the compartment section 740.

The second delivery compartment 725 is formed by the second wall 784 and a third wall 786 of the compartment section 740. The first support column 775 (shown in FIGS. 7B and 7C) and the second support column 780 further connect the second wall 784 and the third wall 786. The second delivery compartment 725 is sealed by a second linear actuator 735. Secondary support columns 770 embedded within the second linear actuator 735 provide further support between the second wall 784 and the third wall 786 of the compartment section 740.

In some embodiments, the electronics section 715 and the compartment section 740 may be manufactured independently. The electronics section 715 may then be bonded to the first wall 782 of the compartment section 740 through various bonding techniques, such as sonic welding or with an adhesive. The electronics section 715 and the compartment section 740 may be made from the same or different materials. For example, the electronics section 715 may be made from an inert material that is not digestible (e.g., polyethylene), while the compartment section 740 may be made from a digestible material (e.g., polylactic-co-glycolic acid (PLGA)).

In other embodiments, the electronics section 715 and the compartment section 740 may be manufactured as a single structure from the same material, either inert or digestible.

Each delivery compartment 720 and 725 may include an active ingredient. While shown with two delivery compartments, one of ordinary skill would understand the consumable capsule 700 may be configured with a single delivery compartment, or three or more delivery compartments.

The orthogonal secondary coils 705 include three coils arranged orthogonally to one another. Each of the coils are configured to receive electromagnetic energy from a triggering device, such as the activation device described above.

The respective amount of electromagnetic energy received by each of the coils depends on the orientation of the consumable capsule 700. The orthogonal secondary coils 705 allows the consumable capsule to efficiently receive signals (such as an electromagnetic signal 511 from activation device 500, shown in FIGS. 5A and 5B) while the consumable capsule 700 is in a variety of orientations within a consumer's GI tract. For example, the activation device 500 may generate an electromagnetic signal 511 using a primary coil of wire. The coil of the orthogonal secondary coils 705 having an orientation closest to the orientation of the coil of the activation device may receive a larger amount of electromagnetic energy than the other coils. Thus, by including the three orthogonal coils in the orthogonal secondary coils 705, the total amount of electromagnetic energy received by the consumable capsule 700 may be substantially independent of the orientation of the consumable capsule 700.

The energy received by each of the coils of the orthogonal secondary coils 705 may be used to provide power to the consumable capsule 700. Control electronics 710 may combine the energy received by each of the coils and convert the total received energy into a power source, as described in reference to FIGS. 6A-6C. In this way, the orthogonal secondary coils 705 and control electronics 710 allow the consumable capsule 700 to generate power without the use of a potentially harmful chemical battery.

The control electronics 710 trigger the release of the active ingredient in the first delivery compartment 720 by applying an electric field to the first linear actuator 730. The control electronics 710 apply the electric field by transmitting an electric current over a first positive power line 745 and a first negative power line 750 (shown in FIG. 7B) to the first linear actuator 730. The first linear actuator 730 may include a stimuli responsive material such that when the electric field is applied to the first linear actuator 730, the actuator changes shape. When the first linear actuator 730 changes shape, an opening is created for the active ingredient within the first delivery compartment 720 to be released. The control electronics 710 trigger the release of the active ingredient in the second delivery compartment 730 in a similar way. The second linear actuator 735 may also include a stimuli responsive material and the control electronics 710 may apply an electric field to the second linear actuator 735 by transmitting an electric current over a second positive power line 755 and a second negative power line 760. The control electronics 710 may be configured to trigger the first and second delivery compartments sequentially or simultaneously, as described above.

The linear actuators 730 and 735 may be made partially or entirely from stimuli responsive materials, such as electro-active polymers (EAPs). In one embodiment, the EAPs include Inherently Conjugated Polymers (ICPs), such as Polypyrrole, Polyaniline, or Polythiopene. When a voltage potential is applied to an ICP, electrons begin moving between the electrodes in the polymer. The speed of this is driven by the surrounding electrolyte ionic conductivity. The movement of charge then attracts ions in the polymer to the electrodes, creating a redox reaction. Ions from the electrolyte diffuse into the polymer to balance the charge in the system, the speed of which is driven by the size of the ions and the structure of the polymer. In some examples, the digestive fluids within the GI tract may function as the electrolyte. The addition of these ions then generates a volume change in the polymer dependent on the modulus of the polymer. The volume change creates a geometric change which is dependent on the shape of the actuator and/or the materials to which the actuator is attached.

The components of the consumable capsule 700 may include bio-compatible components. For example, the components within the orthogonal secondary coils 705 and control electronics 710 may include conductors, semi-conductors, dielectric materials, and substrate materials. Bio-compatible conductors may be made from Magnesium or Magnesium alloy materials. Bio-compatible semi-conductors may be made from Indigoids, Magnesium Oxide, or doped Magnesium materials. Bio-compatible dielectrics may be made from nucleotides or DNA. Bio-compatible substrates may be made from Silk, PLGA, or Shellac. In addition to being bio-compatible, some of the components (such as those made from PLGA, Indigoids, and nucleotides) may be bio-resorbable.

Figure 7D:
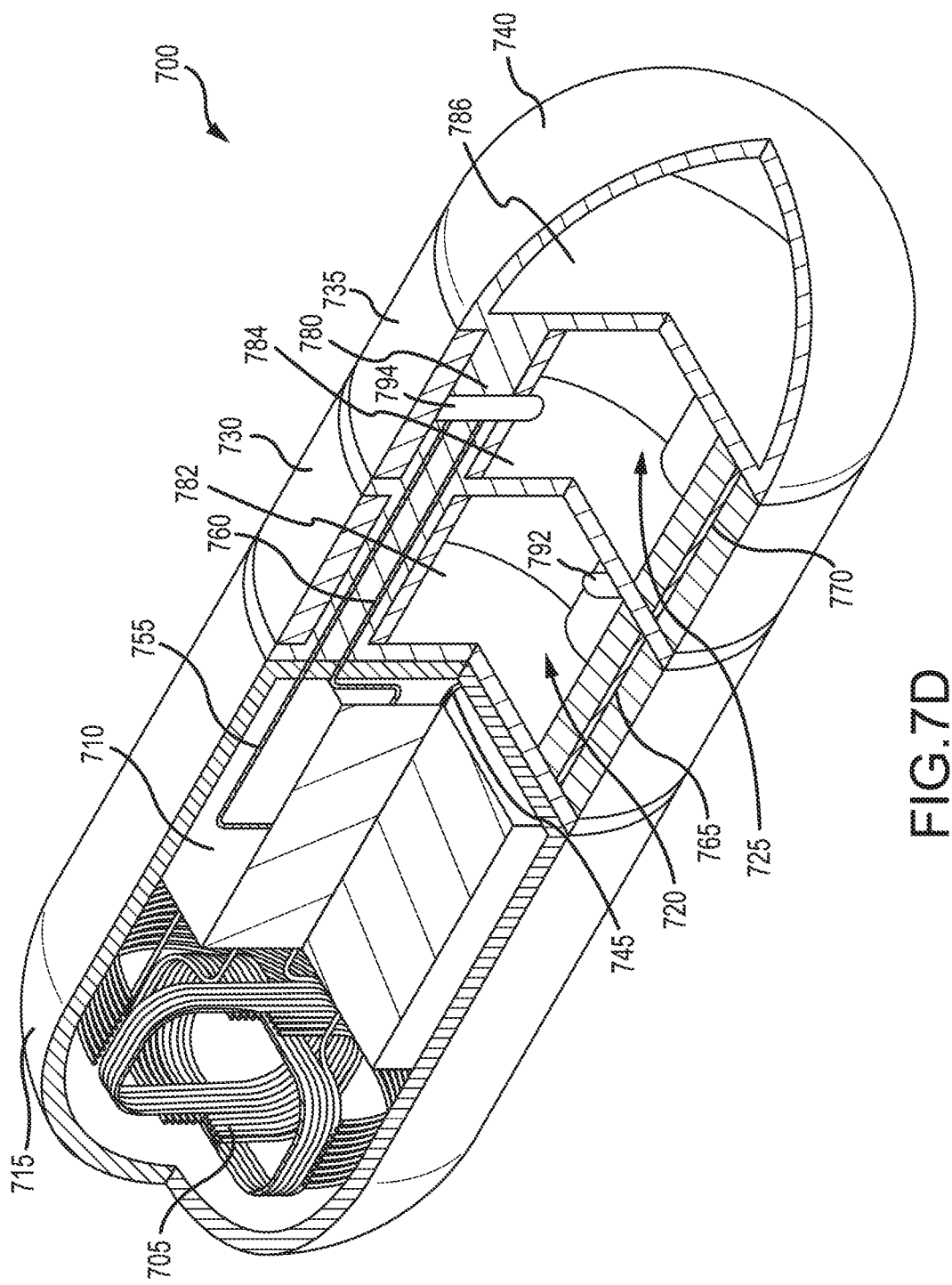

With reference now to FIG. 7D, a partial cross-sectional view illustrating an example of an alternative embodiment of the consumable capsule 700 is shown, in accordance with various aspects of the present disclosure. FIGS. 7E and 7F further illustrate sectional views of the alternative embodiment of the consumable capsule 700.

In this embodiment, the actuators 730 and 735 are partially or entirely made from a stimuli responsive material that utilizes photo-responsive smart shape-changing polymers or liquid crystalline elastomers (LCE), as further described herein. The photo-responsive smart shape-changing polymers use photons or light as an energy input. The photons or light are generated by LEDs 792 and 794. The LEDs 792 and 794 may be one or more of the rectification diodes 682C, 682D, 684C, 684D, 686C, 686D, or the LED 694, described in reference to FIG. 6C. In some embodiments, each of the LEDs 792 and 794 may include multiple LEDs capable of emitting light at different wavelengths. The control electronics 710 provide power to LED(s) 792 over the first positive power line 745 and the first negative power line 750 (shown in FIG. 7E). When the LED(s) 792 emits light, the photo-responsive actuator 730 changes shape and an opening is created for the active ingredient within the first delivery compartment 720 to be released. In a similar way, the control electronics 710 provide power to LED(s) 794 over the second positive power line 755 and the second negative power line 760, which causes the photo-responsive actuator 735 to change shape.

These types of photo-responsive actuators 730 and 735 have a number of features such as ability to be remotely controlled with high speed and spatial precision, have large strain actuation, require low voltage, work at room temperature or body temperature, can operate in liquid electrolytes or body fluids, and can be microfabricated. Photon energy may be converted to mechanical work in the photo-responsive actuators 730 and 735 using two major mechanisms: reversible structural change upon photo irradiation such as photo-isomerization, charge generation, or initiation of reversible photochemical reaction within the polymer; or local temperature increase upon absorption of photons by the material that leads to actuation in thermal responsive polymer actuators.

In one embodiment, reversible photo-isomerization polymer actuators 730 and 735 may be used. Reversible photo-isomerization polymer actuators 730 and 735 can store external tensile or compression force input as a potential energy and return to their original form upon removal of forces by converting the potential energy to mechanical work. Alternatively, reversible photo-isomerization polymer actuators 730 and 735 may return to their original form by using a different wavelength of light and/or using heat (such as body temperature). Light or photo-irradiation from the LEDs 792 and 794 may be used to convert energy into motion quickly by using photo-responsive macromolecules in the actuators 730 and 735 that are light-energy transducers. Photochemical molecules such as spyropyranes, stilbenes, fulgides, and azobenzenes can change their structure when irradiated with light at a certain wavelength. This structural change results in a local volume change that can be amplified if it is incorporated into the polymer chain; and therefore, exhibit actuation. Azobenzene may be preferred due to its thermal stability and rapid reaction at certain absorbance with reversible property. The azobenzene isomers can be isomerized from trans to cis upon UV light irradiation at 343 nm and from cis to trans upon visible light irradiation at 440 nm. The LEDs 792 and 794 may be capable of emitting light at approximately each of these wavelengths. This may be achieved using one or more LEDs. It is noted that the cis isomer is less stable than the trans isomer due to the steric hindrance; therefore, the cis isomer can also relax back to trans isomer isothermally which is thermodynamically more stable. Overall, the molecules of the actuators 730 and 735 transform from a straight configuration (trans) to a bent configuration (cis), which is responsible for the shape change of the actuators, as shown in FIGS. 8D-8F.

Photo-irradiation of azobenzene (azo) incorporated in liquid-crystalline elastomer (LCE) may induce a reversible 20% shape contraction. It is noted that LCEs are class of stimuli-sensitive materials including liquid-crystal molecules with exceptional actuation properties that can have both elastic properties and anisotropy due to the presence of liquid-crystalline order. One of the unique properties of azobenzene is the reversible transition from trans to cis under UV light and by using a longer wavelength of 440 nm to return the polymer rapidly to its original state. Upon UV light irradiation, an azobenzene actuator may transform rapidly (0.5 second) to a bent or twisted shape.

The actuators 730 and 735 may include azo-LCE material that bends after exposure to 366 nm light and reverts completely to its initial state by irradiating with natural light or exposure to heat (such as body heat). The ability to control bending reversibly using light exposure may allow for faster response and less energy or power requirement. The azo-LCE may be created using azobenzene mesogenic monomer capable of photo-actuation.

The azo-LCE actuators 730 and 735 may be bent after exposure to 366 nm light with the intensity of 2.0 mW/cm−2 for 10 to 35 seconds. The bent azo-LCE actuators 730 and 735 may be completely recovered to their initial flat state after natural light irradiation. A bending maximum can be reached after exposure of the azo-LCE actuators 730 and 735 to UV light for about 35 to 50 seconds.

It is important to optimize the performance of the azo-LCE actuators 730 and 735 by varying the amount of azobenzene, crosslinking density, actuator thickness or dimensions, or the power intensity of the LEDs 792 and 794. The bending moment and actuation speed may be varied by altering the chemistry and alignment of azo-LCE, varying the power intensity of irradiated light, and/or changing the polarization angle of the irradiated light. The crosslink density can influence the actuation-generated force and speed by changing the anisotropy and rigidity of the network of each actuator 730 and 735. The light intensity and exposure time may also influence actuation time and force.

Figure 8A:
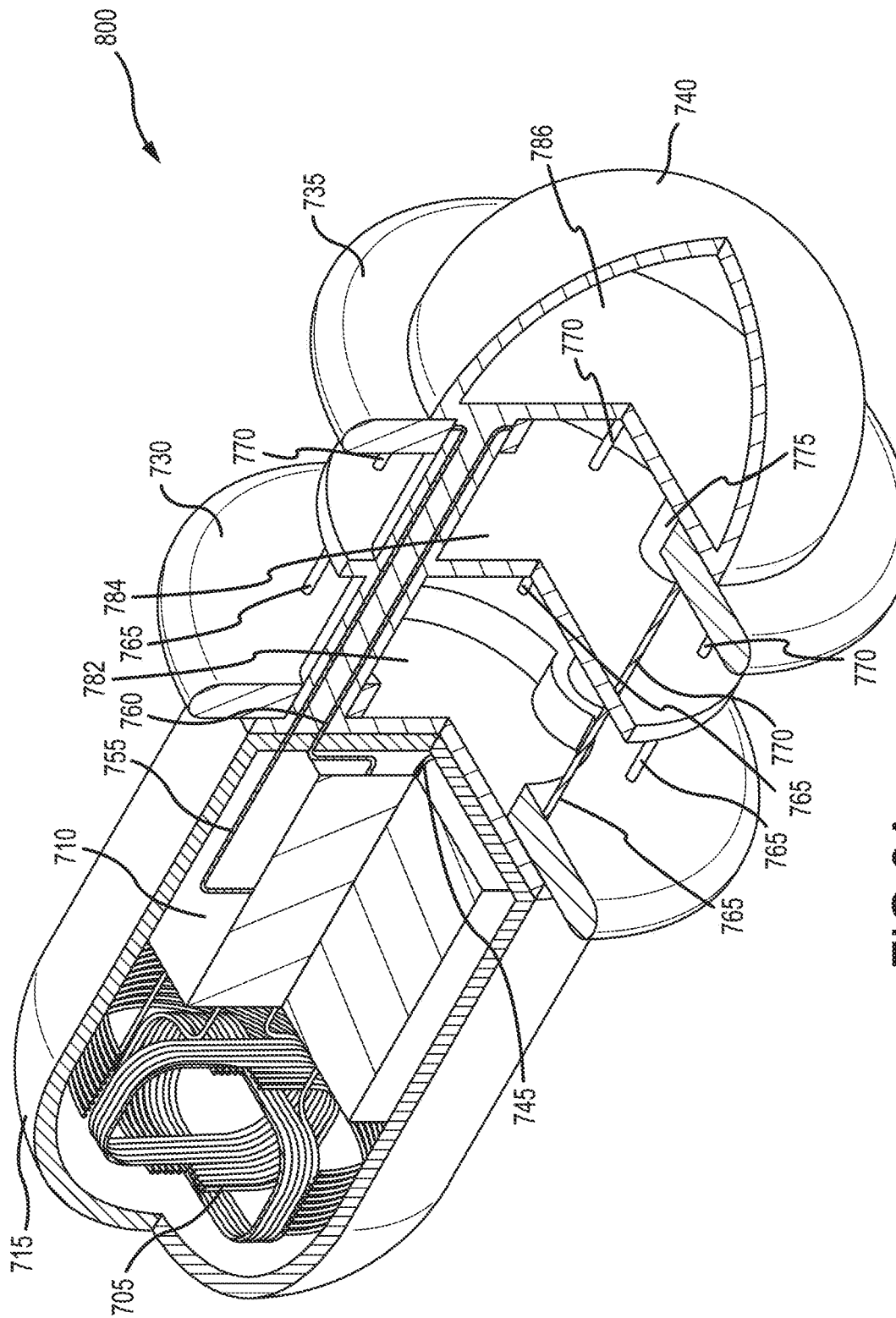
FIGS. 8A-8C illustrate an example of an embodiment of the consumable capsule shown in FIGS. 7A-7C after the delivery compartments are opened, in accordance with various aspects of the present disclosure.

FIG. 8A illustrates a partial cross-sectional view of an example of an embodiment of a consumable capsule 800, in accordance with various aspects of the present disclosure.

Figure 8C:
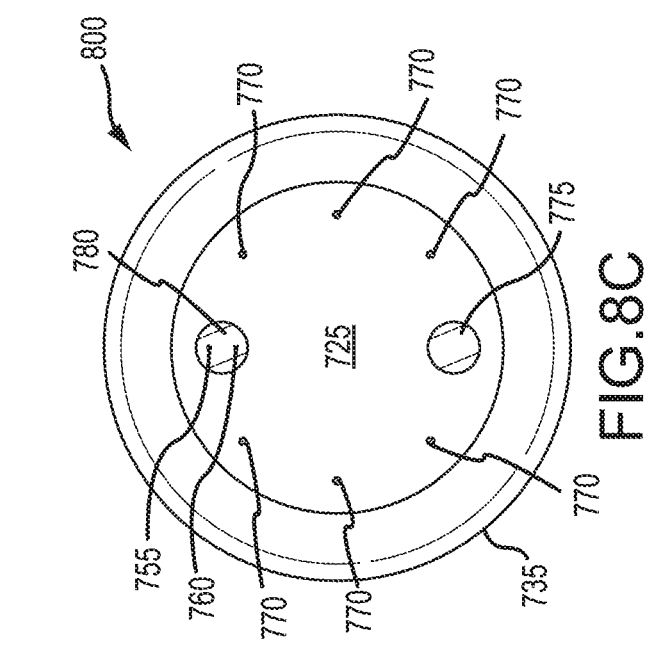
Figure 8B:
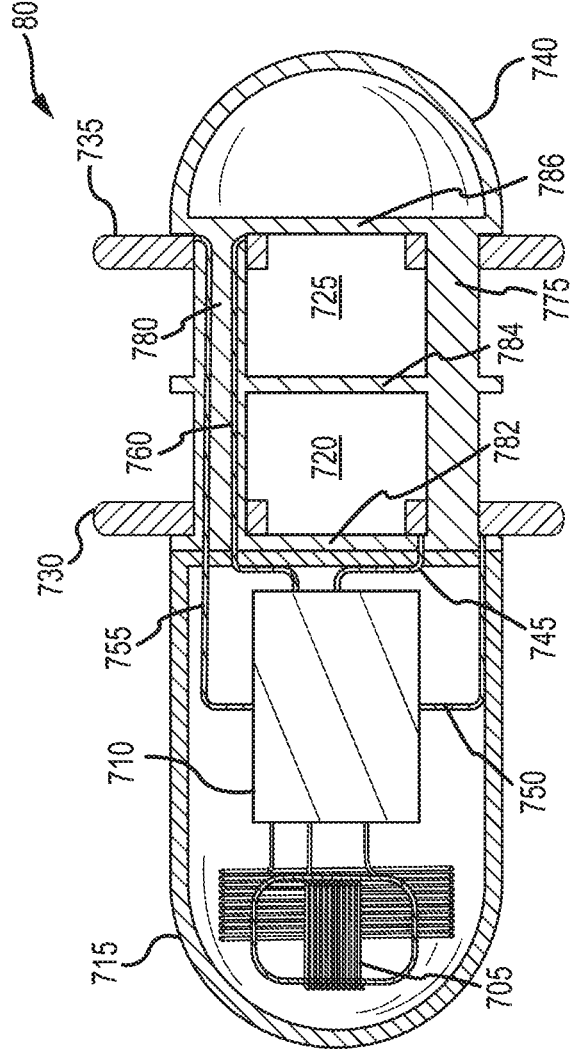
Figure 8D:
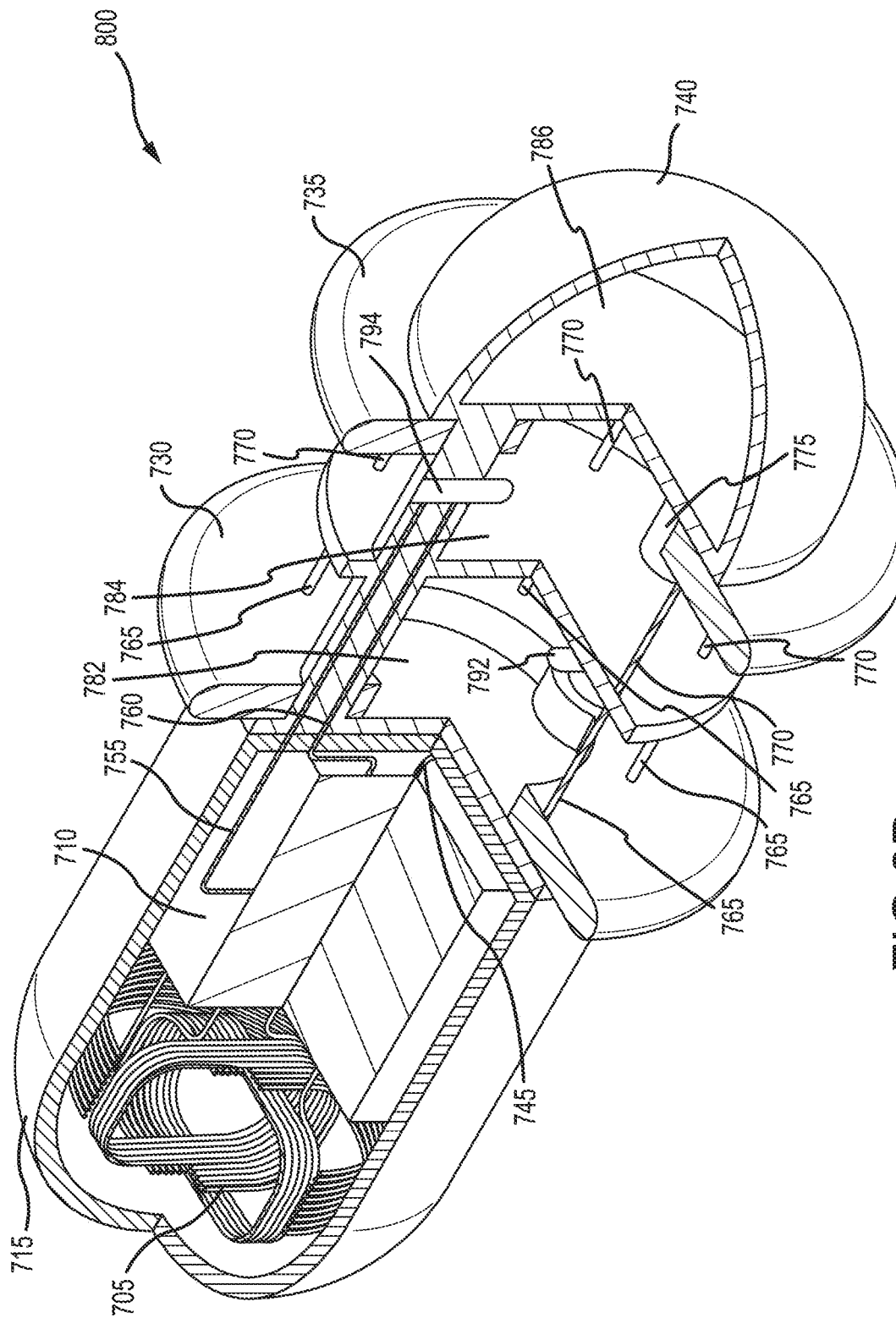

The consumable capsule 800 is an example of the consumable capsule 700 shown in FIGS. 7A-7C after the delivery compartments are opened. FIGS. 8B and 8C further illustrate sectional views of the consumable capsule 800.

As described with reference to FIG. 7A, the first linear actuator 730 changes shape when an electric field is applied. For example, the first linear actuator 730 may compress longitudinally and expand circumferentially, as shown in FIG. 8A. Alternatively, the first linear actuator 730 may change shape in other ways, as further described herein. The resulting shape of the first linear actuator 730 creates an opening which allows the active ingredient within the first delivery compartment 720 to be released into the consumer's GI tract. The second linear actuator 735 changes shape to release an active ingredient in a similar way. While shown with two delivery compartments, one of ordinary skill would understand the consumable capsule 800 may be configured with a single delivery compartment, or three or more delivery compartments.

With reference now to FIG. 8D, a partial cross-sectional view illustrating an example of an alternative embodiment of the consumable capsule 800 is shown, in accordance with various aspects of the present disclosure. The consumable capsule 800 is an example of the consumable capsule 700 shown in FIGS. 7D-7F after the delivery compartments are opened. FIGS. 8E and 8F further illustrate sectional views of the alternative embodiment of the consumable capsule 800.

As described with reference to FIG. 7D, the photo-responsive actuators 730 and 735 change shape when light of certain wavelengths are emitted by the LEDs 792 and 794. For example, the photo-responsive actuators 730 may compress longitudinally and expand circumferentially, as shown in FIG. 8D. Alternatively, the actuators 730 and 735 may change shape in other ways, as further described herein. The resulting shape of the actuators 730 and 735 create openings which allows the active ingredient within the delivery compartments 720 and 725 to be released into the consumer's GI tract. In some embodiments, the photo-responsive actuators 730 and 735 may return to the original shape (as shown in FIGS. 7D-7F) by emitting another wavelength of light with the LEDs 792 and 794. Each of the LEDs 792 and 794 may include multiple LEDs capable of emitting light at different wavelengths. While shown with two delivery compartments, one of ordinary skill would understand the consumable capsule 800 may be configured with a single delivery compartment, or three or more delivery compartments.

Figure 9A:
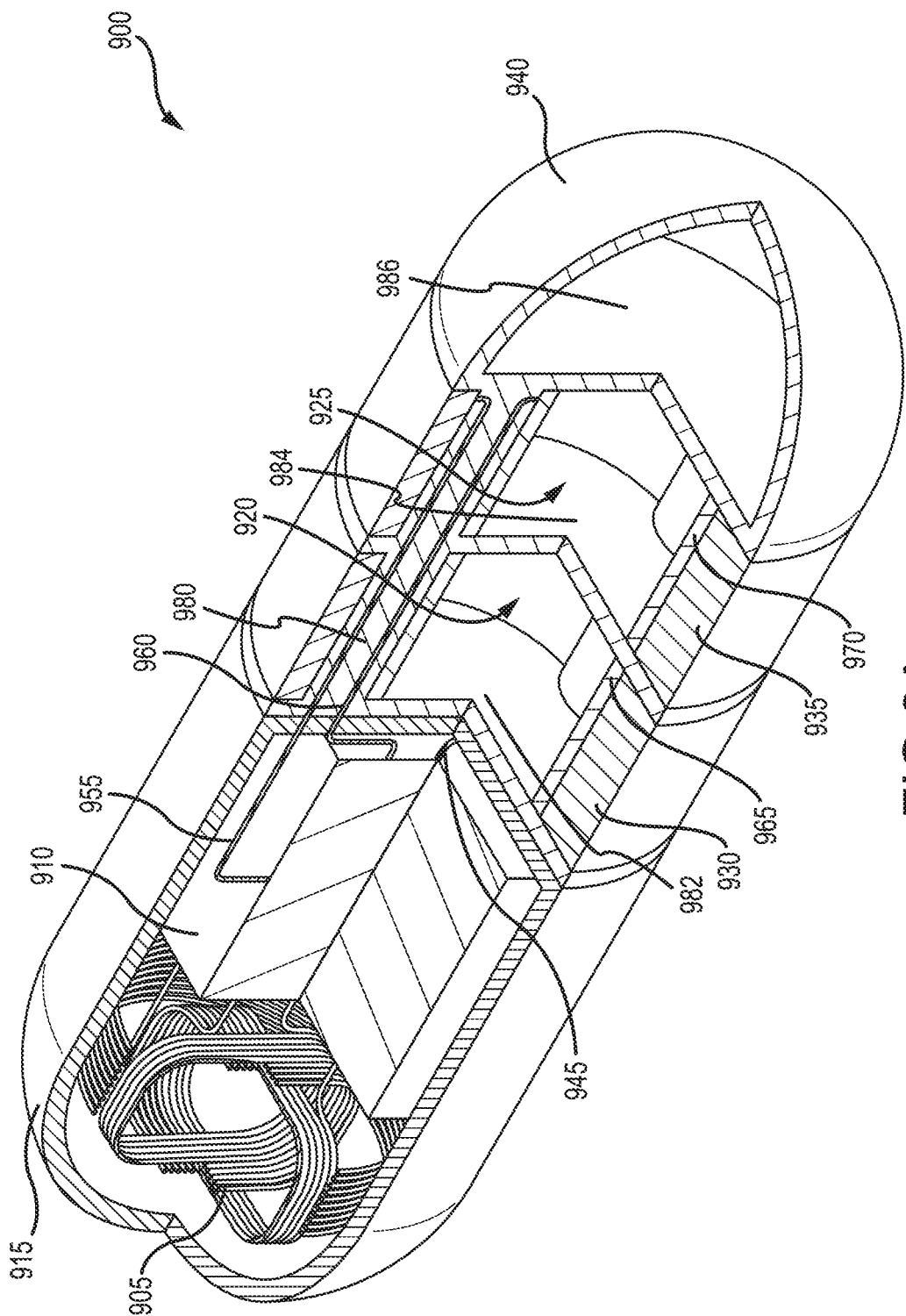

With reference now to FIG. 9A, a partial cross-sectional view illustrating an example of an embodiment of a consumable capsule 900 is shown, in accordance with various aspects of the present disclosure. FIGS. 9B and 9C further illustrate sectional views of the consumable capsule 900.

The consumable capsule 900 includes orthogonal secondary coils 905 and control electronics 910. The orthogonal secondary coils 905 and control electronics 910 are enclosed within an electronics section 915. The consumable capsule 900 also includes a compartment section 940 having a first delivery compartment 920 and a second delivery compartment 925. The first delivery compartment is formed by a first wall 982 and a second wall 984 of the compartment section 940. The first wall 982 and the second wall 984 are connected by a first primary support column 975 (shown in FIGS. 9B and 9C) and a second primary support column 980. The first delivery compartment 920 is sealed by a first bending actuator 930 and a first bending substrate 965.

The second delivery compartment 925 is formed by the second wall 984 and a third wall 986 of the compartment section 940. The first support column 975 (shown in FIGS. 9B and 9C) and the second support column 980 further connect the second wall 984 and the third wall 986. The second delivery compartment 925 is sealed by a second bending actuator 935 and second bending substrate 970. The bending actuators 930 and 935 may be made partially or entirely from stimuli responsive materials. The bending substrates 965 and 970 may made from a bio-compatible metal or other bio-compatible, semi-rigid materials.

In some embodiments, the electronics section 915 and the compartment section 940 may be manufactured independently. The electronics section 915 may then be bonded to the first wall 982 of the compartment section 940 through various bonding techniques, such as sonic welding or with an adhesive. The electronics section 915 and the compartment section 940 may be made from the same or different materials. For example, the electronics section 915 may be made from an inert material that is not digestible (e.g., polyethylene), while the compartment section 940 may be made from a digestible material (e.g., polylactic-co-glycolic acid (PLGA)).

In other embodiments, the electronics section 915 and the compartment section 940 may be manufactured as a single structure from the same material, either inert or digestible.

Each delivery compartment may include an active ingredient. The components of the consumable capsule 900 may further include bio-compatible components, as described in reference to FIGS. 7A-7C. While shown with two delivery compartments, one of ordinary skill would understand the consumable capsule 900 may be configured with a single delivery compartment, or three or more delivery compartments.

The orthogonal secondary coils 905 include three coils arranged orthogonally to one another, as described in reference to FIGS. 7A-7C. The energy received by each of the coils of the orthogonal secondary coils 905 may be used to provide power to the consumable capsule 900. Control electronics 910 may combine the energy received by each of the coils and convert the total received energy into a power source, as described in reference to FIGS. 6A-6C.

The control electronics 910 trigger the release of the active ingredient in the first delivery compartment 920 by applying an electric field to the first bending actuator 930. The control electronics 910 apply the electric field by transmitting an electric current over electrodes, such as first positive power line 945 and first negative power line 950 (shown in FIG. 9B) to the first bending actuator 930. When the electric field is applied to the first bending actuator 930, the actuator changes shape. When the first bending actuator 930 changes shape, an opening is created for the active ingredient within the first delivery compartment 920 to be released. The control electronics 910 trigger the release of the active ingredient in the second delivery compartment 930 in a similar way. The control electronics 910 apply an electric field to the second bending actuator 935 by transmitting an electric current over a second positive power line 955 and a second negative power line 960. The control electronics 910 may be configured to trigger the first and second delivery compartments sequentially or simultaneously, as described above.

The bending actuators 930 and 935 may be made from electro-active polymers (EAPs). The EAPs may include Inherently Conjugated Polymers (ICPs), such as Polypyrrole, Polyaniline, or Polythiopene. When a voltage potential is applied to an ICP, electrons begin moving between the electrodes in the polymer. The speed of this is driven by the surrounding electrolyte ionic conductivity. The movement of charge then attracts ions in the polymer to the electrodes, creating a redox reaction. Ions from the electrolyte diffuse into the polymer to balance the charge in the system, the speed of which is driven by the size of the ions and the structure of the polymer. In some examples, the digestive fluids within the GI tract may function as the electrolyte. The addition of these ions then generates a volume change in the polymer dependent on the modulus of the polymer. The volume change creates a geometric change which is dependent on the shape of the actuator, what it is attached to, etc. For example, the polymer may shrink in volume. When the polymer is attached to a surface of another material that does not shrink (such as the bending substrates 965 and 970), the polymer may cause itself and the other material to curl or bend.

Figure 9D:
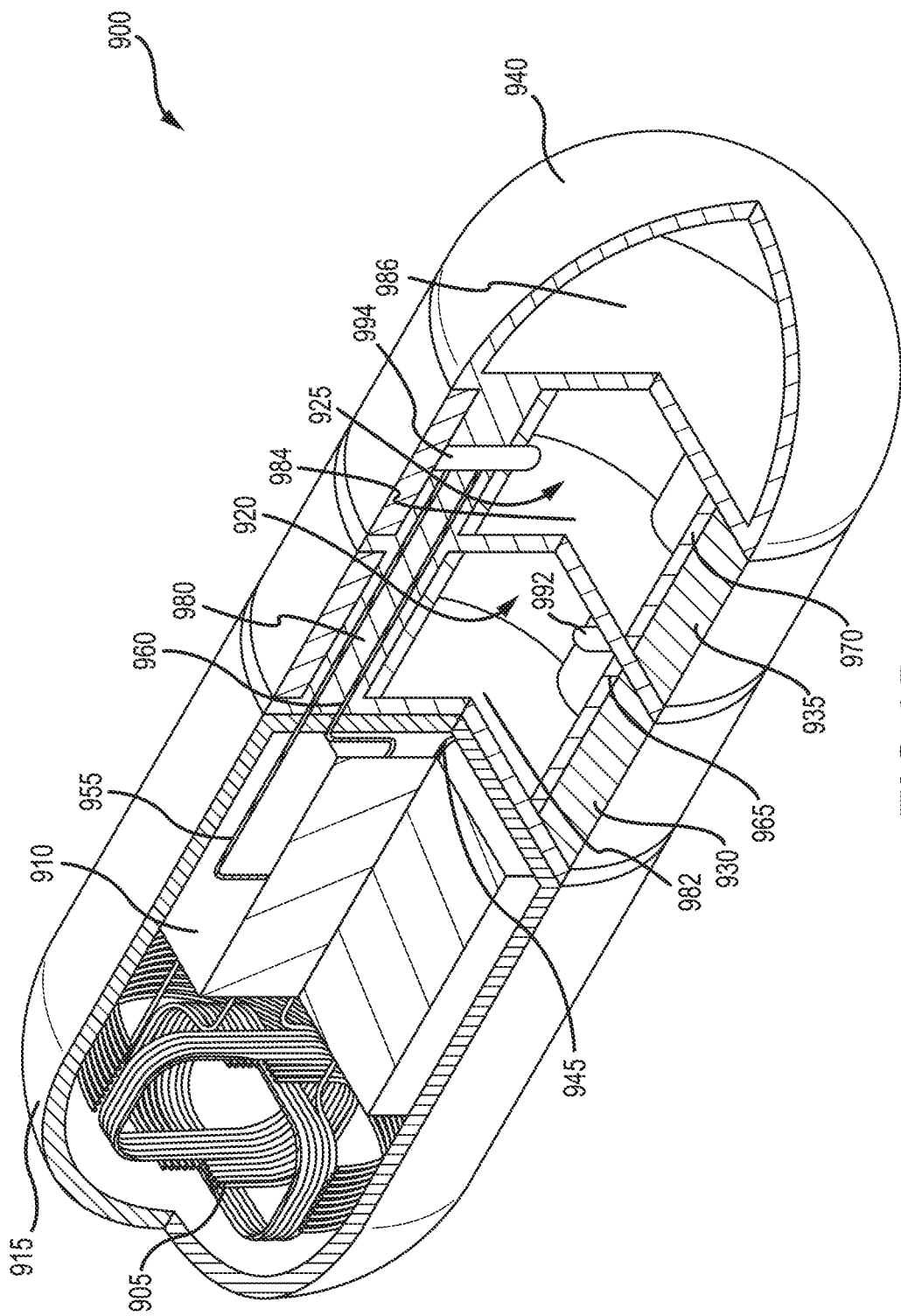

With reference now to FIG. 9D, a partial cross-sectional view illustrating an example of an alternative embodiment of the consumable capsule 900 is shown, in accordance with various aspects of the present disclosure. FIGS. 9E and 9F further illustrate sectional views of the alternative embodiment of the consumable capsule 900.

In this embodiment, the actuators 930 and 935 are partially or entirely made from a stimuli responsive material that utilizes photo-responsive smart shape-changing polymers, as described in reference to FIGS. 7D-7F. The photo-responsive smart shape-changing polymers use photons or light as an energy input. The photons or light are generated by LEDs 992 and 994. The LEDs 992 and 994 may be one or more of the rectification diodes 682C, 682D, 684C, 684D, 686C, 686D, or the LED 694, described in reference to FIG. 6C. In some embodiments, each of the LEDs 992 and 994 may include multiple LEDs capable of emitting light at different wavelengths. The control electronics 910 provide power to LED(s) 992 over the first positive power line 945 and the first negative power line 950 (shown in FIG. 9E). When the LED(s) 992 emits light, the photo-responsive actuator 930 changes shape and an opening is created for the active ingredient within the first delivery compartment 920 to be released. In a similar way, the control electronics 910 provide power to LED(s) 994 over the second positive power line 955 and the second negative power line 960, which causes the photo-responsive actuator 935 to change shape.

Figure 10D:
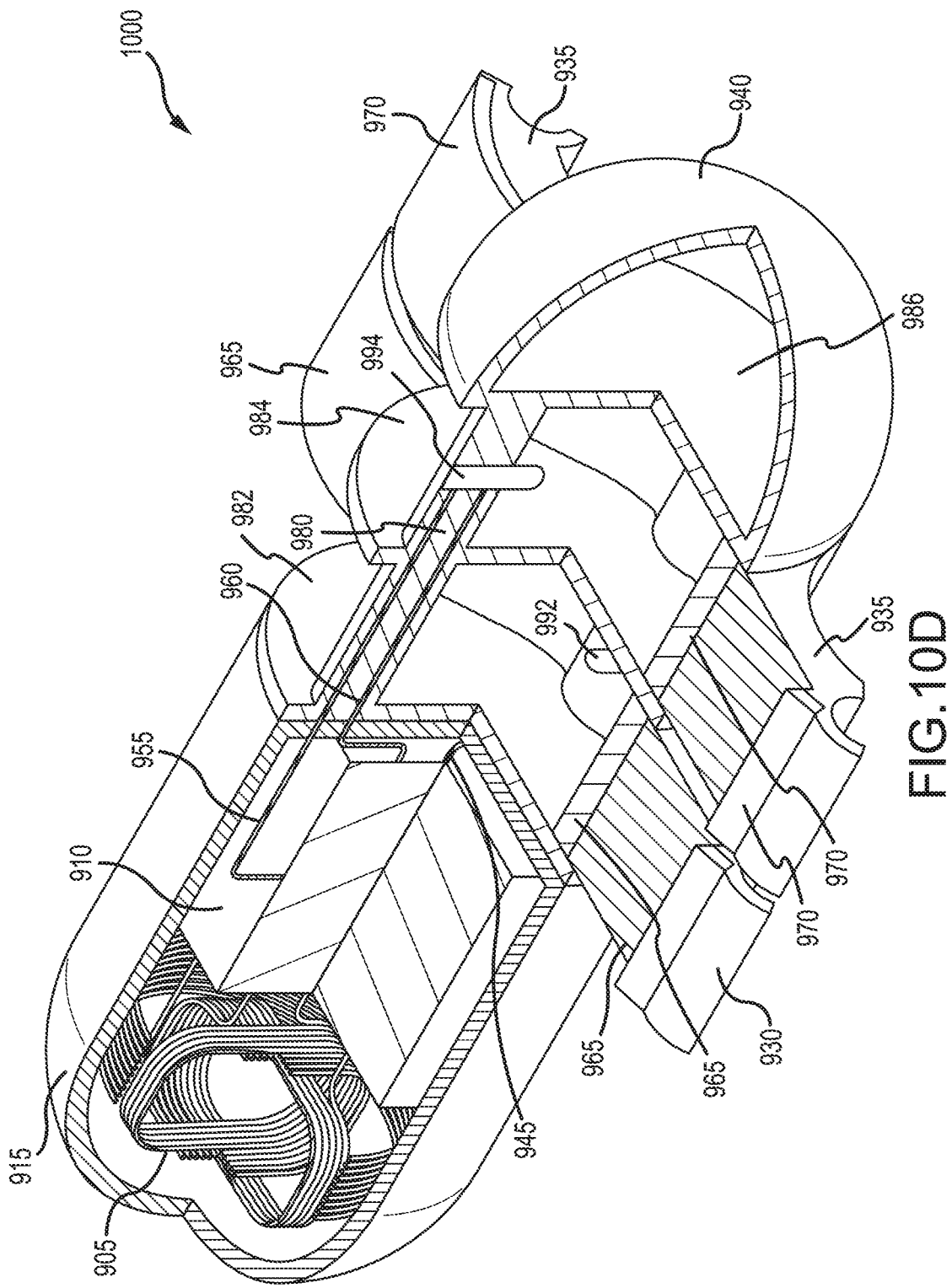

The photo-responsive actuators 930 and 935 operate in a similar manner as described in reference to FIGS. 7D-7F. Overall, the molecules of the photo-responsive actuators 930 and 935 transform from a straight configuration (trans) to a bent configuration (cis) in response to light emitted by the LEDs 992 and 994, which is responsible for the shape change of the actuators, as shown in FIGS. 10D-10F. The actuators 930 and 935 may include azo-LCE material that bends after exposure to 366 nm light and reverts completely to its initial state after irradiating with natural light or exposure to heat (such as body heat). The azo-LCE actuators 930 and 935 may be bent after exposure to 366 nm light with the intensity of 2.0 mW/cm−2 for 10 to 35 seconds, as further described in reference to FIGS. 7D-7F.

FIG. 10A illustrates a partial cross-sectional view of an example of an embodiment of a consumable capsule 1000, in accordance with various aspects of the present disclosure. The consumable capsule 1000 is an example of the consumable capsule 900 shown in FIGS. 9A-9C after the delivery compartments are opened. FIGS. 10B and 10C further illustrate sectional views of the consumable capsule 1000.

As described with reference to FIG. 9A, the first bending actuator 930 changes shape when an electric field is applied. As shown in FIG. 10A, the first bending actuator 930 may bend outward from the consumable capsule. The bending is produced by the first bending actuator 930 being attached to the first bending substrate 965. As the volume of the first bending actuator 930 decreases due to the electric field applied by the electronics section 910, the portion of the first bending actuator 930 attached to the first bending substrate 965 is prevented from decreasing in volume by the same amount. This causes the first bending actuator 930 to curl outward from the consumable capsule 1000. The resulting shape of the first bending actuator 930 creates an opening which allows the active ingredient within the first delivery compartment 920 to be released into the consumer's GI tract. The second bending actuator 935 changes shape to release an active ingredient in a similar way. While shown with two delivery compartments, one of ordinary skill would understand the consumable capsule 1000 may be configured with a single delivery compartment, or three or more delivery compartments.

With reference now to FIG. 10D, a partial cross-sectional view illustrating an example of an alternative embodiment of the consumable capsule 1000 is shown, in accordance with various aspects of the present disclosure. The consumable capsule 1000 is an example of the consumable capsule 900 shown in FIGS. 9D-9F after the delivery compartments are opened. FIGS. 10E and 10F further illustrate sectional views of the alternative embodiment of the consumable capsule 1000.

As described with reference to FIG. 9D, the photo-responsive actuators 930 and 935 change shape when light of certain wavelengths are emitted by the LEDs 992 and 994. For example, the photo-responsive actuators 930 may bend outward from the capsule, as shown in FIG. 8D. Alternatively, the actuators 930 and 935 may change shape in other ways, as further described herein. The resulting shape of the actuators 930 and 935 create openings which allows the active ingredient within the delivery compartments 920 and 925 to be released into the consumer's GI tract. In some embodiments, the photo-responsive actuators 930 and 935 may return to the original shape (as shown in FIGS. 9D-9F) by emitting another wavelength of light with the LEDs 992 and 994. Each of the LEDs 992 and 994 may include multiple LEDs capable of emitting light at the desired wavelengths. While shown with two delivery compartments, one of ordinary skill would understand the consumable capsule 1000 may be configured with a single delivery compartment, or three or more delivery compartments.

In some embodiments, the actuators described in reference to FIGS. 7A-10F may utilize other types of shape-changing materials or "smart" polymers, such as shape memory polymers and liquid-crystalline elastomers. Shape memory polymers (SMP) and Liquid-crystalline elastomers (LCE) exhibit similar behaviors to electro-active polymers (EAP) and shape memory alloys, however the mechanism of actuation is different. The SMP or LCE material is initially formed in a particular shape (shape A), which is then mechanically deformed and fixed in a different shape (Shape B). For example, Shape B may correspond to the closed shape of the actuators shown in FIGS. 7A-7C and 9A-9C, while Shape A may correspond to the open shape of the actuators shown in FIGS. 8A-8C and 10A-10C. Upon the application of a stimulus, for example heat or light, the crosslinking formed by the mechanical deformation into Shape B is released, either by thermal or photo-reactive cleaving of the cross-linked bonds, causing the SMP or LCE material to return to Shape A. For example, light may be applied to a closed SMP or LCE actuator by using an LED included in the consumable capsule, as described above. The light from the LED then causes the SMP or LCE actuator to change into an open shape. This process may be repeatable in some cases, for instance, by applying different wavelengths of light which cause repeating re-organization of the molecules in the material.

LCE materials differ from traditional polymers in that crystalline elements form part of the cross-linked structure. This gives several pronounced differences in behavior for these materials versus polymers. Firstly, the physical response is more anisotropic, depending on the crystalline structure of the material, which make them suitable for the actuators in the present systems, which move along a preferential direction or axis. They also can actuate with lower energy inputs, as the disturbance of part of the crystalline structure causes the entire structure to re-order in some cases.

Other advantages may appear with the use of SMP or LCE materials. For example, the shape memory behavior is based on the molecular structure, not the chemical composition of the polymer. This allows for a much broader range of tailored mechanical and chemical properties to be achieved with similar shape memory behavior. Also, SMP and LCE materials demonstrate response times that can be as short as pico-seconds, which may be advantageous for limiting the amount of electromagnetic energy input to the human body to power the consumable capsule. The SMP materials may be bio-compatible/bio-resorbable and may include PLGA and other bio-compatible/bio-resorbable materials. The LCE materials may be doped with Thio-indigoids to increase the photochromatic response of the system.

In some embodiments, light-actuated SMP materials may be preferable to thermally-actuated materials. Any thermally-actuated SMP intended for use in the body must necessarily have an actuation temperature at least somewhat above the normal human body temperature. Many active ingredients that may be placed into the consumable capsule for targeted delivery may be sensitive to heat, which is more difficult to shield from than is light. Optically-actuated SMP materials are contemplated that actuate at various wavelengths of light, from infrared through ultra-violet. This offers a further advantage that an LED with a high electrical to light conversion efficiency may be used and the SMP material may be designed around the wavelength produced by that LED. In this way, a high power conversion efficiency may be achieved in the consumable capsule, lowering the necessary power input to the body. In some embodiments, a bio-compatible organic LED may be used. For example, an organic LED using DNA as an electron-blocking layer may be used. This type of organic LED has a high luminous efficiency and total luminous power. The wavelength at which such LEDs emit light may be tuneable by adjusting the materials used to construct the LED.

Furthermore, in some embodiments, shape changing or smart polymers may also function as means to move the consumable capsule about within the body. For example, the smart polymer may be shaped into "flagellum" or "fins" which may propel the consumable capsule via repetitive bending. The bending may be activated by repeated use LEDs emitting different wavelengths of light.

Figure 11A:
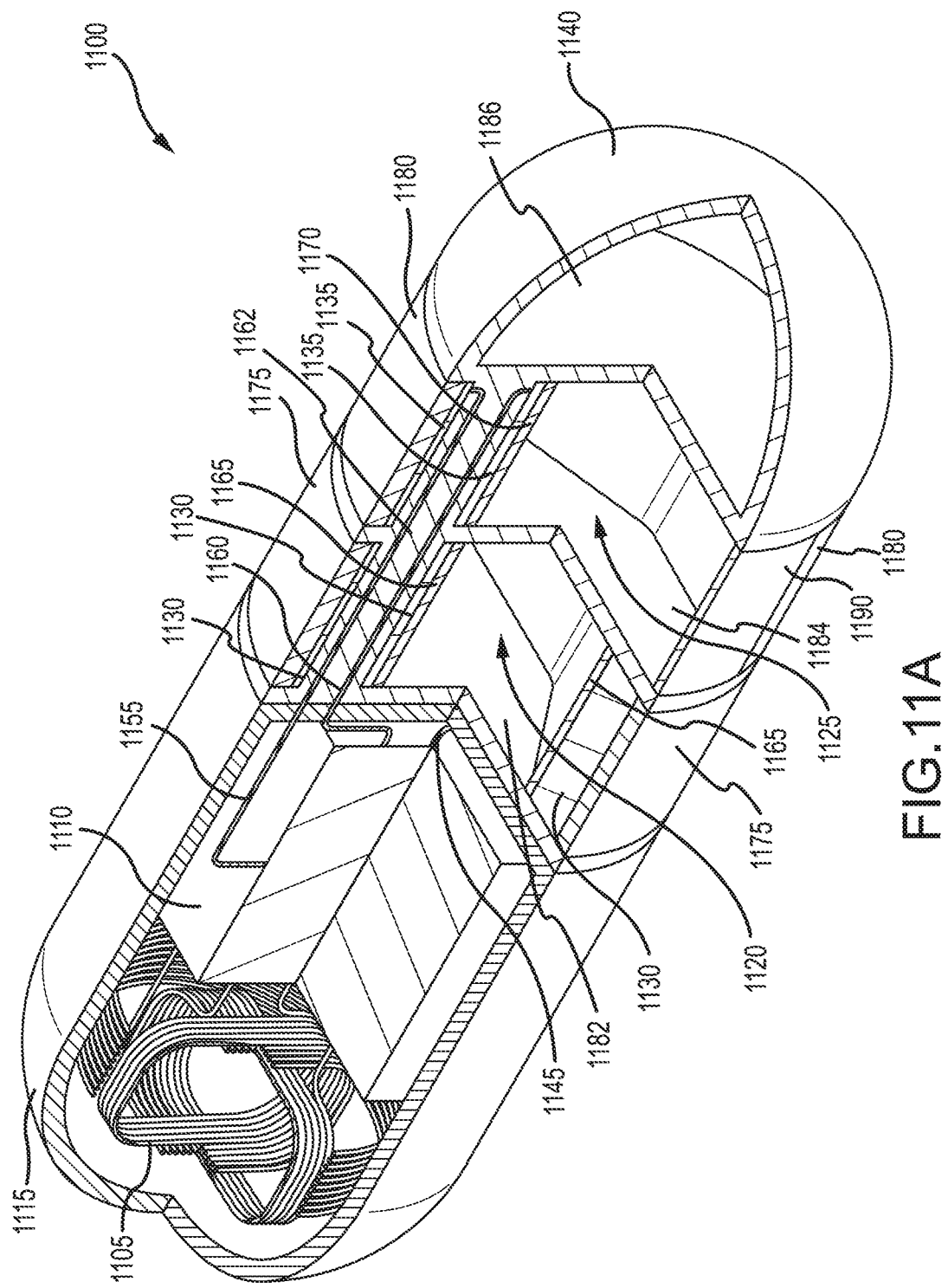

With reference now to FIG. 11A, a partial cross-sectional view illustrating an example of an embodiment of a consumable capsule 1100 is shown, in accordance with various aspects of the present disclosure. FIGS. 11B and 11C further illustrate sectional views of the consumable capsule 900.

The consumable capsule 1100 includes orthogonal secondary coils 1105 and control electronics 1110. The orthogonal secondary coils 1105 and control electronics 1110 are enclosed within an electronics section 1115. The consumable capsule 1100 also includes a compartment section 1140 having a first delivery compartment 1120 and a second delivery compartment 1125. The first delivery compartment is formed by a first wall 1182 and a second wall 1184 of the compartment section 1140. The first wall 1182 and the second wall 1184 are connected by a first primary support column 1152 (shown in FIGS. 11B and 11C) and a second primary support column 1162. A first flexible polymer chamber wall 1165 seals the active ingredient within the first delivery compartment. A first rigid shell 1175 encircles a portion of the first delivery compartment 1120 and first flexible polymer chamber wall 1165. The portion of the first flexible polymer chamber wall 1165 not encircled by the first rigid shell 1175 forms a first flexible polymer burst cover 1185 (shown in FIGS. 12A-12C). A first thermally expansive material 1130 fills the volume between the first flexible polymer chamber wall 1165 and the first rigid shell 1175.

The second delivery compartment 1125 is formed by the second wall 1184 and a third wall 1186 of the compartment section 1140. The first support column 1152 (shown in FIGS. 11B and 11C) and the second support column 1162 further connect the second wall 1184 and the third wall 1186. The second delivery compartment 1125 is sealed by a similar layered structure as the first delivery compartment 1120, including a second flexible polymer chamber wall 1170, a second rigid shell 1180, and a second thermally expansive material 1135 filling the volume between the second flexible polymer chamber wall 1170 and the second rigid shell 1180. The portion of the second flexible polymer chamber wall 1170 not encircled by the second rigid shell 1180 forms a second flexible polymer burst cover 1190.

In some embodiments, the electronics section 1115 and the compartment section 1140 may be manufactured independently. The electronics section 1115 may then be bonded to the first wall 1182 of the compartment section 1140 through various bonding techniques, such as sonic welding or with an adhesive. The electronics section 1115 and the compartment section 1140 may be made from the same or different materials. For example, the electronics section 1115 may be made from an inert material that is not digestible (e.g., polyethylene), while the compartment section 940 may be made from a digestible material (e.g., polylactic-co-glycolic acid (PLGA)).

In other embodiments, the electronics section 1115 and the compartment section 1140 may be manufactured as a single structure from the same material, either inert or digestible.

Each delivery compartment may include an active ingredient. The components of the consumable capsule 900 may further include bio-compatible components, as described in reference to FIGS. 7A-7C. While shown with two delivery compartments, one of ordinary skill would understand the consumable capsule 1100 may be configured with a single delivery compartment, or three or more delivery compartments.

The orthogonal secondary coils 1105 include three coils arranged orthogonally to one another, as described in reference to FIGS. 7A-7C. The energy received by each of the coils of the orthogonal secondary coils 1105 may be used to provide power to the consumable capsule 1100. Control electronics 1110 may combine the energy received by each of the coils and convert the total received energy into a power source, as described in reference to FIGS. 6A-6B.

The control electronics 1110 trigger the release of the active ingredient in the first delivery compartment by heating the first thermally expansive material 1130. The first thermally expansive material 1130 is heated when the control electronics 1110 apply an electric current to the first thermally expansive material 1130. Alternatively, the control electronics 1110 may apply an electric current to heating elements (not shown). The heating elements then heat the first thermally expansive material 1130. The heating elements may be embedded within the first thermally expansive material 1130 or embedded within the compartment section 1140. Alternatively, the heating elements may coat specific surfaces of the compartment section 1140 that are in contact with the first thermally expansive material 1130. For example, portions of the first and second support columns 1152 and 1162 and/or portions the first, second, and third walls 1182, 1184, and 1186 may be coated in a metallic material which acts as a heating element when an electric current is applied by the control electronics 1110. The electric current is supplied to the first thermally expansive material 1130 or heating elements via a first heater power line 1145 and a first heater return line 1150 (shown in FIG. 11B).

When the first thermally expansive material is heated, it expands and pushes on the first flexible polymer chamber wall 1165. The pressure applied by the thermally expansive material causes the portion of the first flexible polymer chamber wall 1165 not encircled by the first rigid shell 1175 (i.e., the first flexible polymer burst cover 1185) to rupture or open. The first flexible polymer burst cover 1185 may include scoring so that a specific portion of the first flexible polymer burst cover 1185 is more likely to rupture. The opened first flexible polymer burst cover 1185 allows the active ingredient in the first delivery compartment 1120 to be released in the consumer's GI tract. The control electronics 1110 trigger the release of the active ingredient in the second delivery compartment 1125 in a similar way—by heating the second thermally expansive material 1135 via a second heater power line 1155 and a second heater return line 1160. The control electronics 1110 may be configured to trigger the first and second delivery compartments sequentially or simultaneously, as described above.

The thermally expansive materials may include medium length n-Alkane paraffin waxes (e.g., n-Alkane paraffin wax having approximately 32 Carbons in the polymer structure), or Calcium Carbonate Tetrahydrate (CaCl2-4H2O). These materials are bio-compatible and exhibit a volume expansion of at least 10% when melting from a solid to liquid phase. Additionally, these materials melt between 35 C and 70 C, which would allow them to remain solid prior to ingestion. Other non-toxic materials exhibiting similar properties may also be used for the thermally expansive materials.

Figure 12A:
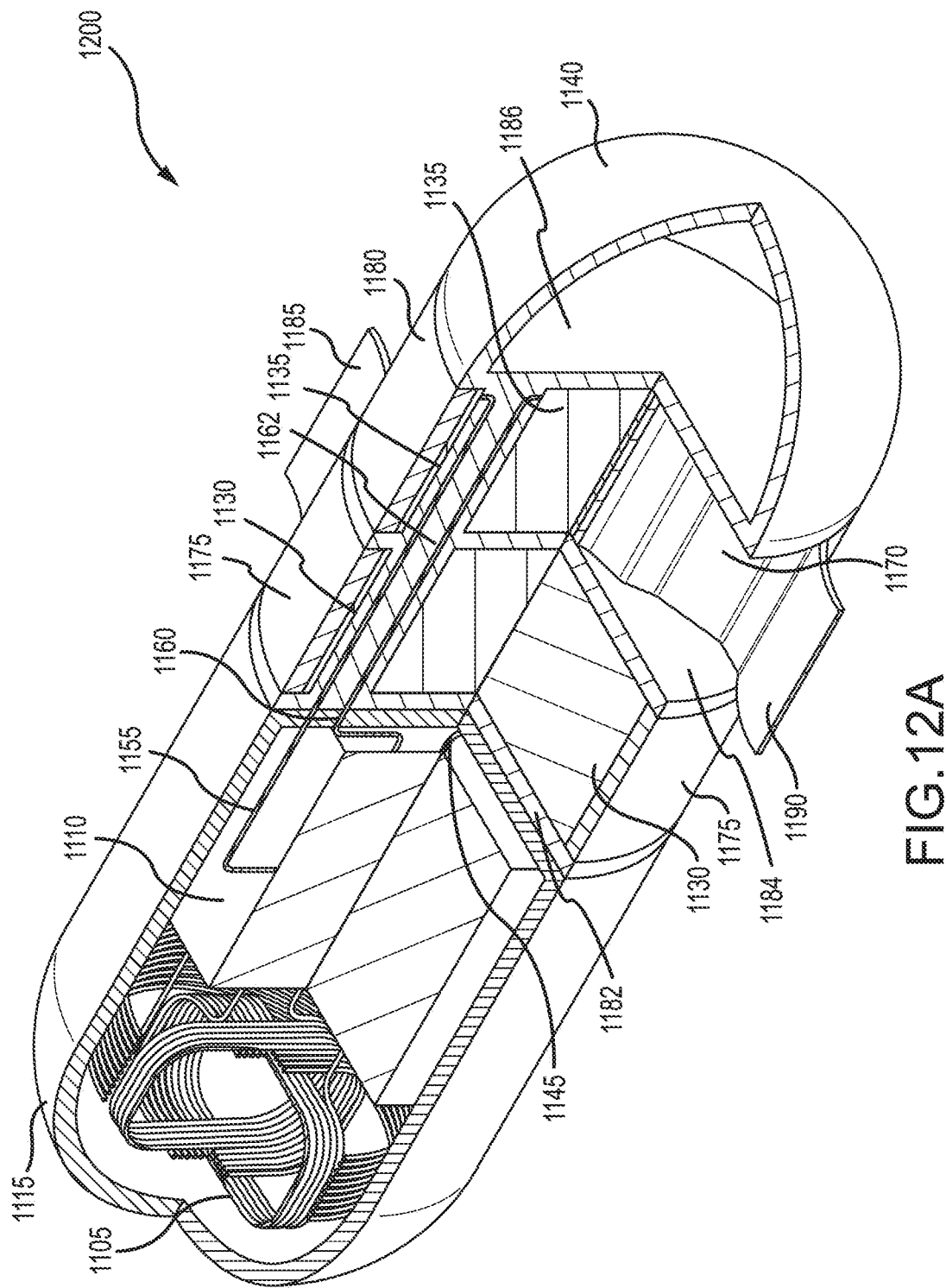

FIG. 12A illustrates a partial cross-sectional view of an example of an embodiment of a consumable capsule 1200, in accordance with various aspects of the present disclosure. The consumable capsule 1200 is an example of the consumable capsule 1100 shown in FIGS. 11A-11C after the delivery compartments are opened. FIGS. 12B and 12C further illustrate sectional views of the consumable capsule 1200.

As described with reference to FIG. 11A-11C, the control electronics 1110 trigger the release of the active ingredient in the delivery compartments 1120 and 1125 by heating the thermally expansive materials 1130 and 1135, causing the material to expand. For example, the first thermally expansive material 1130 expands and pushes on the first flexible polymer chamber wall 1165. The pressure applied by the first thermally expansive material 1130 causes the first flexible polymer burst cover 1185 to rupture or open, as shown in FIGS. 12A-12C. The opened first flexible polymer burst cover 1185 allows the active ingredient in the first delivery compartment to be released in the consumer's GI tract. The control electronics 1110 trigger the release of the active ingredient in the second delivery compartment in a similar way by rupturing the second flexible polymer burst cover 1190 with the pressure created by the expanded second thermally expansive material 1135, as shown in FIGS. 12A-12C. While shown with two delivery compartments, one of ordinary skill would understand the consumable capsule 1200 may be configured with a single delivery compartment, or three or more delivery compartments.

Figure 13A:
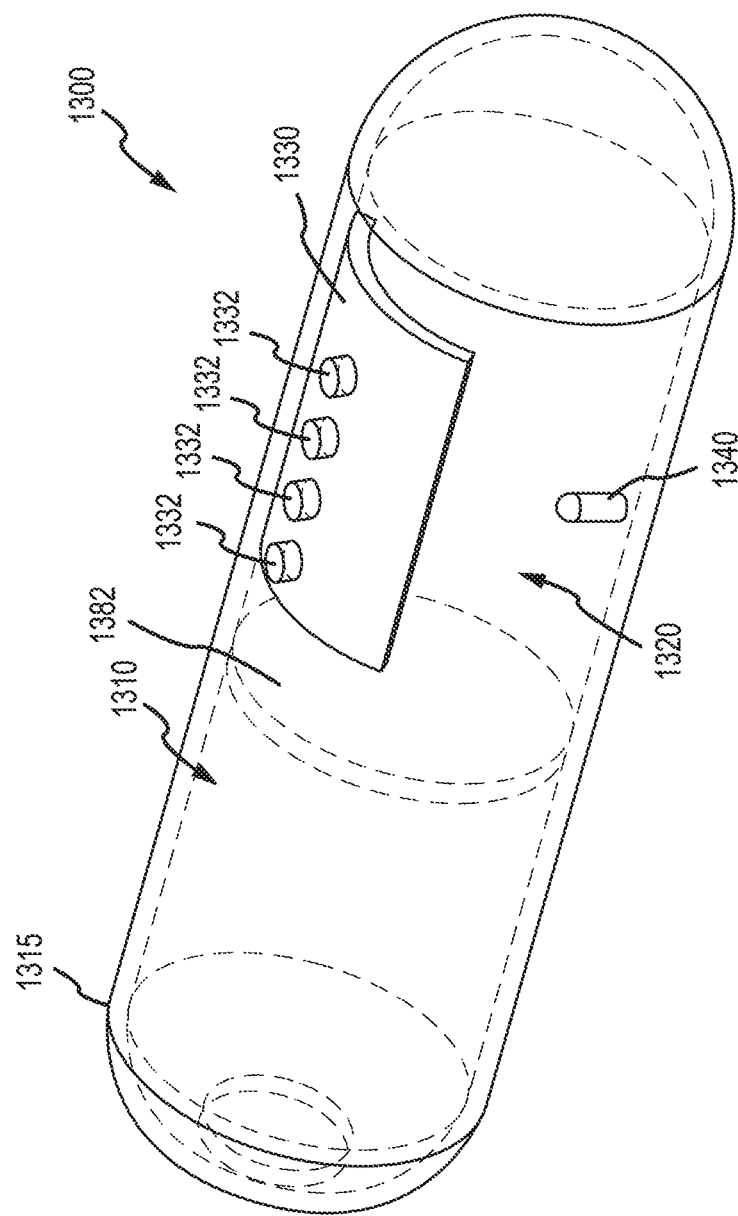
FIGS. 13A-13B illustrate an example of yet another embodiment of a consumable capsule, in accordance with various aspects of the present disclosure.
Figure 13B:
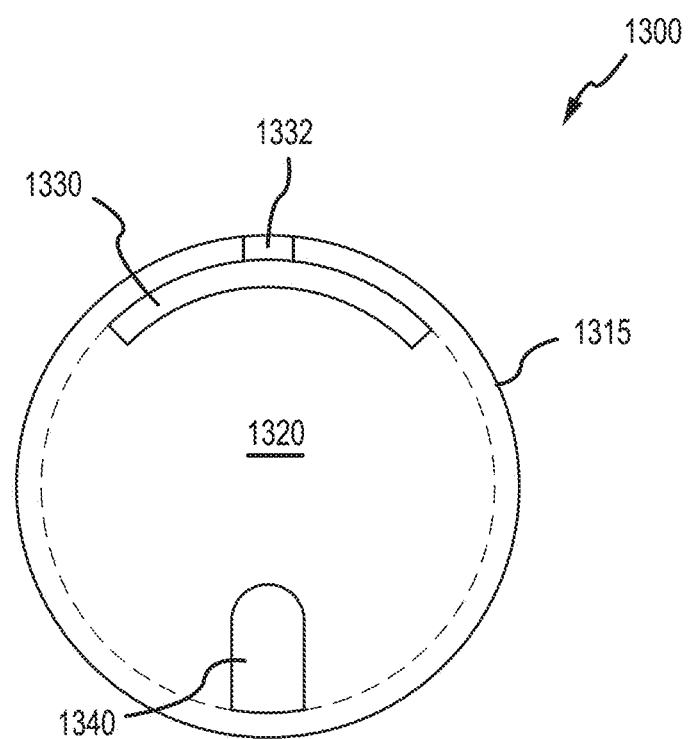

FIG. 13A illustrates a partially transparent view of an example of an embodiment of a consumable capsule 1300, in accordance with various aspects of the present disclosure. FIG. 13B further illustrates a sectional view of the consumable capsule 1300.

The consumable capsule 1300 includes similar components as the consumable capsules described in reference to FIGS. 7A-12C. However, the consumable capsule 1300 includes at least one delivery compartment 1320 movably sealed by a stimuli responsive valve actuator 1330. The stimuli responsive valve actuator 1330 changes shape in responsive to certain wavelengths of light emitted by LED 1340. The LED 1340 may be powered by control electronics 1310 within an electronics section 1315 of the consumable capsule 1300. The control electronics 1310 may distribute power to the LED 1340 and operate in a similar manner as described in reference to FIGS. 6C, 7D-7F, and 9D-9F.

Figure 14A:
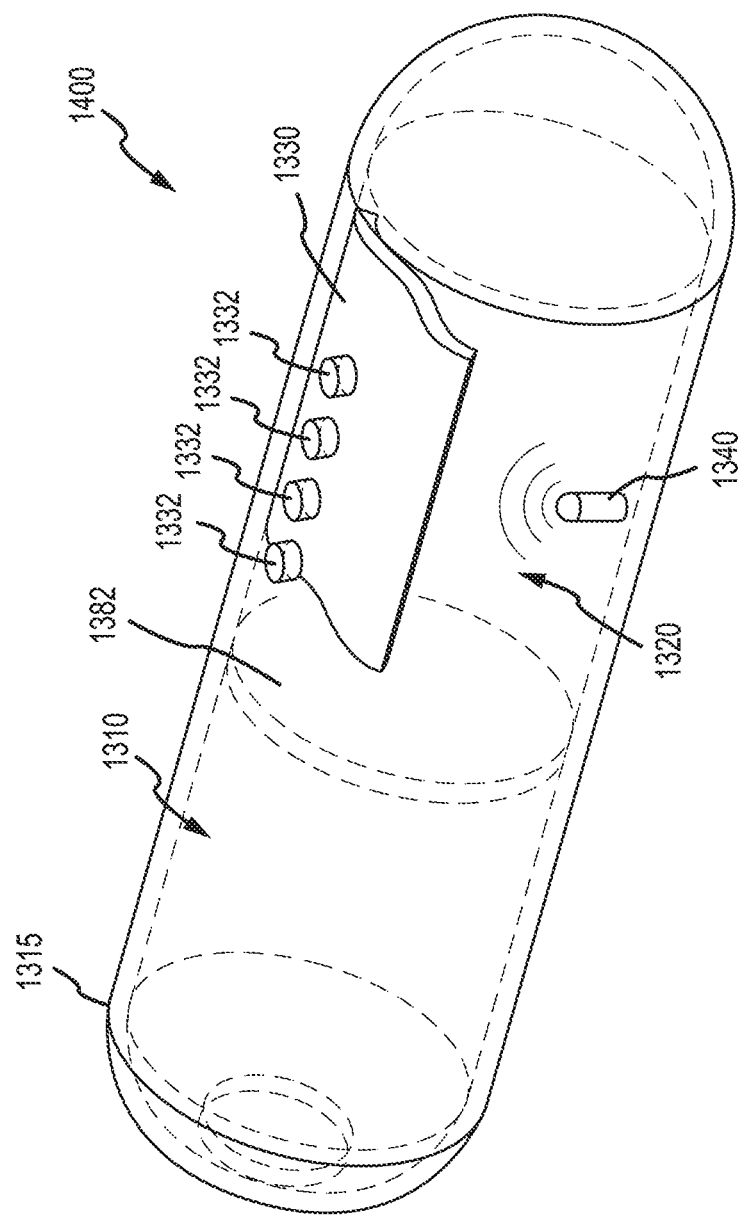
FIGS. 14A-14B illustrate an example of an embodiment of the consumable capsule shown in FIGS. 13A-13C after the delivery compartment is opened, in accordance with various aspects of the present disclosure.
Figure 14B:
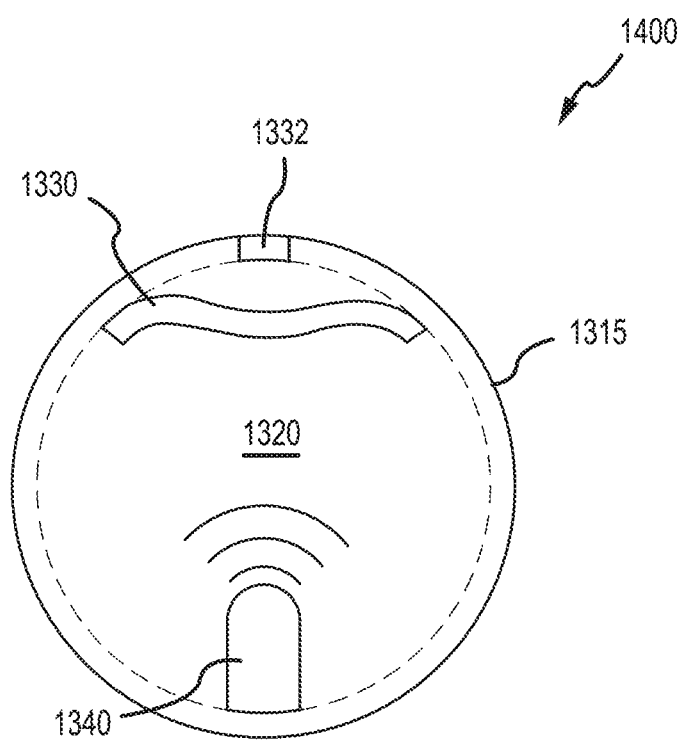

The stimuli responsive valve actuator 1330 changes shape to allow an active ingredient within the delivery compartment 1320 to be released through openings 1332, as further shown in FIGS. 14A and 14B. While shown with four openings 1332 in FIG. 13A, it should be understood that the consumable capsule 1300 may include fewer or more openings 1332. In addition, the consumable capsule 1300 may include additional delivery compartments, each sealed by additional respective stimuli responsive valve actuators. The additional stimuli responsive valve actuators may each be activated by additional respective LEDs, or by the LED 1340. In some embodiments, the LED 1340 may include multiple LEDs capable of emitting light at different wavelengths.

The stimuli responsive valve actuator 1330 operates in a similar manner as described in reference to FIGS. 7D-7F and 9D-9F. Overall, the molecules of the stimuli responsive valve actuator 1330 transform from a straight configuration (trans) to a bent configuration (cis) in response to light emitted by the LED 1340, which is responsible for the shape change of the actuator 1330, as shown in FIGS. 14A-14B. The stimuli responsive valve actuator 1330 may include azo-LCE material that bends after exposure to 366 nm light and reverts completely to its initial state after irradiating with natural light. The azo-LCE valve actuator 1330 may be bent after exposure to 366 nm light with the intensity of 2.0 mW/cm−2 for 10 to 35 seconds, as further described in reference to FIGS. 7D-7F.

FIG. 14A illustrates a partially transparent view of an example of an embodiment of a consumable capsule 1400, in accordance with various aspects of the present disclosure. The consumable capsule 1400 is an example of the consumable capsule 1300 shown in FIGS. 13A-13B after the delivery compartment is opened. FIG. 14B further illustrates a sectional view of the consumable capsule 1400.

As described with reference to FIG. 13A, the stimuli responsive valve actuator 1330 changes shape in response to certain wavelengths of light emitted by LED 1340. As shown in FIG. 14A, the stimuli responsive valve actuator 1330 may deform or bend inwardly toward the center of the capsule 1400. When in this bent shape, a channel is formed between the stimuli responsive valve actuator 1330 and the outer shell of the consumable capsule 1400. This channel allows an active ingredient within the delivery compartment 1320 to be released through openings 1332. FIG. 14B more clearly illustrates the channel between the stimuli responsive valve actuator 1330 and the outer shell of the consumable capsule 1400. In some embodiments, the active ingredient may be pressurized within the delivery compartment 1320 to encourage the active ingredient to flow out of the openings 1332. In some embodiments, the stimuli responsive valve actuator 1330 may return to its original shape (as shown in FIGS. 13A-13B) by emitting another wavelength of light with the LED 1340. The LED 1340 may include multiple LEDs capable of emitting light at different wavelengths. While shown with four openings 1332 in FIG. 14A, it should be understood that the consumable capsule 1400 may include fewer or more openings 1332. In addition, the consumable capsule 1400 may include additional delivery compartments, each sealed by additional respective stimuli responsive valve actuators. The additional stimuli responsive valve actuators may each be activated by additional respective LEDs, or by the LED 1340.

In some embodiments, the consumable capsule is incorporated into a food or beverage product, such that the consumable capsule is ingested by ingesting the food or beverage into which the consumable capsule is incorporated. The food or beverage into which the consumable capsule is embedded is generally not limited. In some embodiments, the consumable capsule is incorporated into a solid food, such as a bar, baked good, or gummy product. In some embodiments, the consumable capsule is incorporated into a yogurt, goo, shake or other viscous food product. In some embodiments, the consumable capsule is incorporated into a liquid, such as juice, water, milk, or the like. The consumable capsule can also be provided in the form a single use packet that is mixed into a beverage, viscous food product, or solid food of the user's choice, such as a bottle of water or a yogurt.

Any suitable method can be used for making the consumable capsules described herein. In some embodiments, the consumable capsule is manufactured using traditional pharmaceutical methods for manufacturing tablets, capsules, pills, beads and the like. In such methods, the active ingredients are mixed together with the binding agents to form a slurry, which is then dried in the desired shape. For the consumable capsule described herein, the internal electronic components can be included with the active ingredients and whatever other components are used to form the consumable capsule product (e.g., binding agents). Any coating layers can then be applied to the consumable capsule, such as by spray coating. In capsule manufacturing, the mixed material is placed inside a capsule which is then sealed together.

Other methods for manufacturing the consumable capsule are contemplated, such as 3D printing technology. 3D printing technology may be used to manufacture one or more components of the capsule, including, for example, the housing, electronic components, support structure components, actuators, and/or active ingredients.

Figure 15:
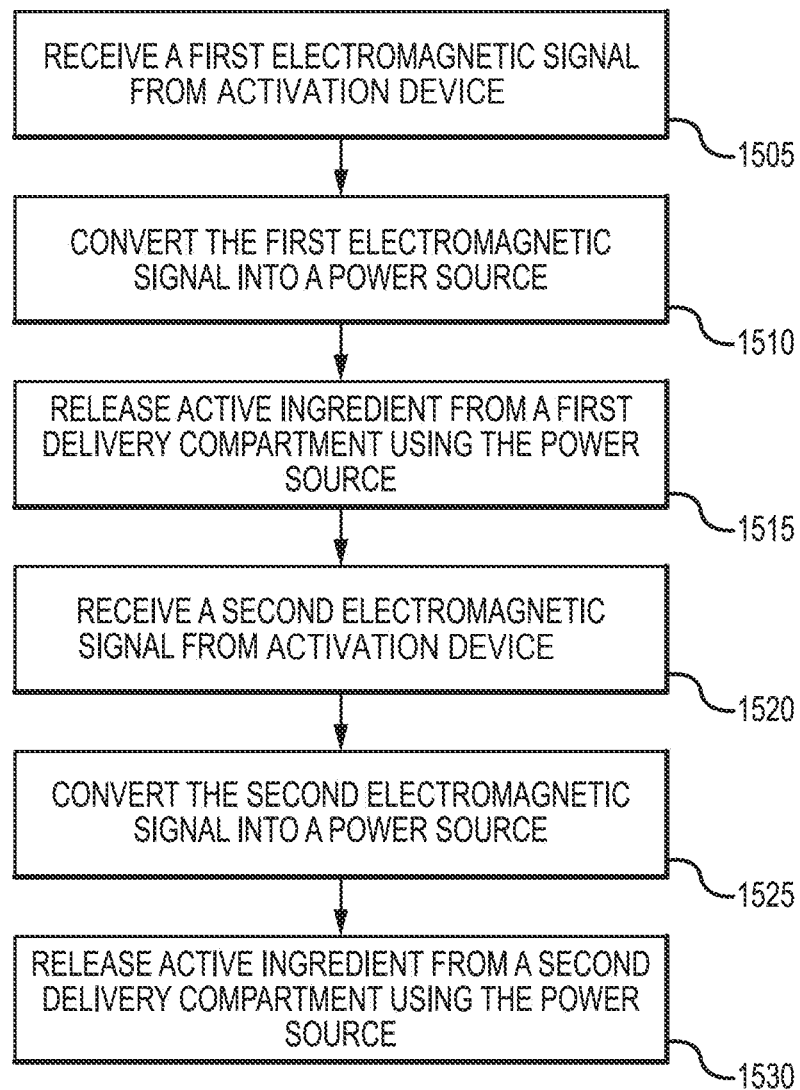
FIG. 15 is a flowchart illustrating an example of a set of operations for triggering the release of active ingredients, in accordance with various aspects of the present disclosure.

FIG. 15 is a flowchart illustrating an example of a set of operations for triggering the release of active ingredients, in accordance with various aspects of the present disclosure. The operations illustrated in FIG. 15 may be executed by an activation device, an external communication device, and/or a combination of devices. The devices may include a memory and one or more processors. These components are examples of various means for performing some of the operations illustrated in FIG. 15.

At block 1505, the set of operations include receiving a first electromagnetic signal by a consumable capsule. In some examples, the first electromagnetic signal may be generated by activation device, in response to a signal from an external communication device. At block 1510, the set of operations include converting the first electromagnetic signal into a power source through inductive coupling. For example, coils within the consumable capsule may generate low level signals from the electromagnetic energy of the first electromagnetic signal. The consumable capsule may then convert the low-level signals into the power source. At block 1515, the set of operations include releasing a first active ingredient from a first delivery compartment using the power source. For example, the consumable capsule may provide power to an actuator, which changes shape to release the first active ingredient.

At block 1520, the set of operations include receiving a second electromagnetic signal by a consumable capsule. In some examples, the second electromagnetic signal may be generated by activation device, in response to a signal from an external communication device. At block 1525, the set of operations include converting the first electromagnetic signal into a power source. For example, coils within the consumable capsule may generate low-level signals from the electromagnetic energy of the second electromagnetic signal. The consumable capsule may then convert the low-level signals into the power source. At block 1530, the set of operations include releasing a second active ingredient from a second delivery compartment using the power source. For example, the consumable capsule may provide power to another actuator, which changes shape to release the second active ingredient. The first and second active ingredients may be the same or different active ingredients.

In some embodiments, the active ingredient in the second delivery compartment may be released without receiving the second electromagnetic signal in block 1520. In these embodiments, the active ingredient in the second delivery compartment is released using the power supplied by the first electromagnetic signal in block 1510. The active ingredient may be released from the second delivery compartment at the same time as the active ingredient in the first delivery compartment. Alternatively, the active ingredient may be released from the second delivery compartment at a predetermined time following the receipt of the first electromagnetic signal, or may be released based on other signals or conditions.

In some embodiments, after the release of the first and/or second active ingredient, the consumable capsule may generate a notification that the active ingredient has been released. Alternatively, an activation device or external communication device may detect the active ingredient has been released based on one or more characteristics of the consumable capsule.

Figure 16:
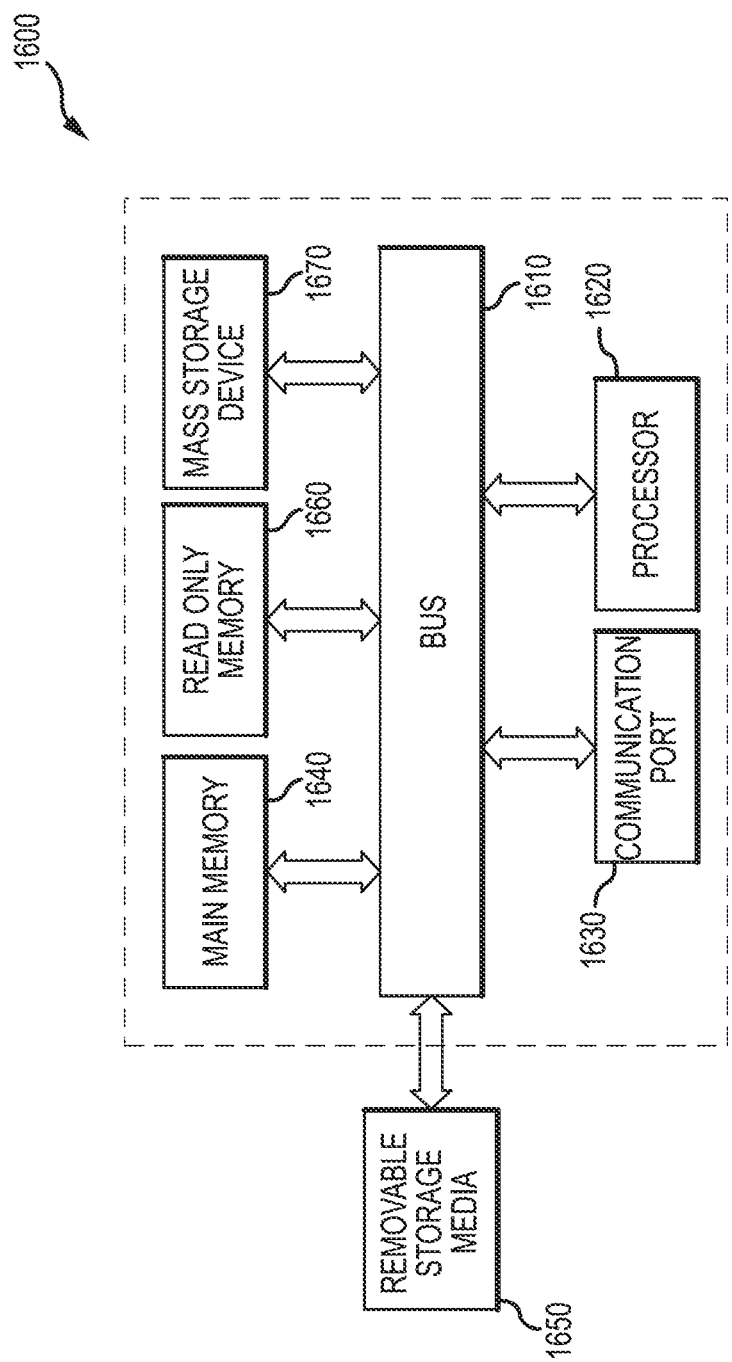
FIG. 16 is an example of an embodiment of a computer system with which embodiments of the present technology may be utilized.

Embodiments of the present technology include various steps and operations, which have been described above. A variety of these steps and operations may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 16 is an example of an embodiment of a computer system 1600 with which embodiments of the present technology may be utilized. For example, the external communication device or activation device may include one or more aspects of the computer system 1600. According to the present example, the computer system 1600 includes a bus 1610, at least one processor 1620, at least one communication port 1630, main memory 1640, a removable storage media 1650, a read only memory 1660, and a mass storage 1670.

Processor(s) 1620 can be any known processor, such as, but not limited to, Intel® lines of processor(s); AMD® lines of processor(s); ARM® lines of processors, or other application-specific integrated circuits (ASICs). Communication port(s) 1630 can be any communication port, such as, but not limited to, an RS-232 port for use with a modem-based dialup connection, a 10/100 Ethernet port, a Gigabit port using copper or fiber, wireless coils, etc. Communication port(s) 1630 may be chosen depending on a network such as a Local Area Network (LAN), Wide Area Network (WAN), cellular network, Near Field Communication (NFC), Bluetooth, or any network on which the computer system 1600 communicates.

Main memory 1640 can be Random Access Memory (RAM) or any other dynamic storage device(s) commonly known in the art. Read only memory 1660 can be any static storage device(s) such as Programmable Read Only Memory (PROM) chips for storing static information such as instructions for processor 1620.

Mass storage 1670 can be used to store information and instructions. For example, a solid state memory, a hard disk, an optical disc, an array of disks such as RAID, or any other mass storage devices may be used.

Bus 1610 communicatively couples processor(s) 1620 with the other memory, storage and communication blocks. Bus 1610 can be any system communication bus, such as, but limited to, I2C, PCI, PCI-Express, UMI, DMI, QPI, etc.

Removable storage media 1650 can be any kind removable storage, such as, but not limited to, external hard-drives, flash memory cards, floppy drives, Compact Disc-Read Only Memory (CD-ROM), Compact Disc-Re-Writable (CD-RW), Digital Video Disk-Read Only Memory (DVD-ROM), Blu-Ray, etc.

Various embodiments of the present disclosure relate to systems, methods, and apparatus for activating a consumable capsule. In one example implementation, a system for activating the consumable capsule includes a consumable capsule containing an active ingredient in at least one compartment movably sealed by a stimuli responsive actuator; and an activation device configured to communicate with the consumable capsule, wherein the activation device is configured to emit a wireless signal to activate the stimuli responsive actuator of the consumable capsule, and wherein the consumable capsule is configured to release the active ingredient into an external environment based on the activation of the stimuli responsive actuator.

In some examples, the system further includes a communication device configured to instruct the activation device to emit the wireless signal. In some examples, the communication device is configured to instruct the activation device to emit the wireless signal based on user input. In some examples, the communication device is configured to instruct the activation device to emit the wireless signal based on at least one physical attribute of a user. In some examples, the communication device is configured to instruct the activation device to emit the wireless signal based on at least one environmental attribute. In some examples, the stimuli responsive actuator comprises azobenzene incorporated in a liquid-crystalline elastomer. In some examples, the stimuli responsive actuator is activatable based at least in part on light emitted in response to the wireless signal. In some examples, the communication device and the activation device are in a common housing. In some examples, the consumable capsule comprises at least one coil for receiving the wireless signal. In some examples, the consumable capsule is powered by the wireless signal. In some examples, the activation device is a wearable item for encircling a user's abdomen. In some examples, the activation device is configured to detect a release status of the active ingredient. In some examples, the activation device is configured to provide an indication of a release status of the active ingredient. In some examples, said indication comprises one or more of a visual indication, an audible indication, and a tactile indication. In some examples, said indication comprises an acknowledgement signal transmittable to a communication device. In some examples, the active ingredient comprises one or more of stimulants, electrolytes, vitamins, minerals, nitroglycerin, and appetite suppressant.

In another example implementation, the consumable capsule includes a signal receiving section comprising at least one coil configured to receive a wireless signal; a control section configured to condition the wireless signal received by the at least one coil into a trigger signal for the consumable capsule; a compartment section comprising at least one capsule compartment movably sealed by a stimuli responsive actuator, the compartment section being configured to activate the stimuli responsive actuator in response to the trigger signal from the control section to allow for release of an active ingredient contained in the at least one capsule compartment into an external environment.

In some examples, the at least one coil comprises three orthogonal coils. In some examples, the stimuli responsive actuator comprises azobenzene incorporated in a liquid-crystalline elastomer. In some examples, the compartment section further comprises a light source configured to emit light based at least in part on the trigger signal, and wherein the stimuli responsive actuator is activated based at least in part on the emitted light. In some examples, the compartment section comprises at least two capsule compartments, the compartment section configured to release an active ingredient contained in the at least two capsule compartments approximately simultaneously. In some examples, the compartment section comprises a plurality of capsule compartments, the compartment section being configured to sequentially open each capsule compartment of the plurality of capsule compartments. In some examples, a first capsule compartment of the plurality of capsule compartments is opened based on the trigger signal, and a second capsule compartment of the plurality of capsule compartments is opened based on a secondary trigger signal from the control section. In some examples, the secondary trigger signal is transmittable by the control section in response to a secondary wireless signal received by the at least one coil. In some examples, the secondary trigger signal is transmittable by the controller a predetermined time after the first capsule compartment is opened. In some examples, the predetermined time is user configurable. In some examples, the consumable capsule further includes a transmitter section configured to report a status of the consumable capsule to an external device that is indicative of an open state of at least one capsule compartment. In some examples, the control section conditions the wireless signal into a direct current (DC) power source. In some examples, the control section includes at least one rectifying circuit for rectifying the wireless signal; and at least filtering circuit for filtering the wireless signal. In some examples, the control section includes at least one rectifying circuit for rectifying the wireless signal, the rectifying circuit comprising at least one light emitting diode (LED), and wherein the at least one LED is configured to activate the stimuli responsive actuator. In some examples, the trigger signal from the control section comprises a DC power signal.

In another example implementation, the consumable capsule includes a housing comprising an outer shell; an electronics section within the housing comprising control electronics and at least one coil; and a compartment section including a support structure connected to the housing; a first wall and a second wall supported by the support structure to define at least one capsule compartment; at least one linear stimuli responsive actuator movably sealing the at least one capsule compartment, the at least one linear stimuli responsive actuator being responsive to a trigger signal transmitted by the control electronics to unseal the at least one capsule compartment.

In some examples, the at least one linear stimuli responsive actuator is responsive to the trigger signal to compress longitudinally and expand circumferentially. In some examples, trigger signal is configured to apply an electric field to the at least one linear stimuli responsive actuator. In some examples, the stimuli responsive actuator comprises at least one of Polypyrrole, Polyaniline, Polythiopene, or a combination thereof. In some examples, the support structure includes at least one rigid connection element embedded in the at least one linear stimuli responsive actuator and connecting the first wall and the second wall. In some examples, the compartment section further includes a positive power line and a negative power line connecting the at least one linear stimuli responsive actuator to the control electronics. In some examples, the positive power line and the negative power line are embedded in the support structure.

In another example implementation, the consumable capsule includes a housing comprising an outer shell; an electronics section within the housing comprising control electronics and at least one coil; and a compartment section including a support structure connected to the housing; a first wall and a second wall supported by the support structure to define at least one capsule compartment; at least one bendable, or otherwise deformable, stimuli responsive actuator movably sealing the at least one capsule compartment, the at least one bending stimuli responsive actuator being responsive to a trigger signal transmitted by the control electronics to unseal the at least one capsule compartment.

In some examples, the at least one bending stimuli responsive actuator comprises a stimuli responsive layer connected to a substrate layer. In some examples, the stimuli responsive layer is responsive to the trigger signal to decrease in volume and cause the at least one bending stimuli responsive actuator to bend or otherwise deform outwardly from the at least one capsule compartment. In some examples, the trigger signal is configured to apply an electric field to the stimuli responsive layer. In some examples, the stimuli responsive actuator comprises at least one of Polypyrrole, Polyaniline, Polythiopene, or a combination thereof. In some examples, the compartment section further includes a positive power line and a negative power line connecting the at least one linear stimuli responsive actuator to the control electronics. In some examples, the positive power line and the negative power line are embedded in the support structure.

In another example implementation, the consumable capsule includes a housing comprising an outer shell; an electronics section within the housing comprising control electronics and at least one coil; and a compartment section including a support structure connected to the housing; a first wall and a second wall supported by the support structure to define a capsule compartment; a chamber wall lining the capsule compartment; a rigid shell encircling a first portion of the chamber wall, wherein a second portion of the chamber wall not encircled by the rigid shell forms a burst cover; and a thermally expansive material filling a volume between the chamber wall and the rigid shell, the thermally expansive material being responsive to a trigger signal transmitted by the control electronics to expand and cause the burst cover to rupture.

In some examples, the trigger signal is configured to heat the thermally expansive material by applying an electric current to the thermally expansive material. In some examples, the trigger signal is configured to heat the thermally expansive material by applying an electric current to one or more heating elements. In some examples, the one or more heating elements are embedded in the support structure. In some examples, the one or more heating elements are embedded in the thermally expansive material. In some examples, the thermally expansive material comprises at least one of paraffin wax, calcium carbonate tetrahydrate, or a combination thereof.

In another example implementation, an activation device includes an attachment mechanism configured to hold the activation device in close proximity to a user's body; and a transmitter configured to emit a wireless signal to a consumable capsule, wherein the wireless signal is configured to activate the consumable capsule, causing the consumable capsule to release an active ingredient.

In some examples, the attachment mechanism comprises an adhesive. In some examples, the attachment mechanism comprises a releasable band of fabric. In some examples, the attachment mechanism is configured to hold the activation device in proximity to the user's abdomen. In some examples, the transmitter comprises a coil of litz wire. In some examples, the transmitter is configured to emit the wireless signal in response to user input. In some examples, the transmitter is configured to emit the wireless signal based on at least one physical attribute of the user. In some examples, the transmitter is configured to emit the wireless signal based on at least one environmental attribute. In some examples, the transmitter is configured to emit the wireless signal in response to an instruction from a communication device. In some examples, the activation device further includes a detector configured to detect a release status of the active ingredient. In some examples, the detector is configured to receive a status signal from the consumable capsule. In some examples, the detector is configured to track a location of the consumable capsule. In some examples, the activation device further includes a user interface configured to provide an indication of the release status of the active ingredient. In some examples, the indication comprises one or more of a visual indication, an audible indication, and a tactile indication. In some examples, the transmitter is configured to transmit an acknowledgement signal to a communication device.

In another example implementation, a method for activating a consumable capsule includes receiving a wireless signal from an activation device; conditioning the wireless signal into a power signal; distributing the power signal to an actuator; modifying a shape of the actuator in response to the power signal; and allowing an active ingredient to be released in response to the modified shape of the actuator.

In another example implementation, a method for activating a consumable capsule includes transmitting a wireless signal to the consumable capsule; receiving a release status of the consumable capsule; and indicating the release status to a user. In some examples, the method includes receiving an instruction from a communication device to transmit the wireless signal to the consumable capsule. In some examples, indicating the release status comprises transmitting the release status to the communication device.

In another example implementation, the consumable capsule includes a housing comprising an outer shell; an electronics section within the housing comprising control electronics and at least one coil; and a compartment section including at least one capsule compartment within the housing; at least one opening extending through the outer shell; at least one light source configured to receive a signal from the control electronics and emit light comprising a first wavelength; and at least one stimuli responsive valve actuator arranged between the at least one opening and the at least one capsule compartment and movably sealing the at least one capsule compartment, the at least one stimuli responsive valve actuator being responsive to the first wavelength of light emitted by the at least one light source to unseal the at least one capsule compartment.

In some examples, the at least one stimuli responsive valve actuator comprises azobenzene incorporated in a liquid-crystalline elastomer. In some examples, the at least one light source is configured to emit light comprising a second wavelength, and wherein the at least one stimuli responsive valve actuator is responsive to the second wavelength of light to reseal the at least one capsule compartment. In some examples, the control electronics comprises at least one rectifying circuit for rectifying a wireless signal received by the at least one coil, the rectifying circuit comprising the at least one light source. In some examples, at least one active ingredient is contained within the at least one capsule compartment, the at least one active ingredient comprising one or more of stimulants, electrolytes, vitamins, minerals, nitroglycerin, and appetite suppressant.

The components described above are meant to exemplify some types of possibilities. In no way should the aforementioned examples limit the scope of the technology, as they are only embodiments.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. A consumable capsule, comprising:
   an outer surrounding sidewall defining a capsule interior;
   a triaxial coil arrangement disposed within the capsule interior for receiving a wireless activation signal and emitting electromagnetic energy in response thereto;
   a control section configured in response to the electromagnetic energy emitted by said triaxial coil arrangement to condition said wireless activation signal into a trigger signal; and
   at least one capsule compartment associated with said outer surrounding sidewall, said at least one capsule compartment storing an active ingredient and being movably sealed by at least one actuator that is responsive to said trigger signal to change its configuration, by compressing longitudinally and expanding circumferentially, to allow for release of the active ingredient into a gastrointestinal tract of a user of the consumable capsule,
   wherein the consumable capsule is configured to interfere with an electromagnetic field generated by an activation device to allow the activation device to estimate a location of the consumable capsule in the gastrointestinal tract of the user,
   wherein the consumable capsule is configured to provide, subsequent to releasing the active ingredient, a feedback signal to the activation device, and
   wherein the consumable capsule is further configured to cause different amounts of interference to the electromagnetic field based on a type or an amount of the active ingredient released.

2. The consumable capsule of claim 1, wherein said triaxial coil arrangement comprises three coils which are oriented substantially orthogonally with respect to one another.

3. The consumable capsule of claim 1 wherein said triaxial coil arrangement comprises a plurality of stacked coils.

4. The consumable capsule of claim 1, wherein said at least one actuator is configured at least partially from a stimuli responsive material.

5. The consumable capsule of claim 1, wherein the trigger signal comprises an electric current that is transmitted to the at least one actuator.

6. The consumable capsule of claim 4, wherein the stimuli responsive material comprises at least one inherently conjugated polymer (ICP).

7. The consumable capsule of claim 1, wherein a material of the outer surrounding sidewall comprises polyethylene or polylactic-co-glycolic acid (PLGA).

8. The consumable capsule of claim 1, wherein the at least one capsule compartment comprises multiple capsule compartments and each capsule compartment comprises a different active ingredient from the other capsule compartments.

9. The consumable capsule of claim 1, wherein the at least one capsule compartment comprises multiple capsule compartments and each capsule compartment comprises a dose of the active ingredient.

10. The consumable capsule of claim 1, wherein the feedback signal is based on a type or an amount of the active ingredient released.

* * * * *